US008273778B2

(12) United States Patent
Kiessling et al.

(10) Patent No.: US 8,273,778 B2
(45) Date of Patent: Sep. 25, 2012

(54) INHIBITORS OF UDP-GALACTOPYRANOSE MUTASE THWART MYCOBACTERIAL GROWTH

(75) Inventors: Laura Lee Kiessling, Madison, WI (US); Emily Carla Dykhuizen, Woodside, CA (US); John F. May, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 267 days.

(21) Appl. No.: 12/430,610

(22) Filed: Apr. 27, 2009

(65) Prior Publication Data
US 2010/0056586 A1 Mar. 4, 2010

Related U.S. Application Data

(60) Provisional application No. 61/048,080, filed on Apr. 25, 2008.

(51) Int. Cl.
*A61K 31/427* (2006.01)
*C07D 407/12* (2006.01)
*C40B 30/00* (2006.01)
*A61P 31/00* (2006.01)

(52) U.S. Cl. .............................. 514/370; 548/194; 506/7

(58) Field of Classification Search .................. None
See application file for complete search history.

(56) References Cited

U.S. PATENT DOCUMENTS

| | | | |
|---|---|---|---|
| 6,734,307 B2 | 5/2004 | Mehta et al. | |
| 6,956,040 B2 | 10/2005 | Mehta et al. | |
| 7,323,482 B2 | 1/2008 | Hynes et al. | |
| 2004/0054195 A1 | 3/2004 | Gao et al. | |
| 2005/0222408 A1 | 10/2005 | Lee et al. | |
| 2005/0261294 A1* | 11/2005 | Mjalli et al. .................. | 514/242 |
| 2006/0089371 A1 | 4/2006 | Murata et al. | |
| 2006/0160868 A1 | 7/2006 | Majka et al. | |
| 2008/0064666 A1 | 3/2008 | Verkman et al. | |

FOREIGN PATENT DOCUMENTS

| | | |
|---|---|---|
| GB | WO2007129048 | * 11/2007 |
| WO | WO 2004/043926 | 5/2004 |
| WO | WO 2005/007625 | 1/2005 |
| WO | WO 2005/103022 | 11/2005 |
| WO | WO 2009/132310 | 10/2009 |

OTHER PUBLICATIONS

Patani et al. in Chemical Reviews, 96, 3147-3176 (1999).*
Park et al. in Annu. Rev. Pharmacol. Toxicol. 2001, 41:443-47.*
Borrelli et al. (2010) "Antimycobacterial activity of UDP-galactopyranose mutase inhibitors," International Journal Antimicrobial Agents 36:364-368.
Caravano et al. (Web Release Apr. 23, 2004) "Efficient Synthesis of a Nucleoside-Diphospho-*exo*-glycal Displaying Time-Dependent Inactivation of UDP-Dependent Inactivation of UDP-Galactopyranose Mutase," *Chem. Commun*. 10:1216-1217.
Caravano et al. (Apr. 3, 2006) "A New Methodology for the Synthesis of Fluorinated *exo*-Glycals and Their Time-Dependent Inhibition of UDP-Galactopyranose Mutase," *Chem. Eur. J*. 12(11):3114-3123.
Caravano et al. (Dec. 5, 2003) "Synthesis and Inhibition Properties of Conformational Probes for the Mutase-Catalyzed UDP-Galactopyranose/Furanose Interconversion," *Chem. Eur. J*. 9(23):5888-5898.
Carlson et al. (Aug. 2006) "Chemical Probes of UDP-Galactopyranose Mutase," *Chem. Biol*. 13(8):825-837.
Castagnolo et al. (2008) "Synthesis, Biological Evaluation and SAR Study of Novel Pyrazole Analogues as Inhibitors of *Mycobacterium tuberculosis*," *Bioorg. Med. Chem*.16:8587-8591.
Chad et al. (Web Release May 19, 2007) "Site-Directed Mutagenesis of UDP-Galactopyranose Mutase Reveals a Critical Role for the Active-Site' Conserved Arginine Residues," *Biochemistry* 46(23):6723-6732.
Dykhuizen et al. (2009) "Potent Ligands for Prokaryotic UDP-Galactopyranose Mutase that Exploit an Enzyme Subsite," *Organic Letts* 11(1) 193-196.
Dykhuizen et al. (Web release May 1, 2008) "Inhibitors of UDP-Galactopyranose Mutase Thwart Mycobacterial Growth," *J. Am. Chem. Soc*. 130:6706-6707 (Plus Supplemental Information).
Ghavami et al. (Jan. 22, 2004) "Synthesis of a Novel Class of Sulfonium Ions as Potential Inhibitors of UDP-Galactopyranose Mutase," *Carbohydr. Res*. 339(2):401-407.
Helm et al. (Web Release Aug. 22, 2003) "Identification of Active-Site Inhibitors of MurG Using a Generalizable, High-Throughput Glycosyltransferase Screen," *J. Am. Chem. Soc*.125(37):11168-11169.
International Search Report and Written Opinion, Corresponding to International Application No. PCT/US09/41719, Mailed Aug. 20, 2009.
Itoh et al. (Web Release Feb. 1, 2007) "Synthesis and Analysis of Substrate Analogues for UDP-Galactopyranose Mutase: Implication for an Oxocarbenium Ion Intermediate in the Catalytic Mechanism," *Org. Lett*. 9(5):879-882.
Lee et al. (Sep. 22, 1997) "Inhibition of UDP-Gal Mutase and Mycobacterial Galactan Biosynthesis by Pyrrolidine Analogues of Galactofuranose," *Tetrahedron Lett*. 38(38):6733-6736.
Lee et al. (Dec. 3, 1999) "An Approach to Combinatorial Library Generation of Galactofuranose Mimics as Potential Inhibitors of Mycobacterial Cell Wall Biosynthesis: Synthesis of a Peptidomimetic of iridine 5'-diphosphogalactofuranose (UDP-Gal*f*)," *Tetrahedron Lett*. 40(49):8689-8692.
Liautard et al. (Published on web Mar. 3, 2006) Stereoselective Synthesis of alpha-C-Substituted 1,4-Dideoxy-1,4-imino-D-galactitols. Toward Original UDP-Gal*f* Mimics via Cross-Metathesis, *Org. Letters*. 8(7):1299-1302.
Liautard et al. (Web Release Aug. 23, 2006) "Diastereoselective Synthesis of Novel Iminosugar-Containing UDP-Gal*F* Mimics: Potential Inhibitors of UDP-Gal Mutase and UDP-Gal*f* Transferases," *J. Org. Chem*. 71(19):7337-7345.
Lokhov et al. (Sep. 1992) "Synthesis and High Stability of Complementary Complexes of N-(2-Hydroxyethyl)phenazinium Derivatives of Oligonucleotides," *Bioconjugate Chem*. 3(5):414-419.

(Continued)

*Primary Examiner* — Brandon Fetterolf
*Assistant Examiner* — Dennis Heyer
(74) *Attorney, Agent, or Firm* — Greenlee Sullivan P.C.

(57) ABSTRACT

Compounds which inhibit microbial growth or attenuate the virulence of pathogen microorganisms. Compounds of the invention inhibit UDP-galactopyranose mutase (UGM) and have activity as inhibitors of microbial growth of microorganisms which contain this enzyme and particularly those microorganisms in which this enzyme is responsible for the incorporation of galactofuranose residues, particularly for uridine 5'-diphosphate (UDP) galactopyranose mutase. Compounds of the invention inhibit UDP-galactopyranose mutase (UGM) and have activity to attenuate virulence of pathogenic microorganisms, including mycobacteria.

5 Claims, 28 Drawing Sheets

OTHER PUBLICATIONS

Pan et al. (Jun. 18, 2007) "Synthesis of Acyclic Galactitol- and Lyxitol-Aminophosphonates as Inhibitors of UDP-Galactopyranose Mutase," *Tetrahedron Lett.* 48(25):4353-4356.

Pan et al. (Dec. 2001) "Cell Wall Core Galactofuran Synthesis is Essential for Growth of Mycobacteria," *J. Bacteriol.* 183(13):3991-3998.

Pederson et al. (2003) "Galactofuranose Metabolism: A Potential Target for Antimicrobial Chemotherapy," *Cell. Mol. Life Sci.* 60:259-266.

Scherman et al. (Jan. 2003) "Drug Targeting *Mycobacterium tuberculosis* Cell Wall Synthesis: Development of a Microtiter Plate-Based Screen for UDP-Galactopyranose Mutase and Identification of an Inhibitor from a Uridine-Based Library," *Antimicrobial Agents Chemother.* 47(1):378-382.

Soltero-Higgin et al. (Web Release Aug. 5, 2004) "Identification of Inhibitors for UDP-Galactopyranose Mutase," *J. Am. Chem. Soc.* 126(34):10532-10533.

Soltero-Higgin et al. (Web Release May 9, 2004) "A Unique Catalytic Mechanism for UDP-Galactopyranose Mutase," *Nat. Struct. Mol. Biol.* 11(6):539-543.

Tangallapally et al. (Web Release Sep. 3, 2004) "Synthesis and Evaluation of Nitrofuranylamides as Novel Antituberculosis Agents," *J. Med. Chem.* 47(21):5276-5283.

Veerrapen et al. (Sep. 13, 2004) "Synthesis of Novel Ammonium and Selenonium Ions and Their Evaluation as Inhibitors of UDP-Galactopyranose Mutase," *Carbohydr. Res.* 339(13):2205-2217.

\* cited by examiner

D32

D33

D34

D35

D36

D37

D38

D39

D40

D41

D42

104, each J is independently hydrogen, halo, nitro, C1-C3 alkyl

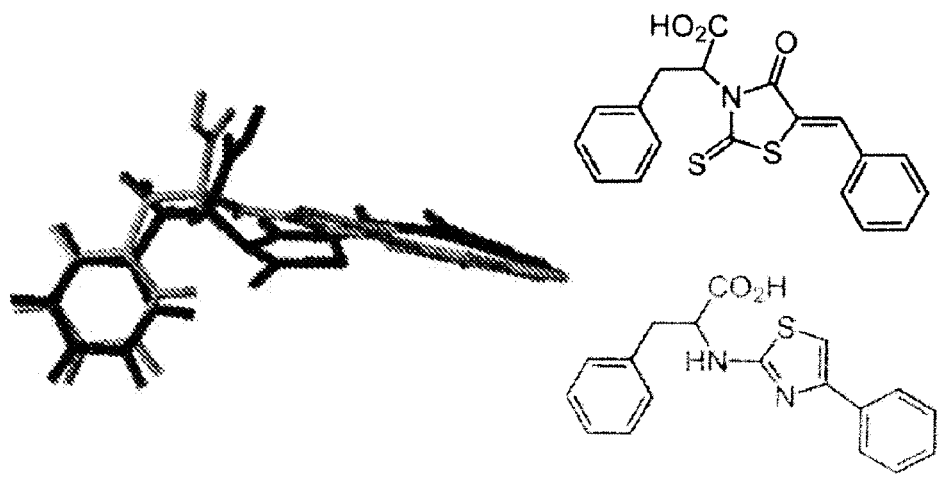
Fig. 3
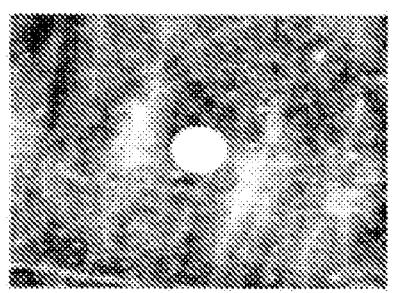
Control-DMSO
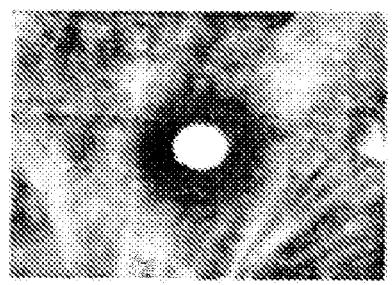
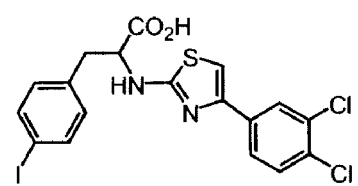
FIG. 4A
FIG. 4B

| | | | |
|---|---|---|---|
| 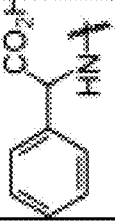 | K = 219 | K = 30<br>M = 115 | K = 127 |
|  | | K = 35 | |
|  | | | |
| 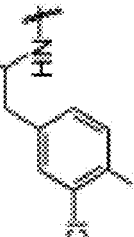 | | | |
|  | | | |
| 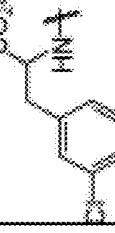 | K = 21<br>M = 42 | | K = 55 |
| | 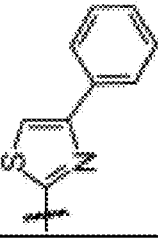 | 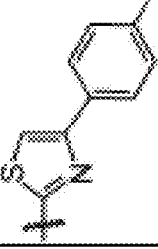 | 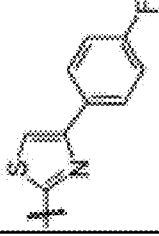 |
Fig. 6-3

FIG. 6-4

| | | | | |
|---|---|---|---|---|
| K = 72<br>M = 184 | K = 101<br>M = ? | K = 15<br>M = 53 | K = 15<br>M = 27 | K = 15<br>M = 119 |
| K = 156 | K = 122 | K = 22<br>M = 50 | K = 14<br>M = 32 | K = 23<br>M = 78 |
| | | | K = 12<br>M = 20 | |
| | | | K = 15<br>M = 15 | |
| | | K = 25<br>M = 281 | | |

FIG. 7-2

| | | | | |
|---|---|---|---|---|
| | | | | |
| K = 3<br>M = 20 | K = 4<br>M = 8 | K = 6<br>M = 12 | K = 4<br>M = 25 | K = 8<br>M = 7 |
| K = 5<br>M = 25 | | | | K = 5<br>M = 53 |
| | | | | |
| | | | | |

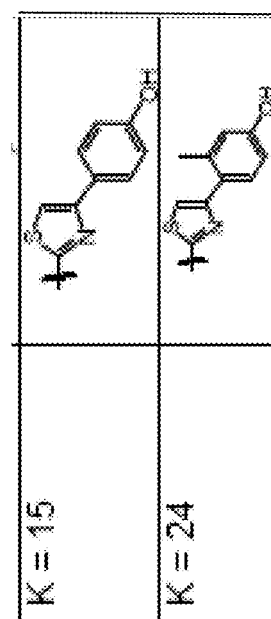
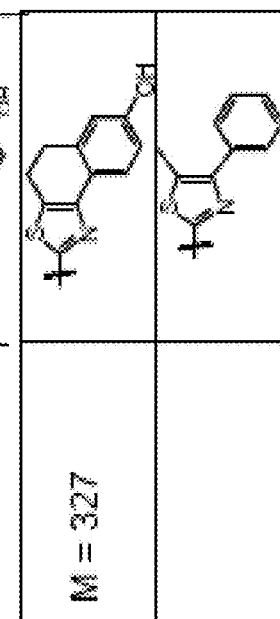
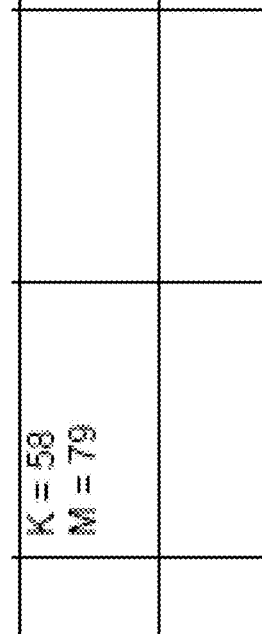
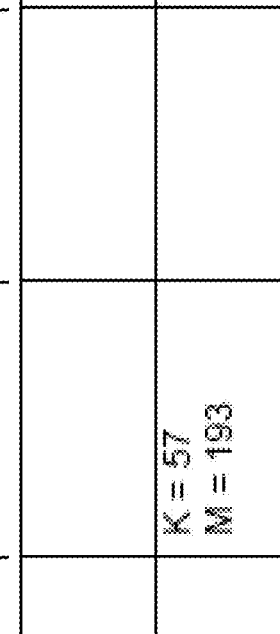
FIG. 7-4

$IC_{50} = 51 \; \mu M$ $IC_{50} = 37 \ \mu M$

| Compound | $K_d$ (μM) | Relative UGM$_{myco}$ activity at 50 μM | mycobacterial growth inhibition |
|---|---|---|---|
| DMSO | - | 1.00 | no |
| | > 300 | 1.00 | no |
| | > 300 | 0.96 | no |
| | > 300 | 0.95 | no |
| | 80 | 0.64 | yes |
| | 53 | 0.55 | yes |

FIG. 11-1

| | | | |
|---|---|---|---|
| (structure) | 12 | 0.48 | yes |
| (structure) | 7 | 0.45 | yes |
| (structure) | 29 | 0.36 | yes |
| (structure) | 32 | 0.33 | yes |
| (structure) | 13 | 0.25 | yes |

FIG. 11-2

| Compound | $K_d$ (μM) | Relative UGM$_{myco}$ activity at 50 μM | mycobacterial growth inhibition |
|---|---|---|---|
| 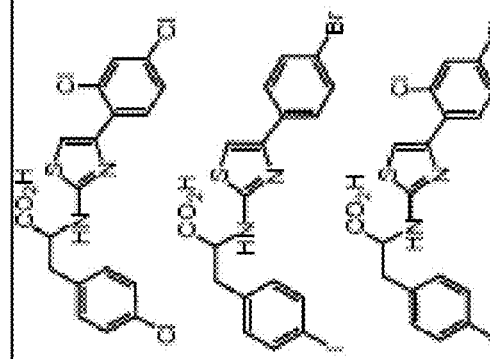 | 25 | 0.25 | yes |
| 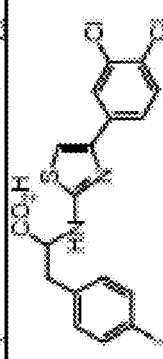 | 14 | 0.23 | yes |
| 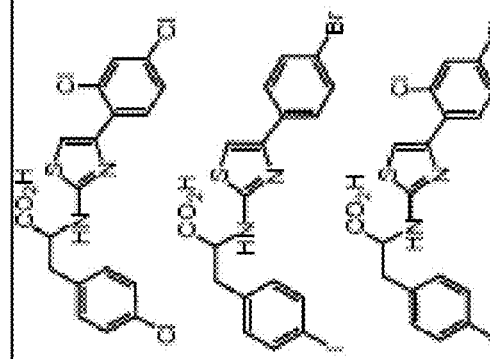 | 20 | 0.21 | yes |
| 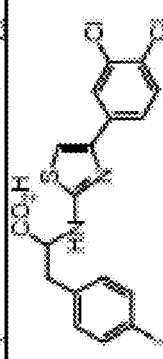 | 8 | 0.18 | yes |
FIG. 11-3

| Compound | $K_d$ (μM) | % inhibition of UGM$_{myco}$ activity at 50 μM inhibitor | MIC (μM) |
| --- | --- | --- | --- |
| (structure: thiazole-CN phenyl, benzyl) | >300 | 4 | >1000 |
| (structure: thiazole-3,5-difluorophenyl, 4-Cl-benzyl) | 53 | 45 | 210 |
| (structure: thiazole-4-F-phenyl, 4-Cl-benzyl) | 29 | 64 | 160 |
| (structure: thiazole-2,4-diCl-phenyl, 4-Cl-benzyl) | 25 | 75 | 80 |
| (structure: thiazole-3,4-diCl-phenyl, 4-I-benzyl) | 8 | 82 | 50 |

FIG. 12A

INHIBITORS OF UDP-GALACTOPYRANOSE MUTASE THWART MYCOBACTERIAL GROWTH

CROSS-REFERENCE TO RELATED APPLICATIONS

This application claims the benefit of U.S. provisional application Ser. No. 61/048,080, filed Apr. 25, 2008 which application is incorporated by reference in its entirety herein. This application also claims the benefit of International Application PCT/US09/41719, filed Apr. 24, 2009 which designates the United States and which in turn claims the benefit of U.S. provisional application No. 61/048,080, filed Apr. 25, 2008.

STATEMENT REGARDING GOVERNMENT SUPPORT

This invention was funded by the United States government through National Institutes of Health grant AI063596. The U.S. government has certain rights in this invention.

BACKGROUND OF THE INVENTION

Galactofuranose (Galf) residues are present in many pathogens. For example, they are essential components of the arabinogalactan layer of mycobacteria. Mycobacteria cause a number of diseases, the most deadly of these is tuberculosis (TB). Each year, *Mycobacterium tuberculosis* is responsible for 8 million human infections and 2 million deaths. (Tripathi, R. P.; Tewari, N.; Dwivedi, N.; Tiwari, V. K. Med. Res. Rev. 2005, 25, 93-131.) Strains have emerged that are resistant to most or all known antibiotics. (Marris, E. Nature 2006, 443, 131.) Resistance can be combated by developing an inhibitor with a new mechanism of action against a known target. (Sullivan, T. J.; Truglio, J. J.; Boyne, M. E.; Novichenok, P.; Zhang, X.; Stratton, C. F.; $L_1$, H. J.; Kaur, T.; Amin, A.; Johnson, F.; Slayden, R. A.; Kisker, C.; Tonge, P. J. ACS Chem. Biol. 2006, 1, 43-53.) An alternative approach is to identify novel targets. One such potential target is the essential enzyme responsible for the incorporation of galacto-furanose residues, uridine 5'-diphosphate (UDP) galactopyranose mutase (UGM). (Lowary, T. L. Curr. Opin. Chem. Biol. 2003, 7, 749-756.)

UGM uses a unique mechanism to catalyze the isomerization of UDP-galactopyranose (UDP-Galp) to UDP-galactofuranose (UDP-Galf) (Scheme 1, where U is uracil). (Soltero-Higgin, M.; Carlson, E. E.; Gruber, T. D.; Kiessling, L. L. Nat. Struct. Mol. Biol. 2004, 11, 539-543; Chad, J. M.; Sarathy, K. P.; Gruber, T. D.; Addala, E.; Kiessling, L. L.; Sanders, D. A. R. Biochemistry 2007, 46, 6723-6732.) Since UGM is not a target of other tuberculosis drugs, compounds that block UGM are expected to be effective against drug resistant strains.

Scheme 1

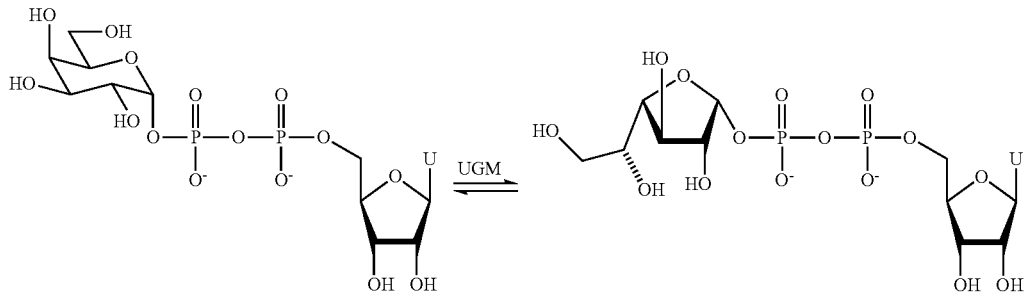

The gene encoding UGM is essential for mycobacterial viability; the identification of UGM inhibitors can validate it as a therapeutic target. (Pan, F.; Jackson, M.; Ma, Y. F.; McNeil, M. J. Bacteriol. 2001, 183, 3991-3998.) Moreover, Galf residues are also found in some eukaryotes, including a number of pathogenic (to humans and animals) eukaryotes, therefore, UGM inhibitors can also provide insight into the role of Galf-containing oligosaccharides in these organisms. (Beverley, S. M.; Owens, K. L.; Showalter, M.; Griffith, C. L.; Doering, T. L.; Jones, V. C.; McNeil, M. R. Eukaryotic Cell 2005, 4, 1147-1154.) Additionally, there is no enzyme comparable to UGM in humans or other mammals increasing the appeal of UGM inhibitors as useful therapeutics.

Most efforts to develop UGM inhibitors have focused on UDP-sugar substrate analogs. (Caravano, A.; Dohi, H.; Sinay, P.; Vincent, S. P. Chem.-Eur. J. 2006, 12, 3114-3123; Liautard, V.; Christina, A. E.; Desvergnes, V.; Martin, O. R. J. Org. Chem. 2006, 71, 7337-7345; Ghavami, A.; Chen, J. J. W.; Pinto, B. M. Carbohydr. Res. 2004, 339, 401-407; Lee, R. E.; Smith, M. D.; Pickering, L.; Fleet, G. W. J. Tetrahedron Lett. 1999, 40, 8689-8692; Liautard, V.; Desvergnes, V.; Martin, O. R. Org. Lett. 2006, 8, 1299-1302.) Simple sugar derivatives, including galactopyranose or galactofuranose analogs, bind weakly with affinities in the millimolar range (Lee, R. E.; Smith, M. D.; Nash, R. J.; Griffiths, R. C.; McNeil, M.; Grewal, R. K.; Yan, W. X.; Besra, G. S.; Brennan, P. J.; Fleet, G. W. J. Tetrahedron Lett. 1997, 38, 6733-6736; Veerapen, N.; Yuan, Y.; Sanders, D. A. R.; Pinto, B. M. Carbohydr. Res. 2004, 339, 2205-2217.) Inhibitors that incorporate the uridine portion of the substrate bind substantially better, with affinities that approximate that of UDP-Galp ($K_d$=52 µM) (Itoh, K.; Huang, Z. S.; Liu, H. W. Org. Lett. 2007, 9, 879-882; Caravano, A.; Vincent, S. P.; Sinay, P. Chem. Commun. 2004, 1216-1217; Caravano, A.; Mengin-Lecreulx, D.; Brondello, J. M.; Vincent, S. P.; Sinay, P. Chem.-Eur. J. 2003, 9, 5888-5898; Pan, W. D.; Ansiaux, C.; Vincent, S. P. Tetrahedron Lett. 2007, 48, 4353-4356; Scherman, M. S.; Winans, K. A.; Stern, R. J.; Jones, V.; Bertozzi, C. R.; McNeil, M. R. Antimicrob. Agents Chemother. 2003, 47, 378-382.) These approaches have not yet afforded compounds that block mycobacterial growth.

Certain non-substrate based molecules have been identified as UMG ligands. For example, certain nitrofuranylamides have been identified as inhibitors of UGM catalysis and mycobacterial growth. (Tangallapally, R. P.; Yendapally, R.; Lee, R. E.; Hevener, K.; Jones, V. C.; Lenaerts, A. J. M.; McNeil, M. R.; Wang, Y. H.; Franzblau, S.; Lee, R. E. *J. Med. Chem.* 2004, 47, 5276-5283.) Nevertheless, the UGM inhibition and antimycobacterial activity of these compounds were not correlated, so they do not address the utility of inhibiting UGM.

A high-throughput, fluorescence polarization (FP) screen was reported to identify several compounds (including 1A-4A below) with good $IC_{50}$ values ($\sim 10^{-6}$ M) for the UGM from *Klebsiella pneumoniae* ($UGM_{kleb}$) or *M. tuberculosis* ($UGM_{myco}$). (Soltero-Higgin, M.; Carlson, E. E.; Phillips, J. H.; Kiessling, L. L. *J. Am. Chem. Soc.* 2004, 126, 10532-10533.)

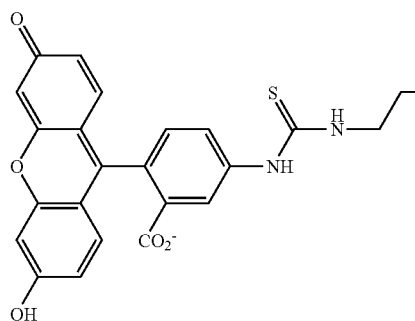

1A

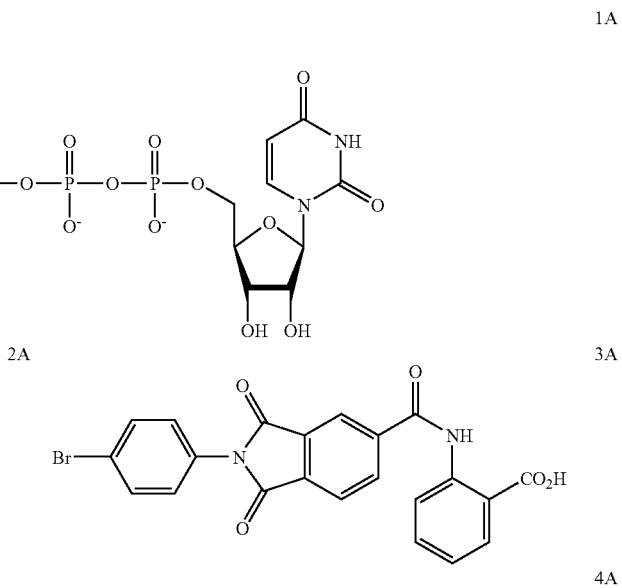

2A

3A

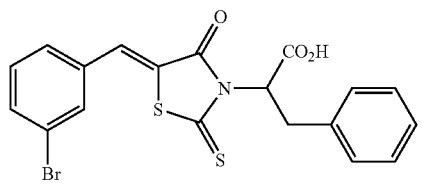

4A

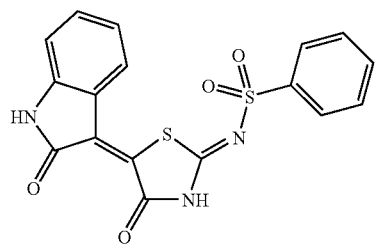

Published International application WO 2005/007625 (Lee et al.), as well as published U.S. application 20050222408, relate to certain heterocyclic amides with anti-tuberculosis activity. More specifically, these patent documents relate to compounds of formula:

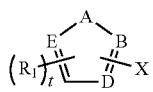

wherein A is selected from the group consisting of oxygen, sulfur, and $NR_{15}$, and $R_{15}$ is selected from the group consisting of H, alkyl, aryl, substituted alkyl, and substituted aryl; B, D, and E are each independently selected from the group consisting of CH, nitrogen, sulfur and oxygen; $R_1$ is selected from the group consisting of nitro, halo, alkyl ester, arylsulfanyl, arylsulfinyl, arylsulfonyl and sulfonic acid; t is an integer from 1 to 3; and X is a substituted amide. These patent documents are incorporated by reference herein at least in part for the definitions of structural elements of the above formula.

A directed library containing a 5-arylidine-2-thioxo-4-thiazolidinone core has been reported to identify factors influencing UGM ligand binding. (Carlson, E. E.; May, J. F.; Kiessling, L. L. *Chem. Biol.* 2006, 13, 825-837.) Several thiazolidinone derivatives were reported to be ligands for both the $UGM_{kleb}$ and $UGM_{myco}$ homologs. The thiazolidinone scaffold, however, reacts reversibly with biologically relevant thiols in solution. Not surprisingly, inhibitors of this structural class were reported to fail to block mycobacterial growth.

There remains a need in the art for small molecules that exhibit antimicrobial activity, particularly against *Mycobacteria*.

SUMMARY OF THE INVENTION

The present invention provides compounds which inhibit microbial growth or attenuate the virulence of pathogen microorganisms. In certain embodiments, compounds of the invention inhibit UDP-galactopyranose mutase (UGM) and have activity as inhibitors of microbial growth of microorganisms which contain this enzyme and particularly those microorganisms in which this enzyme is responsible for the incorporation of galactofuranose residues, particularly for uridine 5'-diphosphate (UDP) galactopyranose mutase. In certain embodiments, compounds of the invention inhibit UDP-galactopyranose mutase (UGM) and have activity to attenuate virulence of pathogenic microorganisms which contain this enzyme and particularly those microorganisms in which this enzyme is responsible for the incorporation of galactofuranose residues.

More specifically, the inhibitors of UGM of this invention inhibit growth or attenuate virulence of microbial pathogens including mycobacterium, for example, *M. tuberculosis* and *M. smegmatis* and *Klebsiella*, for example, *Klebsiella pneumoniae*. Additionally, UGM inhibitors of this invention can also inhibit UGM of certain eukaryotic human and animal pathogens. Compounds of this invention are useful for treatment of infections by prokaryotic and eukaryotic pathogens. Compounds of this invention are useful in human and veterinary treatment applications. Compounds of this invention are useful for the treatment of tuberculosis. Compounds of this invention are useful in combination therapy with other antibiotics for the treatment of microbial infections, including tuberculosis. Compounds of this invention are useful for the treatment of multiple drug resistant microbial infections, including multiple drug resistant tuberculosis.

The invention provides compounds of formula I:

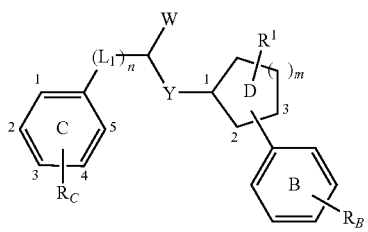

and salts thereof, where: n is 0 or 1 to indicate the presence or absence of $L_1$;
$L_1$, if present, is an alkylene, alkenylene or alkyleneoxy linker having 1-6 carbon atoms;

Y is $CH_2$ or $NR_Y$, where $R_Y$ is hydrogen or a C1-C6 alkyl;

W is —$COOR_W$, —O—$COR_W$, —$CON(R_W)_2$, —$OCON(R_W)_2$, —$SO_2$—$OR_W$, —$SO_2$—$N(R_W)_2$, —$OPO_3R_W$, —$OP(OR_W)_2R_W$, or a tetrazolyl group, where each $R_W$, independent of other $R_W$, is hydrogen, C1-C6 alkyl or an aryl or heteroaryl group having one or two 5-member or 6-member rings;

the D ring is a 1,3- or 1,2-substituted 5-member (when m is 1) or 6-member ring (when m is 2), which is a carbocyclic or heterocyclic ring, including a heteroaryl, or an aryl group, where the 1, 2 and 3 ring positions are as indicated above;

$R^1$ represents no substitution on the D ring (where $R^1$ are all hydrogens) or substitution with one or more C1-C3 alky, one or more C1-C3 haloalkyl (including trihalomethyl groups), one or more halogens or combinations thereof;

the B and C rings are independently selected from an aryl or heteroaryl group having one or two rings;

$R_B$ and $R_C$ represent no substitution on the indicated ring or substitution on that ring by one to five non-hydrogen substituents selected from the group consisting of halogen, nitro, cyano, hydroxyl, C1-C6 alkyl, C1-C6 alkoxy, sulfonamide (—$SO_2$—$N(R_F)_2$), azide, sulfonyl (—$SO_2$—$R_F$), —$COOR_F$, —O—$COR_F$, —$COR_F$, —$CON(R_F)_2$, —O—$CON(R_F)_2$, —$N(R_F)_2$, and C1-C6 haloalkyl groups, including trifluoromethyl, trichloromethyl and tribromomethyl groups, where $R_F$ is hydrogen or a C1-C6 alkyl group;

or wherein substituents on two adjacent carbons of a B or C ring together form a carbocyclic or heterocyclic ring having 5 to 8 ring atoms and optionally wherein one or two of the ring members are heteroatoms, particularly N, O or S, which 5- to 8-member ring may be an aromatic ring, or $R_B$ is -M-$L_2$-Q-AR where:

AR is an aryl or heteroaryl group having at least two rings;

$L_2$ is a linker group which can be an alkylene, cycloalkylene, alkenylene or alkyleneoxy group, which contains 5-12 carbon atoms, or a 5- or 6-member heterocyclene group, containing one or two O, N or S atoms or combinations thereof, a 6-member ring arylene or a 6-member ring heteroarylene group, containing one or two O, N or S atoms or combinations thereof;

M and Q are chemical moieties that function to covalently link L between the B ring and AR, M and Q can independently be selected from, —O—, —S—, —CO—, —$NR_M$—, (where $R_M$ is hydrogen or C1-C6 alkyl), carboxyl, amide, sulfonamide, thiourea, urea, carbonate, guanidinium, carbamate, thiocarbamate, alkylene moieties or combinations thereof. In the above formula the numbering of the carbons on the B and C rings is indicated.

In specific embodiments, $L_2$ is —$(CH_2)_a$—, —$CH_2$—$(CH_2$—O—$CH_2)_b$—$CH_2$—, or [—$(CH_2)_c$—O—]$_e$—$(CH_2)_d$—, where a, independently, is an integer ranging from 3-12 and more preferably ranges from 5-12 and more preferably ranges from 6-10, b, independently, is an integer ranging from 1-4 and more preferably 1, 2 or 3, c, independently, is an integer ranging from 1-6, and preferably 1-4, d, independently, is an integer ranging from 1-6 and preferably 2-4 and e, independently, is an integer ranging from 1 to 4 and preferably 2 or 3. In other embodiments, $L_2$ is a cyclohexylene group, or a —$(CH_2)_f$-cyclo-$C_6H_{10}$—$(CH_2)_g$— group, where f and g, independently are integers, from 1-6. In other embodiments, $L_2$ is a 5- or 6-member heterocyclene group, containing one or two O, N or S atoms or combinations thereof, a 6-member ring arylene or a 5- or 6-member ring heteroarylene group, containing one or two O, N or S atoms or combinations thereof and M and Q are alkylene groups.

In specific embodiments, W is —COOH. In specific embodiments, W is —$CON(H)_2$. In specific embodiments, W is —$SO_2$—OH. In specific embodiments, W is —$SO_2$—$N(H)_2$. In specific embodiments, W is —$OPO_3H$. In specific embodiments, W is, —$OP(OH)_2H$ or —$OP(OR)_2H$, where R is an alkyl group. In specific embodiments, W is a tetrazol-1-yl group.

In an embodiment, the invention provides compounds of formula II:

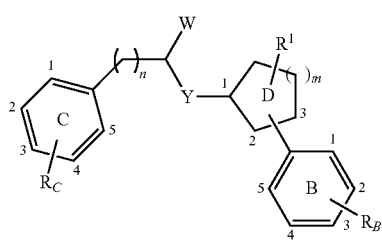

and salts thereof, where n is 0 or 1;

Y is $CH_2$ or $NR_Y$ where $R_Y$ is hydrogen or a C1-C6 alkyl;

W is —COOR$_W$, —O—CO—R$_W$, —CON(R$_W$)$_2$, —O—CON(R$_W$)$_2$, —SO$_2$—OR$_W$, —SO$_2$—N(R$_W$)$_2$, —OPO$_3$R$_W$, —OP(OR$_W$)$_2$R$_W$, or tetrazolyl, where each R$_W$, independent of other R$_W$, is hydrogen, C1-C6 alkyl or an aryl or heteroaryl group having one 5 or 6-member ring;

the D ring is a 1,3- or 1,2-substituted 5-member (m is 1) or 6-member ring (m is 2) which is carbocyclic or heterocyclic, including heteroaryl, and aryl groups, where the 1, 2 and 3 ring positions are as indicated above; R$^1$ represents no substitution on the D ring (R$^1$ all hydrogen) or substitution with one or more C1-C3 alky, C1-C3 haloalkyl (including trihalomethyl groups) or halogens;

the B and C rings are independently selected from an aryl or heteroaryl group having one or two rings;

R$_B$ and R$_C$ represents no substitution on the indicated ring or substitution on that ring by one to five non-hydrogen substituents selected from the group consisting of halogen, nitro, cyano, hydroxyl, C1-C6 alkyl, C1-C6 alkoxy, sulfonamide (—SO$_2$—N(R$_F$)$_2$), azide, sulfonyl (—SO$_2$—R$_F$), —COOR$_F$, —COR$_F$, —OCOR$_F$, —CON(R$_F$)$_2$, —O—CON(R$_F$)$_2$, —N(R$_F$)$_2$, and C1-C6 haloalkyl groups, including trifluoromethyl, trichloromethyl and tribromomethyl groups, where R$_F$ is hydrogen or a C1-C6 alkyl group;

or wherein substituents on two adjacent carbons of a B or C ring together form a carbocyclic or heterocyclic ring containing having 5-8 members and optionally containing one or two heteroatoms, particularly N, O or S, which 5-8 member ring may be an aromatic ring or R$_B$ includes the group:

-M-L$_2$-Q-AR where:

AR is an aryl or heteroaryl group having at least two rings;

L$_2$ is a hydrophobic linker group ranging in length from 5-12 atoms (preferably 6-10 atoms), which can be —(CH$_2$)$_a$—, —CH$_2$—(CH$_2$—O—CH$_2$)$_b$—CH$_2$—, where a is an integer ranging from 5-12 and preferably ranges from 6-10 and b is 2-4, a cyclohexyl group, a 6-member heterocyclic group containing one or two O, N or S groups, or a 6-member ring aryl or a 6-member ring heteroaryl group;

M and Q are chemical moieties that function to covalently link L$_2$ between the B ring and AR, M and Q can independently be selected from, —O—, —S—, —CO—, —NR$_M$—, where R$_M$ is hydrogen or C1-C6 alkyl, carboxyl, amide, sulfonamide, thiourea, urea, carbonate, guanidinium, carbamate, and thiocarbamate moieties. In the above formula the numbering of the carbons on the B and C rings is indicated.

Exemplary D rings for formulas herein are illustrated in FIGS. 1A, 1B and 1C which follow, in which each R$^1$, independently, is hydrogen, C1-C3 alkyl, C1-C3-haloalkyl or halogen and R$_D$ is hydrogen or a C1-C6 alkyl.

In specific embodiments, both the B and C rings are optionally substituted phenyl rings. In specific embodiments, the B or the C ring can be selected from heteroaryl 6-member rings. In specific embodiments, the B or C ring has one or two 5- or 6-member rings. In specific embodiments, the B and C rings can be selected from pyridyl, indolyl, purinyl, pyrazinyl, pyrimidinyl, thienyl, benzofuranyl, naphthyl or benzothienyl rings.

In a specific embodiment, there is at least one non-hydrogen substituent on the B ring or C ring. In a specific embodiment, there is at least one non-hydrogen substituent on each of the B and C rings.

D rings are preferably substituted at the 1 and 3 positions as those positions are numbered in Formula II and may have one or two additional substituents R$^1$. D ring groups include, among others, phenyl, thiazolyl, oxazolyl, imidazolyl, pyrazolyl, pyrrolyl, pyridyl, pyridazinyl, pyrimidinyl, thienyl (thiophenyl), furanyl, isoxazolyl, isothiazolyl, or tetrazolyl, including various isomers thereof.

In specific embodiments, AR has from two to four 5 or 6-member rings. AR groups include, among others, optionally substituted benzophenonyl, naphthalenyl, benzofuranyl, benzothienyl, indolyl, xanthenyl, purinyl, quinolyl, biphenyl, phenylxanthenyl, acridinyl, phenazinyl, phenoxazinyl, phenothiazinyl, carbazolyl, and naphthyridinyl. In specific embodiments, AR groups include, among others, non-substituted benzophenonyl, naphthalenyl, benzofuranyl, benzothienyl, indolyl, xanthenyl, purinyl, quinolyl, biphenyl, phenylxanthenyl, acridinyl, phenazinyl, phenoxazinyl, phenothiazinyl, carbazolyl, or naphthyridinyl groups, including various isomers thereof.

In specific embodiments, W is —COOH. In specific embodiments, W is —CON(H)$_2$. In specific embodiments, W is —SO$_2$—OH. In specific embodiments, W is —SO$_2$—N(H)$_2$. In specific embodiments, W is —OPO$_3$H. In specific embodiments, W is, —OP(OH)$_2$H or —OP(OR)$_2$H, where R is an alkyl group. In specific embodiments, W is a tetrazol-1-yl group.

In specific embodiments, M and Q are selected from —NR$_M$—, —O— or a thiourea moiety. In specific embodiments, L$_2$ is an alkenylene, —(CH$_2$)$_a$— as defined above and in a more specific embodiment, a is 6, 7, 8 or 9.

In specific embodiments, AR groups are dyes including various fluorescein dye groups, eosin dye groups, erthrosin dye groups, rhodamine dye groups, bodipyl dye groups, or alexafluor 488 dye groups. In these embodiments, the compound containing the AR dye group is formed by forming a covalent bond to a dye molecule. Typically, such groups are formed by reaction of a dye molecule containing a reactive functional group (e.g., an isothiocyanate group). In specific embodiments, where AR is a dye, the Q moiety is the group that results on reaction of the functional group on the dye with a compatible reactive group on the linker. See Example 2 for specific examples. In specific examples, AR is a structure in FIG. 2A or 2B.

In a specific embodiment, the substituent on the B ring is the -M-L-Q-AR group at the 3-position.

In a specific embodiment there is at least one non-hydrogen substituent on each of the B and C ring. In specific examples, there is one substituent on the C ring and at least one substituent on the B ring. In specific examples, there is 0 or 1 substituent on the C ring and the substituent on the B ring is the -M-L-Q-AR group at the 3-position.

In specific embodiments, the UGM inhibitors are compounds of formulas IVA, IVB, IVC, IVD, IVE or IVF:

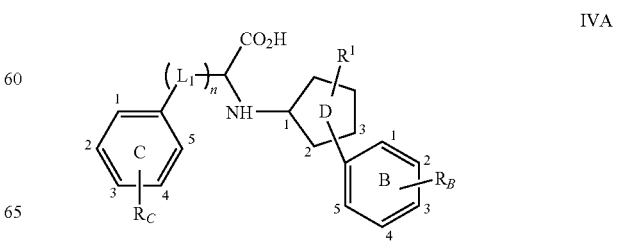

IVA

-continued

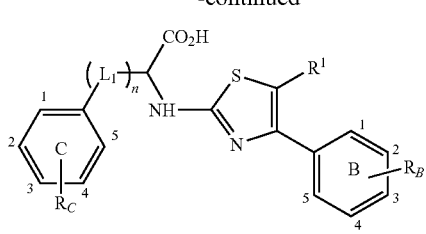
IVB

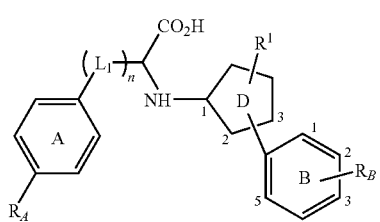
IVC

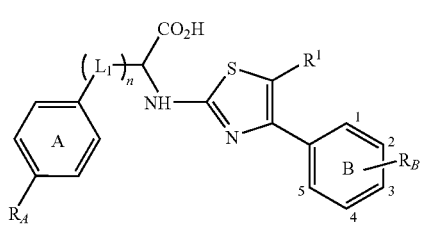
IVD

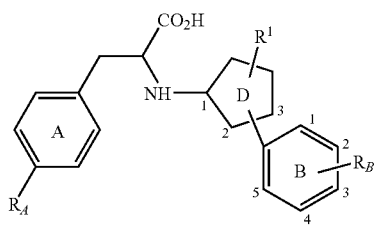
IVE

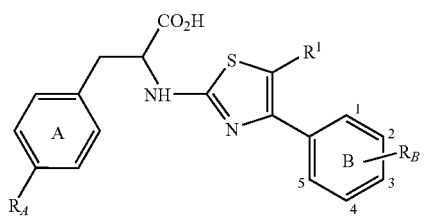
IVF and salts thereof,
where $L_1$, n, $R_C$, $R^1$ and Rings B, C and D are defined above;
the A ring is a 6-member aryl or heteroaryl ring having one, two or three nitrogens; and
each $R_A$ is a hydrogen, halogen, nitro, cyano, hydroxyl, C1-C6 alkyl, C1-C6 alkoxy, sulfonamide ($-SO_2-N(R_F)_2$), azide, sulfonyl ($-SO_2-R_F$), $-COOR_F$, $-COR_F$, $-CON(R_F)_2$, $-O-CON(R_F)_2$, $-N(R_F)_2$, or C1-C6 haloalkyl groups, including trifluoromethyl, trichloromethyl and tribromomethyl groups, where $R_F$ is hydrogen or a C1-C6 alkyl group, and $R_B$ represents no substitution on the indicated B ring or substitution on the B ring by one to five non-hydrogen substituents selected from the group consisting of halogen, nitro, cyano, hydroxyl, C1-C6 alkyl, C1-C6 alkoxy, sulfonamide ($-SO_2-N(R_F)_2$), azide, sulfonyl ($-SO_2-R_F$), $-COOR_F$, $-COR_F$, $-OCR_F$, $-CON(R_F)_2$, $-O-CON(R_F)_2$, $-N(R_F)_2$, and C1-C6 alkylhalide groups, including trifluoromethyl, trichloromethyl and tribromomethyl groups, where $R_F$ is hydrogen or a C1-C6 alkyl group or wherein substituents on two adjacent carbons of the phenyl ring together form a carbocyclic or heterocyclic ring containing having 5-8 members and optionally containing one or two heteroatoms which 5-8 member ring may be an aromatic ring or where $R^1$ and one substituent on the B ring are linked together to form a 5-8 member carbocyclic or heterocyclic ring which may be an aromatic ring. The numbers of the carbons on the B ring are indicated.

In a specific embodiment n is 1. In a specific embodiment, $L_1$ is an alkeneylene having one double bond.

In a specific embodiment, the D ring is one of D1-D42.

In a specific embodiment, there is at least one non-hydrogen substituent on either the C or B ring. In another embodiment, there is at least one non-hydrogen substituent on each of the C and B rings.

In a specific embodiment, there is at least one non-hydrogen substituent on either the A or B ring. In another embodiment, there is at least one non-hydrogen substituent on each of the A and B ring. In a specific embodiment, the A ring is a phenyl ring.

In another embodiment, the invention provides compounds of formula VA, VB, VC or VD:

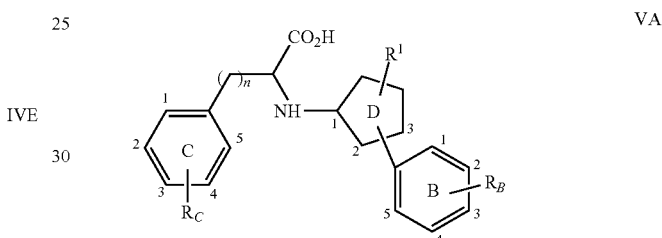
VA

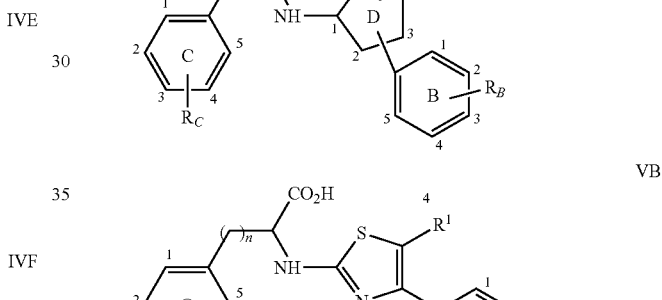
VB

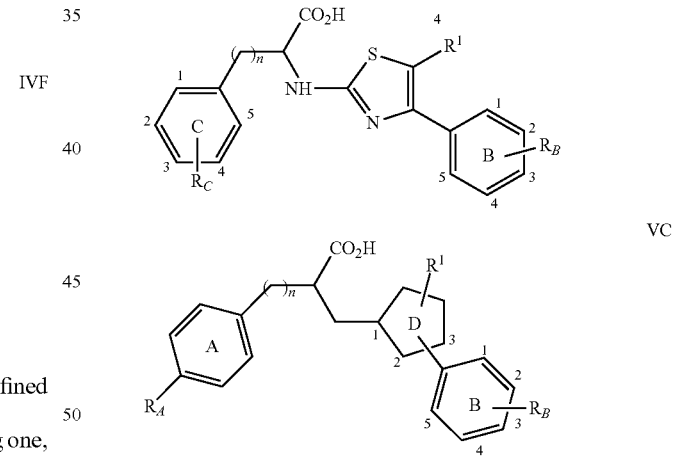
VC

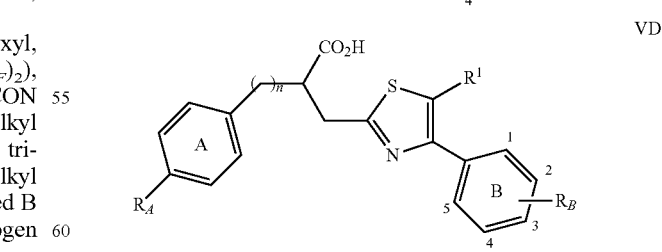
VD and salts thereof,
where variables are as defined for formulas I-IV above and n is 0 or 1.

In specific embodiments of formulas VA and VB, the C ring is a phenyl ring. In specific embodiments of formulas VA and VB, the B ring is a phenyl ring. In specific embodiments of formulas VA and VB, both the C and B rings are phenyl rings. In specific embodiments of formulas VA and VB, when the C ring is a phenyl ring and when n is 0, then $R_C$ is a non-hydrogen substituent and there is at least one non-hydrogen substituent on the B ring and when n is 1 there is at least one non-hydrogen substituent on either the C or B ring.

In specific embodiments of formulas VC and VD, the A ring is a phenyl ring. In specific embodiments of formulas VC and VD, the B ring is a phenyl ring. In specific embodiments of formulas VC and VD, both the A and B rings are phenyl rings. In specific embodiments of formulas VC and VD, when A is a phenyl ring and when n is 0 then $R_A$ is a non-hydrogen substituent and there is at least one non-hydrogen substituent on the B ring and when n is 1 there is at least one non-hydrogen substituent on either the A or B ring.

In another embodiment, the invention provides compounds of formula VIA and VIB:

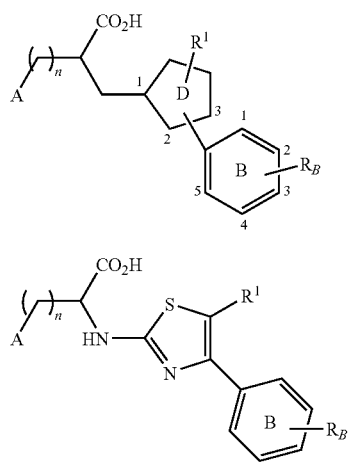

and salts thereof, where D, n, $R^1$ and $R_B$ are as defined above for formulas I-V above and A is an optionally substituted aryl or optionally substituted heteroaryl group having one or two rings, wherein optional substitution is substitution with one or more of halogen, nitro, cyano, hydroxyl, C1-C6 alkyl, C1-C6 alkoxy, sulfonamide ($-SO_2-N(R_F)_2$), azide, sulfonyl ($-SO_2-R_F$), $-CO-OR_F$, $-COR_F$, $-O-COR_F$, $-CON(R_F)_2$, $-O-CON(R_F)_2$, $-N(R_F)_2$, and C1-C6 haloalkyl groups, including trifluoromethyl, trichloromethyl and tribromomethyl groups, where $R_F$ is hydrogen or a C1-C6 alkyl group, wherein: when n is 0, A is an optionally substituted heteroaryl group or A is a phenyl group having the structure:

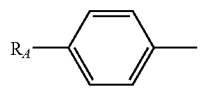

where $R_A$ is as defined above or when n is 1, A is an optionally substituted phenyl or heteroaryl group.

In specific embodiments of formulas VIA or VIB, ring B is a phenyl ring. In specific embodiments of formulas VIA or VIB, A is an optionally substituted phenyl ring and ring B is a phenyl ring. In specific embodiments of formulas VIA or VIB, A is an optionally substituted naphthyl group. In specific embodiments of formulas VIA or VIB, A is an optionally substituted naphthyl group and the B ring is a phenyl ring.

In another embodiment the invention provides compounds of formula VIIA and VIIB:

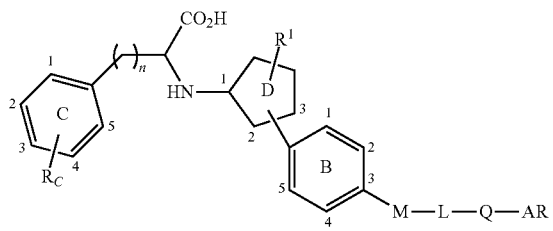

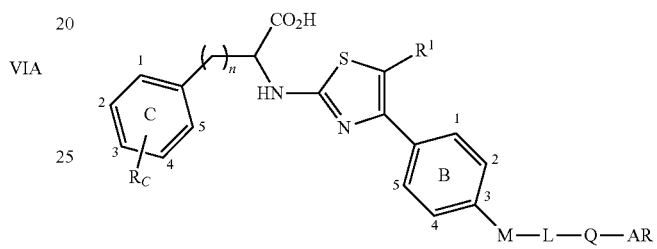

where variables are as defined above.

In specific embodiments of formulas VIIA/B, Q is thiourea, and M is O or $NR_M$. In specific embodiments of formulas VIIA/B, AR is a dye group, particularly a fluorescein dye group. In specific embodiments of formulas VIIA/B, AR is optionally substituted naphthyl. In specific embodiments of formulas VIIA/B, the B ring is a phenyl ring. In specific embodiments of formulas VIIA/B, the C ring is a phenyl ring. In specific embodiments of formulas VIIIA/B, $R_C$ represents substitution with a single non-hydrogen substituent at the 3 position. In specific embodiments, n is 1. In specific embodiments of formulas VIIA/B, $R^1$ is hydrogen.

In additional embodiments, the invention provides compounds of formula I or II wherein $R_B$ is $-M-L_2-Q-AR$ and AR is selected from AR groups 100-104 or 200-204. Also provided are compounds of formula I and II where AR is

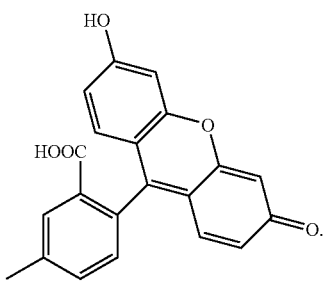

In additional embodiments, the invention provides compounds of formula I or II wherein $R_B$ represents two or more substituents on the B ring, one of which is $-M-L_2-Q-AR$.

In additional embodiments, the invention provides compounds of formula X:

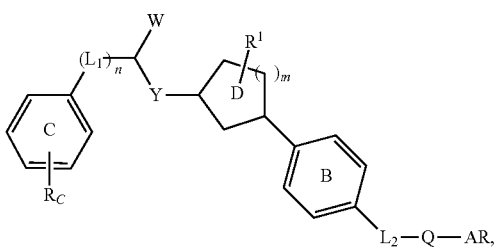

where variable are as defined above.

In additional embodiments, the invention provides compounds of formula XI:

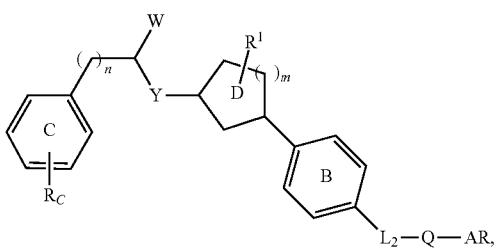

where variables are as defined above and n is 0 or 1.

In additional embodiments, the invention provides compounds of formula XII:

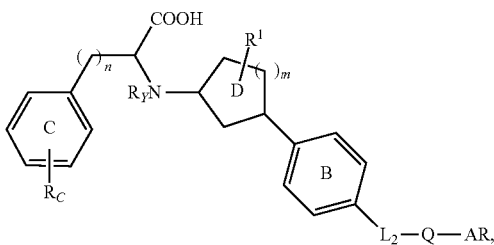

where variables are as defined above.

In additional embodiments, the invention provides compounds of formula XIII:

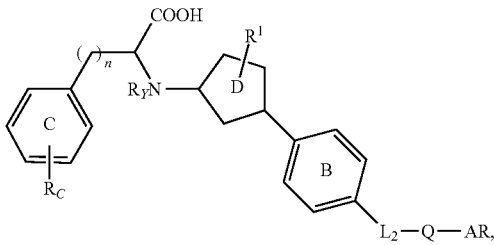

where variables are as defined above.

In additional embodiments, the invention provides compounds of formula XIV:

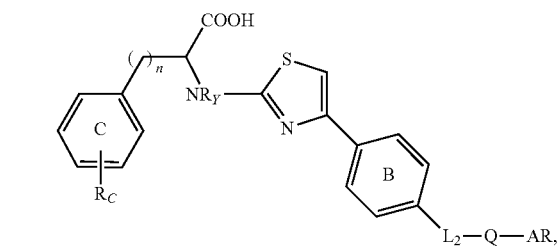

where variables are as defined above.

In specific embodiments of formulas X-XIV, the B ring and the C ring are phenyl rings. In specific embodiments of formulas X-XIV, AR is an optionally substituted naphthyl group. In specific embodiments of formulas X-XIV, AR is an unsubstituted naphthyl group. In specific embodiments of formulas X-XIV, AR is an AR group selected from groups 100-104 or 200-204 (FIGS. 2A and 2B). In specific embodiments of formulas X-XIV, AR is

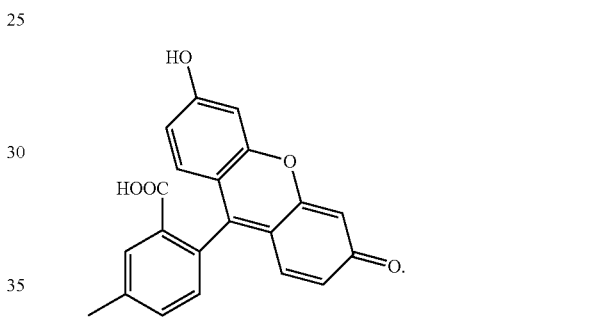

In specific embodiments of formulas X-XIV, Q is a thiourea or urea. In other specific embodiments of formulas X-XIV, Q is thiourea and AR is

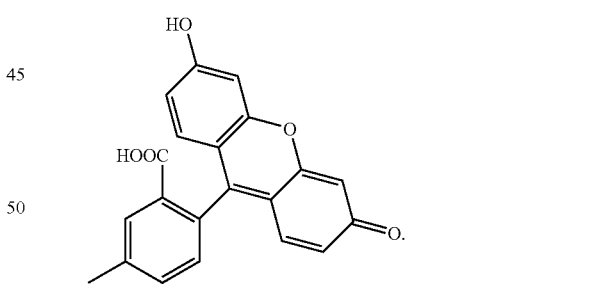

The invention further provides a method for inhibiting UGM in vitro or in vivo by contacting a biological composition comprising an active UGM with an amount of one or more of the compounds of any of the formulas herein effective for inhibiting UGM. In a specific embodiment, the inhibition of UGM is in vivo in a prokaryote. In a specific embodiment, the inhibition of UGM is in vivo in a eukaryote.

The invention also provides a method for inhibiting the growth of a microorganism containing UGM by contacting the microorganism with an amount of one or more of the compounds of any of the formulas herein effective for inhibiting the growth of the microorganism. In a specific embodiment the microorganism is a human or veterinary pathogen.

In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. The microorganism can be a prokaryote or a eukaryote.

The invention also provides a method for attenuating the virulence of a microorganism containing UGM by contacting the microorganism with an amount of one or more of the compounds of any of the formulas herein effective for attenuating virulence of the microorganism. In a specific embodiment the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. The microorganism can be a prokaryote or a eukaryote.

The invention also provides a method for inhibiting the growth of a microorganism containing UGM by contacting the microorganism with an amount of one or more of the compounds of any of the formulas herein effective for inhibiting UGM. In a specific embodiment the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. The microorganism can be a prokaryote or a eukaryote.

The invention further provides a method of treating a human, a non-human mammal or a non-human animal individual having or believed to have an infection of a microorganism containing UGM by administering to the individual an amount of one or more compounds of any of the formulas herein effective for inhibiting the growth of the microorganism. In specific embodiments, the microorganism is a bacterium or a mycobacterium. In specific embodiments, the mycobacterial infection is tuberculosis. In specific embodiments, the microorganism is of the genus *Mycobacterium* or *Klebsiella*. In additional embodiments, the microorganism is *Mycobacterium tuberculosis*, *Mycobacterium smegmatis* or *Klebsiella pneumoniae*. The pathogenic microorganism can be a prokaryote or a eukaryote.

The invention additionally provides a method for treating a human, a non-human mammal or a non-human animal individual having or believed to have an infection of a microorganism containing UGM by administering an effective amount of a compound of this invention of any of the formulas herein, in combination with an antibiotic appropriate for treatment of the infection. Compounds of this invention can enhance the effectiveness of art-known antibiotics and are useful in combination therapy in addition to such antibiotics.

The compounds of the present invention can, for example, be employed in combination therapy with antibiotics, such as ethambutol, isoniazid, rifampicin, and pyrazinamide. Such combination therapy is particularly useful in the treatment of mycobacterial infections.

The invention additional provides a medicament comprising one or more compounds of the formulas herein effective for inhibiting the growth of a microorganism or effective for attenuating the virulence of a microorganism which contains UGM. The invention additional provides a medicament comprising one or more compounds of any of the formulas herein effective for inhibiting UGM. In specific embodiments, the microorganism is a bacterium or a mycobacterium. In specific embodiments, the microorganism is of the genus *Mycobacterium* or *Klebsiella*. In additional embodiments, the microorganism is *Mycobacterium tuberculosis*, *Mycobacterium smegmatis* or *Klebsiella pneumoniae*.

The invention also provides a method of making a medicament for treating an individual (human, mammal or animal) having a bacterial or mycobacterial infection. In specific embodiments, the mycobacterial infection is tuberculosis. In specific embodiments, the microorganism is of the genus *Mycobacterium* or *Klebsiella*. In additional embodiments, the microorganism is *Mycobacterium tuberculosis*, *Mycobacterium smegmatis* or *Klebsiella pneumoniae*. In a specific embodiment, the method of making a medicament includes the step of combining an amount of a compound of any of the formulas herein with a pharmaceutically effective carrier. In a specific embodiment, the medicament is in a dosage form appropriate for oral administration, topical administration or administration by injection.

The invention also provides method for screening a small molecule library for members which inhibit the growth of a microorganism having UGM which comprises the step of identifying those member of the library which exhibit a dissociation constant K for the UGM enzyme of 100 µM or less. In another embodiment, the member is identified as exhibiting a dissociation constant K for the UGM enzyme of 50 µM or less. In another embodiment, the member is identified as exhibiting a dissociation constant K for the UGM enzyme of 25 µM or less. In another embodiment, the member is identified as exhibiting a dissociation constant K for the UGM enzyme of 10 µM or less. In further embodiments, the microorganism is a mycobacterium, particularly *Mycobacterium tuberculosis*. In additional embodiments the microorganism is of the genus *Klebsiella*.

In specific embodiments, the invention also provides compounds of any of the formulas herein which inhibit the growth of a microorganism having UGM which exhibit a dissociation constant K for the UGM enzyme of 100 µM or less. In another embodiment, the compound exhibits a dissociation constant K for the UGM enzyme of 50 µM or less. In another embodiment, the compound exhibits a dissociation constant K for the UGM enzyme of 25 µM or less. In another embodiment, the compound exhibits a dissociation constant K for the UGM enzyme of 10 µM or less. In further embodiments, the microorganism is a *Mycobacterium*, particularly *Mycobacterium tuberculosis*. In additional embodiments the microorganism is of the genus *Klebsiella*.

Additional aspects and embodiments of the invention will be apparent on review of the detailed description and examples.

BRIEF DESCRIPTION OF THE DRAWINGS

FIGS. 4A and 4B illustrate the results of disc assays to assess microbial growth inhibition by a 2-aminothiazole. Discs applied with DMSO (negative control, FIG. 4A) or the illustrated compound in DMSO (FIG. 4B) were placed on agar medium inoculated with *M. smegmatis*. The zone of inhibition persisted throughout the 4 days of the assay.

FIG. 11, pages 1 to 3, provides a table of exemplary data for the indicated compounds which compares $K_d$ ($UGM_{myco}$), relative $UGM_{myco}$ activity at 50 µM and the qualitative results of bacterial growth disc assays.

FIG. 12A provides a table of exemplary MIC data.

DETAILED DESCRIPTION OF THE INVENTION

Figure 1A:
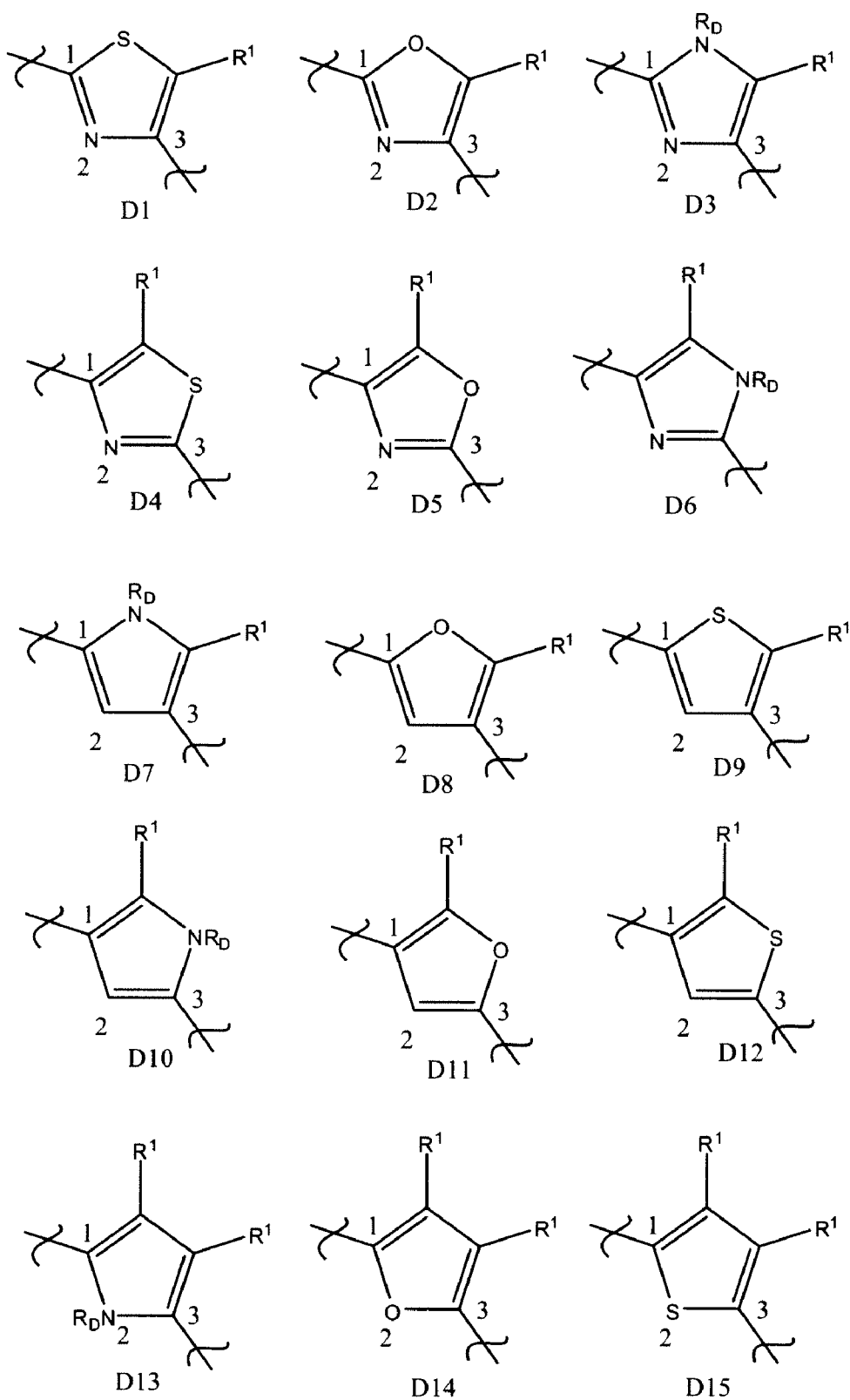
FIGS. 1A-1C illustrate exemplary D rings for formulas herein.
Figure 1B:
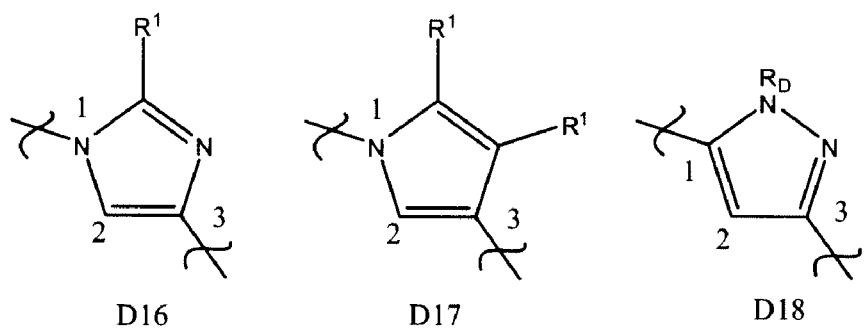
Figure 1B:
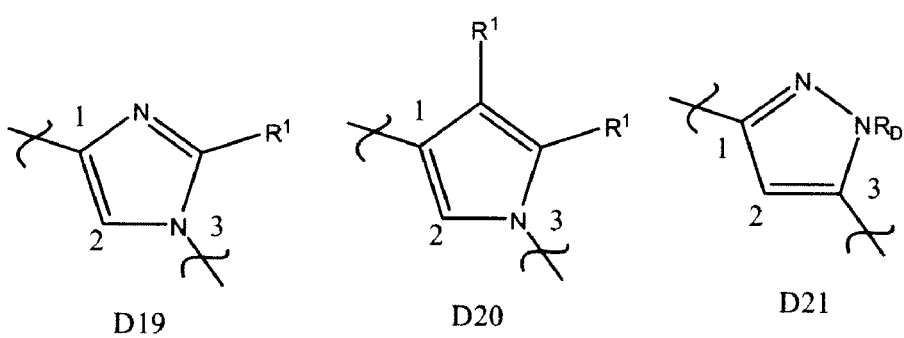
Figure 1B:
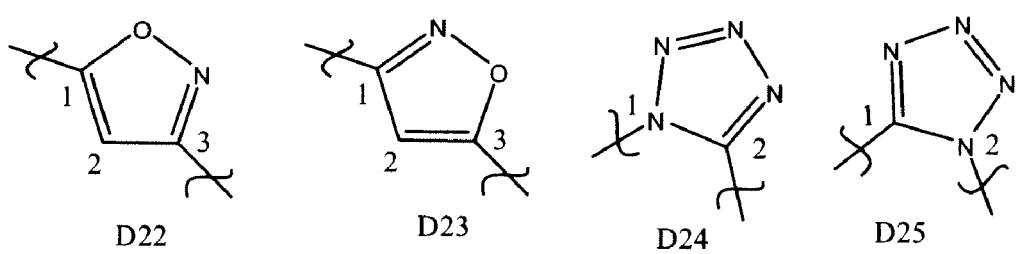
Figure 1B:
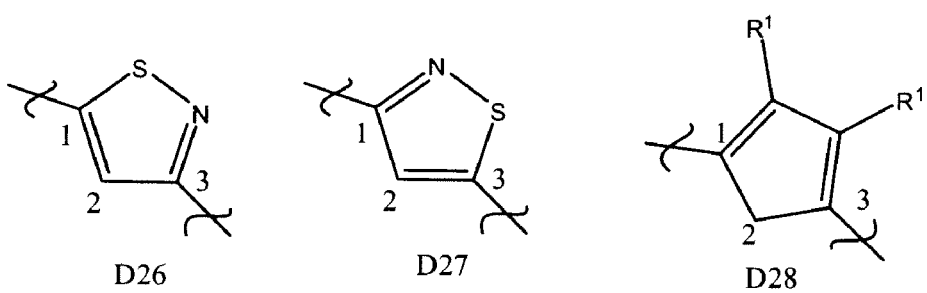
Figure 1B:
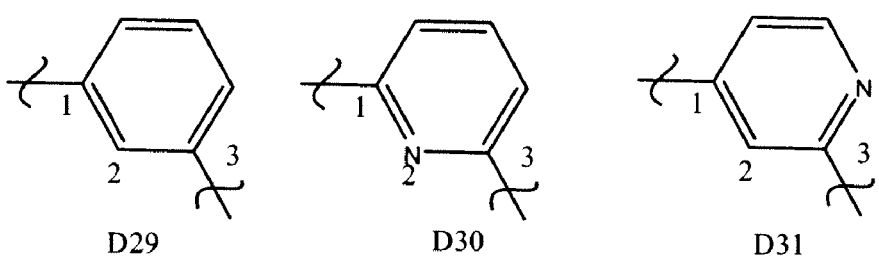
Figure 1C:
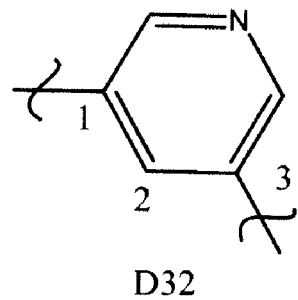
Figure 1C:
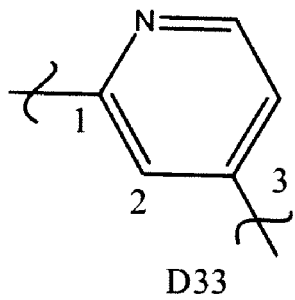
Figure 1C:
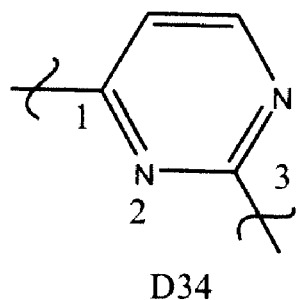
Figure 1C:
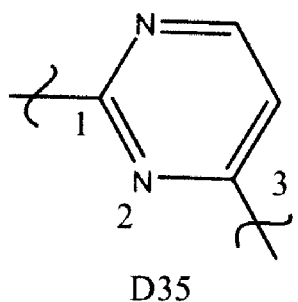
Figure 1C:
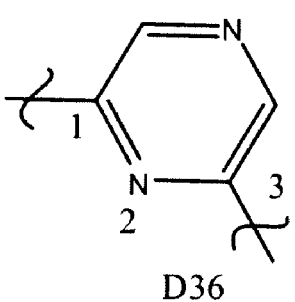
Figure 1C:
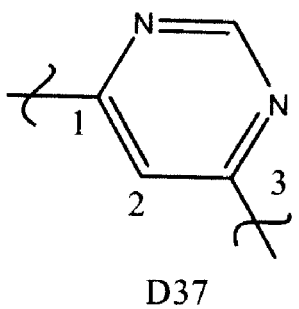
Figure 1C:
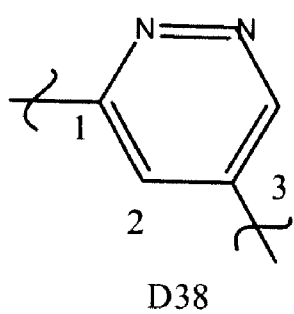
Figure 1C:
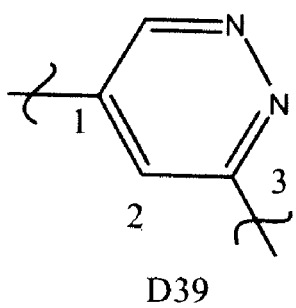
Figure 1C:
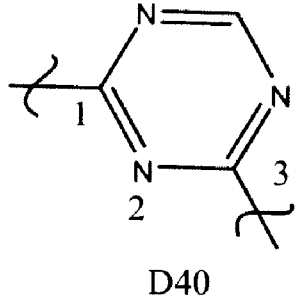
Figure 1C:
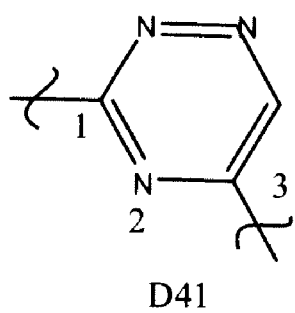
Figure 1C:
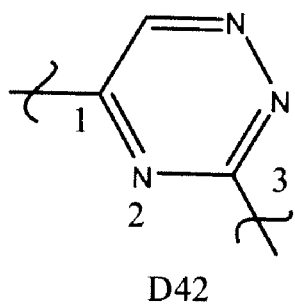
Figure 2A:
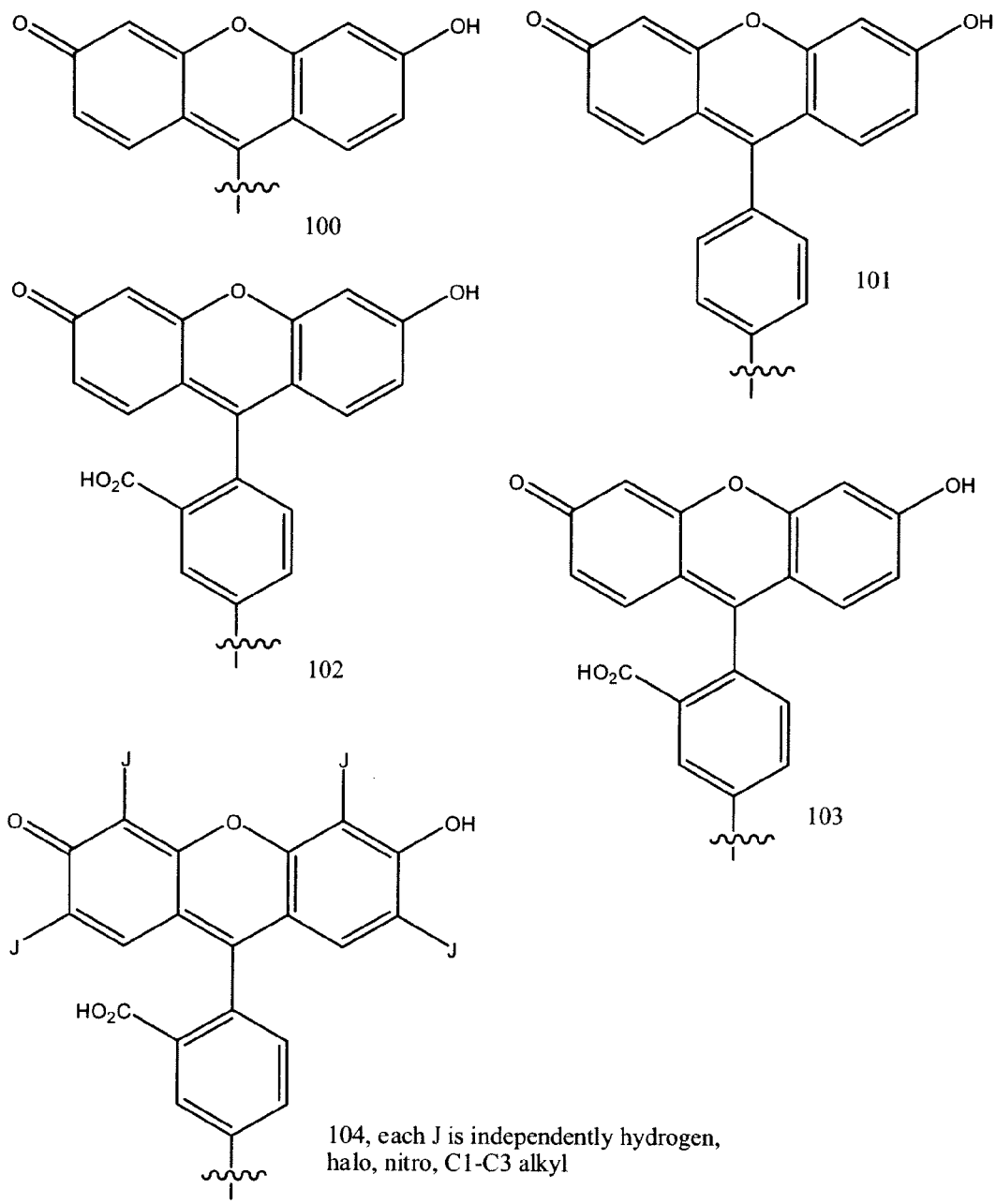
FIG. 2A or 2B illustrate exemplary AR groups for formulas herein.
Figure 2B:
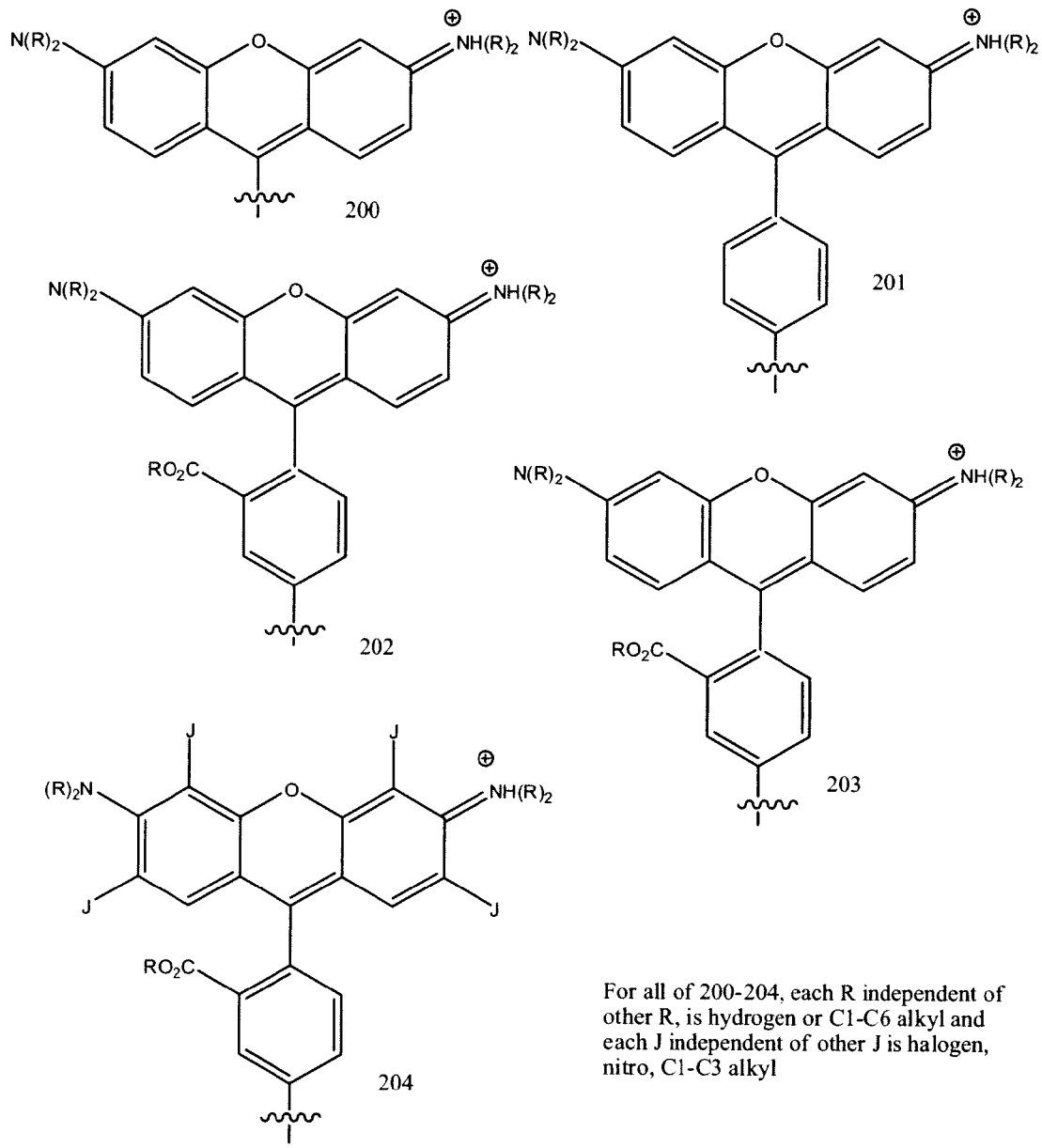

The invention is based at least in part on the identification of certain small molecule inhibitors of UDP-galactopyranose mutase (UGM) which have activity as inhibitors of microbial growth of microorganisms which contain this enzyme and particularly those microorganisms in which this enzyme is responsible for the incorporation of galactofuranose residues: uridine 5'-diphosphate (UDP) galactopyranose mutase.

In specific embodiments, the invention provides compounds of any of formulas I, II, IVA, IVC, IVE, VA, VC, VIA, VIIA, and X-XIII where the D ring is one of D1-D42. In specific embodiments, the D ring is a five member ring. In specific embodiments, the D ring is a five member ring having two different heteroatoms in the ring. In specific embodiments, the D ring is a five member ring having one S and one N in the ring. In specific embodiments, the D ring is any of D1-D15, or D16-D29, or D30-42. In specific embodiments, the D ring is a six member ring. In specific embodiments, the D ring is a six member ring having one heteroatom in the ring. In specific embodiments, the D ring is a six member ring having two heteroatoms in the ring. In specific embodiments, the D ring is a six member ring having three heteroatoms in the ring. In specific embodiments, the D ring is a six member ring having one, two or three N in the ring.

In specific embodiments, the invention provides compounds of any of the formulas herein, wherein:

D ring is D1 or D4;
D ring is D1-D6;
D ring is D2 or D5;
D ring is D3 or D6;
D ring is D7-D15;
D ring is D7, D10 or D13;
D rig is D8, D11 or D14;
D ring is D9, D12 or D15;
D ring is D3, D6, D16, D18, D19, or D21;
D ring is D16 or D19;
D ring is D17 or D20;
D ring is D18 or D 21;
D ring is D28 or D29;
D ring is D30-D39;
D ring is D30, D31, D32, or D33;
D ring is D34-D39; or
D ring is D40-D42; and/or
$R^1$ is hydrogen; or
$R^1$ is a methyl group; and/or
$R_A$ is a hydrogen;
$R_A$ is a halogen;
$R_A$ is iodine;
$R_A$ is chlorine;
$R_A$ is bromine;
$R_A$ is hydroxide; or
$R_A$ is nitro, and/or
n is 1; or
n is 0; and/or
$R_B$ is substitution by five halogens on the B ring;
$R_B$ is substitution by five fluorines on the B ring;
$R_B$ is substitution by three halogens on the B ring;
$R_B$ is substitution by three chlorines on the B ring;
$R_B$ is substitution by three bromines on the B ring;
$R_B$ is substitution by three fluorines on the B ring;
$R_B$ is substitution by three iodines on the B ring;
$R_B$ is substitution by halogens at carbons 2, 3 and 4 on the B ring;
$R_B$ is substitution by chlorines at carbons 2, 3 and 4 on the B ring;
$R_B$ is substitution by fluorines at carbons 2, 3 and 4 on the B ring;
$R_B$ is substitution by bromines at carbons 2, 3 and 4 on the B ring;
$R_B$ is substitution by iodines at carbons 2, 3 and 4 on the B ring;
$R_B$ is substitution by halogens at carbons 1, 2 and 3 on the B ring;
$R_B$ is substitution by chlorines at carbons 2, 3 and 4 on the B ring;
$R_B$ is substitution by two halogens on the B ring;
$R_B$ is substitution by two chlorines on the B ring;
$R_B$ is substitution by two bromines on the B ring;
$R_B$ is substitution by two iodines on the B ring;
$R_B$ is substitution by two fluorines on the B ring;
$R_B$ is substitution by halogens at carbons 2 and 4 on the B ring;
$R_B$ is substitution by fluorines at carbons 2 and 4 on the B ring;
$R_B$ is substitution by chlorines at carbons 2 and 4 on the B ring;
$R_B$ is substitution by bromines at carbons 2 and 4 on the B ring;
$R_B$ is substitution by iodines at carbons 2 and 4 on the B ring;
$R_B$ is substitution by halogens at carbons 1 and 3 on the B ring;
$R_B$ is substitution by fluorines at carbons 1 and 3 on the B ring;
$R_B$ is substitution by chlorines at carbons 1 and 3 on the B ring;
$R_B$ is substitution by bromines at carbons 1 and 3 on the B ring;

$R_B$ is substitution by iodines at carbons 1 and 3 on the B ring;
$R_B$ is substitution by halogens at carbons 2 and 3 on the B ring;
$R_B$ is substitution by fluorines at carbons 2 and 3 on the B ring;
$R_B$ is substitution by chlorines at carbons 2 and 3 on the B ring;
$R_B$ is substitution by bromines at carbons 2 and 3 on the B ring;
$R_B$ is substitution by iodines at carbons 2 and 3 on the B ring;
$R_B$ is substitution by one halogen on the B ring;
$R_B$ is substitution by one fluorine on the B ring;
$R_B$ is substitution by one chlorine on the B ring;
$R_B$ is substitution by one bromine on the B ring;
$R_B$ is substitution by one iodine on the B ring;
$R_B$ is substitution by one halogen on carbon 3 of the B ring;
$R_B$ is substitution by one fluorine on carbon 3 of the B ring;
$R_B$ is substitution by one chlorine on carbon 3 of the B ring;
$R_B$ is substitution by one chlorine on carbon 2 of the B ring;
$R_B$ is substitution by one chlorine on carbon 1 of the B ring;
$R_B$ is substitution by one bromine on carbon 3 of the B ring;
$R_B$ is substitution by one iodine on carbon 3 of the B ring;
$R_B$ is substitution by one nitro group on the B ring;
$R_B$ is substitution by one nitro group on carbon 2 of the B ring;
$R_B$ is substitution by one nitro group on carbon 3 of the B ring;
$R_B$ is substitution by one hydroxyl group on the B ring;
$R_B$ is substitution by one hydroxyl group on carbon 3 of the B ring;
$R_B$ is substitution by one methoxy group on the B ring;
$R_B$ is substitution by one methoxy group on carbon 3 of the B ring;
$R_B$ is substitution by one cyano group on the B ring;
$R_B$ is substitution by one cyano group on carbon 3 of the B ring;
$R_B$ is substitution by a C1-C6 alkyl group at carbon 3 of the B ring;
$R_B$ is substitution by a nitro group at carbon 2 and a halogen at carbon 3 of the B ring;
$R_B$ is substitution by a nitro group at carbon 2 and a chlorine at carbon 3 of the B ring;
$R_B$ is substitution by a C1-C3 alkyl group at carbon 1 and a halogen at carbon 3 of the B ring;
$R_B$ is substitution by a C1-C3 alkyl group at carbon 1 and a hydroxy at carbon 3 of the B ring;
$R_B$ is substitution including two different substituents on the B ring; and/or
$R^1$ attached to the thiazole ring and $R_B$ together form:

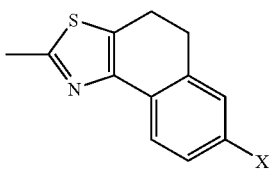

where X is selected from hydrogen, halogen, hydroxyl, methoxy, nitro or cyano;
X in the above formula is halogen;
X in the above formula is chlorine;
X in the above formula is iodine; and/or
A is phenyl with an RA substituent at the 3 carbon of the A ring;
A is optionally substituted 1-naphtyl;
A is optionally substituted 2-napthyl; or A is

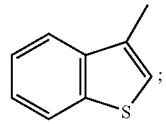

and/or
the B ring is 1-napthyl;
the B ring is 2-napthyl; and/or
$R_C$ is substitution by five halogens on the C ring;
$R_C$ is substitution by five fluorines on the C ring;
$R_C$ is substitution by three halogens on the C ring;
$R_C$ is substitution by three chlorines on the C ring;
$R_C$ is substitution by three bromines on the C ring;
$R_C$ is substitution by three fluorines on the C ring;
$R_C$ is substitution by three iodines on the C ring;
$R_C$ is substitution by halogens at carbons 2, 3 and 4 on the C ring;
$R_C$ is substitution by chlorines at carbons 2, 3 and 4 on the C ring;
$R_C$ is substitution by fluorines at carbons 2, 3 and 4 on the C ring;
$R_C$ is substitution by bromines at carbons 2, 3 and 4 on the C ring;
$R_C$ is substitution by iodines at carbons 2, 3 and 4 on the C ring;
$R_C$ is substitution by two halogens on the C ring;
$R_C$ is substitution by two chlorines on the C ring;
$R_C$ is substitution by two bromines on the C ring;
$R_C$ is substitution by two iodines on the C ring;
$R_C$ is substitution by two fluorines on the C ring;
$R_C$ is substitution by halogens at carbons 2 and 4 on the C ring;
$R_C$ is substitution by fluorines at carbons 2 and 4 on the C ring;
$R_C$ is substitution by chlorines at carbons 2 and 4 on the C ring;
$R_C$ is substitution by bromines at carbons 2 and 4 on the C ring;
$R_C$ is substitution by iodines at carbons 2 and 4 on the C ring;
$R_C$ is substitution by halogens at carbons 1 and 3 on the C ring;
$R_C$ is substitution by fluorines at carbons 1 and 3 on the C ring;
$R_C$ is substitution by chlorines at carbons 1 and 3 on the C ring;
$R_C$ is substitution by bromines at carbons 1 and 3 on the C ring;
$R_C$ is substitution by iodines at carbons 1 and 3 on the C ring;
$R_C$ is substitution by halogens at carbons 2 and 3 on the C ring;
$R_C$ is substitution by fluorines at carbons 2 and 3 on the C ring;
$R_C$ is substitution by chlorines at carbons 2 and 3 on the C ring;
$R_C$ is substitution by bromines at carbons 2 and 3 on the C ring;
$R_C$ is substitution by iodines at carbons 2 and 3 on the C ring;
$R_C$ is substitution by one halogen on the C ring;
$R_C$ is substitution by one fluorine on the C ring;
$R_C$ is substitution by one chlorine on the C ring;
$R_C$ is substitution by one bromine on the C ring;
$R_C$ is substitution by one iodine on the C ring;
$R_C$ is substitution by one halogen on carbon 3 of the C ring;
$R_C$ is substitution by one fluorine on carbon 3 of the C ring;
$R_C$ is substitution by one chlorine on carbon 3 of the C ring;
$R_C$ is substitution by one bromine on carbon 3 of the C ring;
$R_C$ is substitution by one iodine on carbon 3 of the C ring;

$R_C$ is substitution by one nitro group on the C ring;
$R_C$ is substitution by one nitro group on carbon 2 of the C ring;
$R_C$ is substitution by one nitro group on carbon 3 of the C ring;
$R_C$ is substitution by one hydroxyl group on the C ring;
$R_C$ is substitution by one hydroxyl group on carbon 3 of the C ring;
$R_C$ is substitution by one cyano group on the C ring;
$R_C$ is substitution by one cyano group on carbon 3 of the C ring; and/or
$R_B$ includes substitution at the 3 position with -M-L-Q-AR; where:
M is thiourea; and/or
Q is thiourea, and/or
M is —O— or $NR_M$—; and/or
M is —O— or —$NR_M$— and Q is thiourea; and/or
L is —$(CH_2)_a$—; and/or
M is —O— or —$NR_M$—, Q is thiourea and L is —$(CH_2)_a$—; and/or
AR is naphthyl
AR is benzofuranyl; or
compounds of formulas which combine any of the above embodiments.

In specific embodiments, the invention provides compounds of any formulas herein formula where n is 0, where:
$R_A$ is halogen and $R_B$ is hydroxyl at the 3 carbon of the B ring;
$R_A$ is chlorine and $R_B$ is hydroxyl at the 3 carbon of the B ring;
$R_A$ is halogen and $R_B$ is halogens at the 2 and 4 carbons of the B ring;
$R_A$ is chlorine and $R_B$ is halogens at the 2 and 4 carbons of the B ring;
$R_A$ is chlorine and $R_B$ is chlorines at the 2 and 4 carbons of the B ring;
$R_A$ is chlorine and $R_B$ is fluorines at the 2 and 4 carbons of the B ring;
$R_A$ is iodine and $R_B$ is halogens at the 2 and 4 carbons of the B ring;
$R_A$ is iodine and $R_B$ is chlorines at the 2 and 4 carbons of the B ring;
$R_A$ is iodine and $R_B$ is fluorines at the 2 and 4 carbons of the B ring;
$R_A$ is halogen and $R_B$ is halogen at the 3 carbon of the B ring;
$R_A$ is halogen and $R_B$ is chlorine at the 3 carbon of the B ring;
$R_A$ is halogen and $R_B$ is iodine at the 3 carbon of the B ring;
$R_A$ is halogen and $R_B$ is bromine at the 3 carbon of the B ring;
$R_A$ is halogen and $R_B$ is fluorine at the 3 carbon of the B ring;
$R_A$ is chlorine and $R_B$ is chlorine at the 3 carbon of the B ring;
$R_A$ is chlorine and $R_B$ is iodine at the 3 carbon of the B ring;
$R_A$ is chlorine and $R_B$ is bromine at the 3 carbon of the B ring;
$R_A$ is chlorine and $R_B$ is fluorine at the 3 carbon of the B ring;
$R_A$ is bromine and $R_B$ is chlorine at the 3 carbon of the B ring;
$R_A$ is bromine and $R_B$ is iodine at the 3 carbon of the B ring;
$R_A$ is bromine and $R_B$ is bromine at the 3 carbon of the B ring;
$R_A$ is bromine and $R_B$ is fluorine at the 3 carbon of the B ring;
$R_A$ is iodine and $R_B$ is chlorine at the 3 carbon of the B ring;
$R_A$ is iodine and $R_B$ is iodine at the 3 carbon of the B ring;
$R_A$ is iodine and $R_B$ is bromine at the 3 carbon of the B ring;
$R_A$ is iodine and $R_B$ is fluorine at the 3 carbon of the B ring;
$R_A$ is halogen and $R_B$ is nitro at the 2 carbon of the B ring;
$R_A$ is iodine and $R_B$ is nitro at the 2 carbon of the B ring;
$R_A$ is halogen and $R_B$ is halogens at the 1 and 3 carbons of the B ring;
$R_A$ is chlorine and $R_B$ is halogens at the 1 and 3 carbons of the B ring;
$R_A$ is chlorine and $R_B$ is chlorines at the 1 and 3 carbons of the B ring;
$R_A$ is chlorine and $R_B$ is fluorines at the 1 and 3 carbons of the B ring;
$R_A$ is iodine and $R_B$ is halogens at the 1 and 3 carbons of the B ring;
$R_A$ is iodine and $R_B$ is chlorines at the 1 and 3 carbons of the B ring;
$R_A$ is iodine and $R_B$ is fluorines at the 1 and 3 carbons of the B ring;
$R_A$ is bromine and $R_B$ is halogens at the 1 and 3 carbons of the B ring;
$R_A$ is bromine and $R_B$ is chlorines at the 1 and 3 carbons of the B ring;
$R_A$ is bromine and $R_B$ is fluorines at the 1 and 3 carbons of the B ring;
$R_A$ is fluorine and $R_B$ is halogens at the 1 and 3 carbons of the B ring;
$R_A$ is fluorine and $R_B$ is chlorines at the 1 and 3 carbons of the B ring;
$R_A$ is fluorine and $R_B$ is fluorines at the 1 and 3 carbons of the B ring;
$R_A$ is halogen and $R_B$ is halogens at the 2 and 3 carbons of the B ring;
$R_A$ is chlorine and $R_B$ is halogens at the 2 and 3 carbons of the B ring;
$R_A$ is chlorine and $R_B$ is chlorines at the 2 and 3 carbons of the B ring;
$R_A$ is chlorine and $R_B$ is fluorines at the 2 and 3 carbons of the B ring;
$R_A$ is iodine and $R_B$ is halogens at the 2 and 3 carbons of the B ring;
$R_A$ is iodine and $R_B$ is chlorines at the 2 and 3 carbons of the B ring;
$R_A$ is iodine and $R_B$ is fluorines at the 2 and 3 carbons of the B ring;
$R_A$ is bromine and $R_B$ is halogens at the 2 and 3 carbons of the B ring;
$R_A$ is bromine and $R_B$ is chlorines at the 2 and 3 carbons of the B ring;
$R_A$ is bromine and $R_B$ is fluorines at the 2 and 3 carbons of the B ring;
$R_A$ is fluorine and $R_B$ is halogens at the 2 and 3 carbons of the B ring;
$R_A$ is fluorine and $R_B$ is chlorines at the 2 and 3 carbons of the B ring;
$R_A$ is fluorine and $R_B$ is fluorines at the 2 and 3 carbons of the B ring;
$R_A$ is halogen and $R_B$ is halogens at the 1, 2 and 3 carbons of the B ring;
$R_A$ is iodine and $R_B$ is halogens at the 1, 2 and 3 carbons of the B ring;
$R_A$ is chlorine and $R_B$ is halogens at the 1, 2 and 3 carbons of the B ring;
$R_A$ is bromine and $R_B$ is halogens at the 1, 2 and 3 carbons of the B ring;
$R_A$ is fluorine and $R_B$ is halogens at the 1, 2 and 3 carbons of the B ring;
$R_A$ is iodine and $R_B$ is chlorine at the 1, 2 and 3 carbons of the B ring;
$R_A$ is chlorine and $R_B$ is chlorine at the 1, 2 and 3 carbons of the B ring;
$R_A$ is bromine and $R_B$ is chlorine at the 1, 2 and 3 carbons of the B ring;
$R_A$ is fluorine and $R_B$ is chlorine at the 1, 2 and 3 carbons of the B ring;
$R_A$ is iodine;
$R_A$ is chlorine; or
$R_A$ is nitro and $R_B$ is halogen at the 3 carbon of the B ring.

In specific embodiments, the C ring and the A ring are not aryl sulfinyl, aryl sulfuryl, arylsulfonyl or aryl sulfonic acid groups. In specific embodiments, the D ring is a ring other than a thiazolidinone ring. In specific embodiments, the D ring is a ring other than a furanyl ring.

In specific embodiments, the invention provides compound of any formulas herein which exhibit $K_d$ (μM) on $UGM_{myco}$ of 100 or less. In other embodiments, the invention provides compound of any formulas herein which exhibit $K_d$ (microM) on $UGM_{myco}$ of 80 or less. In other embodiments, the invention provides compound of any formulas herein which exhibit $K_d$ (microM) on $UGM_{myco}$ of 60 or less.

In specific embodiments, the invention provides compounds of any formulas herein which exhibit $K_d$ (μM) as measured by the fluorescence polarization assay on the UGM isoform from *M. tuberculosis* of 80 or less. In other embodiments, the invention provides compounds of formulas herein which exhibit $K_d$ (μM) as measured by the fluorescence polarization assay on the UGM isoform from *M. tuberculosis* of 60 or less. In other embodiments, the invention provides compounds of any formulas herein which exhibit $K_d$ (μM) as measured by the fluorescence polarization assay on the UGM isoform from *M. tuberculosis* of 25 or less.

In specific embodiments, the invention provides compounds of any formulas herein which exhibit $K_d$ (μM) as measured by the fluorescence polarization assay on the UGM isoform from *K. pneumoniae* of 80 or less. In other embodiments, the invention provides compounds of any formulas herein which exhibit $K_d$ (μM) as measured by the fluorescence polarization assay on the UGM isoform from *K. pneumoniae* of 60 or less. In other embodiments, the invention provides compounds of any formulas herein which exhibit $K_d$ (μM) as measured by the fluorescence polarization assay on the UGM isoform from *K. pneumoniae* of 25 or less.

The invention further provides a method for inhibiting UGM in vitro or in vivo by contacting a biological composition comprising an active UGM with an amount of one or more of the compounds of any of the formulas herein effective for inhibiting UGM. In a specific embodiment, the inhibition of UGM is in vivo in a prokaryote. In a specific embodiment, the inhibition of UGM is in vivo in a eukaryote.

Compounds of the invention are useful for inhibiting the growth of a microorganism containing UGM which is the enzyme responsible for the conversion of UDP-galactopyranose to UDP-galactofuranose. UGM is expected to be present in microorganisms in which galactofuranose (Galf) residues are present, for example in cell walls. Galactofuranose (Galf) residues are present in many pathogenic microorganisms (Pedersen, L. L.; Turco, S. J. *Cell. Mol. Life. Sci.* 2003, 60, 259-266.) The gene encoding UGM is essential for mycobacterial viability (Pan, F.; Jackson, M.; Ma, Y. F.; McNeil, M. *J. Bacteriol.* 2001, 183, 3991-3998) suggesting that Galf-containing glycoconjugates are necessary components of the mycobacterial cell wall. Compounds of the invention are useful for inhibiting the growth of microorganisms containing galactofuranose residues, particularly those having such residues in the cell wall and more particularly pathogenic microorganisms containing galactofuranose residues.

Compounds of the invention are useful for inhibition of growth of microorganisms of the genus *Mycobacterium*, particularly including *M. tuberculosis* and *M. smegmatis*. Compounds of the invention can also be employed to inhibit the growth of *Mycobacterium leprae*, *Mycobacterium bovis*, *Mycobacterium africanum*, *Mycobacterium canetti*, and *Mycobacterium microti*.

Compounds of the invention are useful for inhibition of the growth of gram-negative bacteria and particularly those of the genus *Klebsiella* and particularly *K. pneumoniae*. The compounds of the invention can also be employed to inhibit the growth of *Klebsiella ozaenae*, *Klebsiella rhinoscleromatis*, *Klebsiella oxytoca*, *Klebsiella planticola*, *Klebsiella terrigena*, and *Klebsiella ornithinolytica*. Klebsiellae are important pathogens in nosocomial infections. The compounds of the invention are useful for the treatment of nosocomial infections.

Compounds of the invention are useful for inhibition of the growth of or for attenuation of the virulence of eukaryotic pathogens, including yeast, fungi, protozoa and nematodes. The compounds of the invention are useful for inhibiting the growth or attenuating the virulence of, for example, pathogenic *Aspergillus*, in particular *Aspergillus fumagatus*.

The invention further provides a method of screening for and identifying small molecules which inhibit growth of bacteria which contain the UGM enzyme and particularly those bacteria in which the UGM enzyme is associated with forming the bacterial cell wall. The method is particularly useful for screening for and identifying small molecules which inhibit growth of members of the genus *Klebsiella* and more particularly for *K. pneumoniae*.

The invention further provides a method of screening for and identifying small molecules which inhibit growth of mycobacteria which contain the UGM enzyme and particularly those mycobacteria in which the UGM enzyme is responsible for the incorporation of galactofuranose residues. The method is particularly useful for screening for and identifying small molecules which inhibit growth of members of the genus *Mycobacterium* and more particularly for *M. tuberculosis*.

The term "microorganism" is used broadly herein to refer to organisms too small to be seen with the naked human eye and includes prokaryotes (e.g., bacteria and mycobacteria), single cell and multiple cell eukaryotes, yeast, fungi and protozoa. More specifically microorganisms upon which the compounds of this invention act are human or non-human mammal pathogens. Pathogenic protozoa include, among others, plasmodium, trypanosomes and shmania (e.g., *Leishmania major*, *Trypanosoma cruizii*.) Fungi include cryptococcus and chlamydomonas (e.g., *Cryptococcus neoformans*). Microorganism also includes parasitic nematodes.

In a specific embodiment, compounds of this invention of any of the formulas herein can block incorporation of Galf into polysaccharides essential for viability or virulence of pathogenic microorganisms.

In specific embodiments, the invention provides compounds of any formulas herein which are cell permeable.

The term "alkyl" refers to a monoradical of a branched or unbranched (straight-chain or linear) saturated hydrocarbon and to cycloalkyl groups having one or more rings. Unless otherwise indicated preferred alkyl groups have 1 to 22 carbon atoms and more preferred are those that contain 1-12 carbon atoms. Short alkyl groups are those having 1 to 6 carbon atoms including methyl, ethyl, propyl, butyl, pentyl and hexyl groups, including all isomers thereof. Long alkyl groups are those having 8-22 carbon atoms and preferably those having 12-22 carbon atoms. The term "cycloalkyl" refers to cyclic alkyl groups having 3 to 22 and preferably 5-10 carbon atoms having a single cyclic ring or multiple condensed rings. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined herein.

The term "alkylene" refers to a diradical of a branched or unbranched saturated hydrocarbon chain, which unless otherwise indicated can have 1 to 15 carbon atoms, 1 to 12 carbon atoms, 1-6 carbon atoms, or 2-4 carbon atoms. This term is exemplified by groups such as methylene (—CH$_2$—), ethylene (—CH$_2$CH$_2$—), more generally —(CH$_2$)$_n$—, where n is 1-10 or more preferably 1-6 or n is 2, 3 or 4. Alkylene groups may be branched, e.g., by substitution with alkyl group substituents. Alkylene groups may be optionally substituted as described herein. More specifically alkylene groups may be substituted with one or more hydroxyl groups and/or one or more halogen groups. Alkylene groups may have up to two non-hydrogen substituents per carbon atoms. The term "alkenylene" refers to a diradical of a branched or unbranched alkene. Alkenylene linkers can contain one or more than one double bond. In specific embodiments, alkenylene linkers contain 1 double bond or two double bonds. Alkenylene linkers can unless otherwise indicated have 2 to 10 carbon atoms, or 2-6 carbon atoms, or 3-5 carbon atoms. The term cycloalkylene relates to an alkylene group that contains a carbon ring having 3-8 carbon atoms and preferably having 5 or 6 carbon atoms.

The term alkoxy refers to the group —OR where R is an alkyl group as defined above.

The term "alkyleneoxy" refers to a diradical of a branched or unbranched saturated hydrocarbon chain in which one or more —CH2- groups are replaced with —O—, which unless otherwise indicated can have 1 to 10 carbon atoms, or 1-6 carbon atoms, or 2-4 carbon atoms. This term is exemplified by groups such as —CH$_2$OCH$_2$—, —CH$_2$CH$_2$OCH$_2$CH$_2$—, —CH$_2$CH$_2$OCH$_2$CH$_2$OCH$_2$CH$_2$—, more generally —((CH$_2$)$_x$—O—)$_a$—(CH$_2$)$_y$—, where x and y are integers ranging from 1-6, and a is an integer ranging from 1-3, as well as, —OCH$_2$—CH$_2$—O—, —O—(CH$_2$)$_x$—O—, —O—(CH$_2$)$_n$O—(CH$_2$)$_y$—O—, —O—((CH$_2$)O—)$_a$—, or —O—((CH$_2$)$_x$—O—)$_a$—(CH$_2$)$_y$—, where x and y are integers ranging from 1-6, and a is an integer ranging from 1-3, Alkyleneoxy groups may be branched, e.g., by substitution with alkyl group substituents.

The term "carbocyclic" is used generically herein to refer to groups which contain a carbon ring which may be a saturated, partially unsaturated or aromatic ring. Carbocyclic groups may contain one or more than one carbon ring which ring may be a cycloakyl, unsaturated cycloalkyl or aryl ring. Typically carbocyclic rings include those having 3-12 carbon atoms in the ring. Carbocyclic rings include those having two or more fused rings, bicyclic rings, tricyclic ring etc. Preferred carbocyclic rings have 6 to 12 carbon atoms. Unless otherwise indicated carbocyclic groups are optionally substituted as defined herein.

The term "heterocyclic" is also used generically herein to refer to carbocyclic rings in which one or more ring carbons are replaced with a heteroatom. The heterocyclic ring may contain a carbon ring in combination with a heteroatom containing ring. Heterocyclic groups can contain from one to six heteroatoms including one, two, three or four hetero atoms. Preferred heteroatoms are N, O or S (or NR' where R' is a hydrogen or an optional substituent). Heterocyclic groups can be or contain heteroaryl groups. Unless otherwise indicated heterocyclic groups are optionally substituted as defined herein.

The term heterocyclene group relates to a diradical of a heterocyclic group. Such groups can contain one or more heteroatoms, particularly O, N or S atoms or combinations thereof. A heterocylene group can, for example have a 5 or 6-member heterocyclic ring.

The term "aryl" refers to a monoradical containing at least one aromatic ring. The radical is formally derived by removing a H from a ring carbon. Aryl groups contain one or more rings at least one of which is aromatic. Rings of aryl groups may be linked by a single bond or a linker group or may be fused. Exemplary aryl groups include phenyl, biphenyl and naphthyl groups. Aryl groups include those having from 6 to 30 carbon atoms and those containing 6-12 carbon atoms. Unless otherwise noted aryl groups are optionally substituted as described herein.

The term "arylene" refers to a diradical containing at least one aromatic ring. The diradical is formally derived by removing a H from two different ring carbons, e.g., a phenylene, and more specifically a 1,4-phenylene. Arylene groups include those having from 6 to 30 carbon atoms and those containing 612 carbon atoms. Unless otherwise noted arylene groups are optionally substituted as described herein.

The term "heteroaryl" refers to a group that contains at least one aromatic ring in which one or more of the ring carbons is replaced with a heteroatom (non-carbon atom). To satisfy valence the heteroatom may be bonded to H or a substituent groups. Ring carbons may be replaced with —O—, —S—, —NR—, —N═, —PR—, or —POR among others, where R is an alkyl, aryl, heterocyclyl or heteroaryl group. Heteroaryl groups may include one or more aryl groups (carbon aromatic rings) heteroaromatic and aryl rings of the heteroaryl group may be linked by a single bond or a linker group or may be fused. Heteroaryl groups include those having aromatic rings with 5 or 6 ring atoms of which 1-3 ring atoms are heteroatoms. Preferred heteroatoms are —O—, —S—, —NR— and —N═. Heteroaryl groups include those containing 5-12 ring atoms as well as those having 5 and 6 ring atoms. Unless otherwise noted heteroaryl groups are optionally substituted as described herein.

The term "heteroarylene" refers to a diradical containing at least one heteroaromatic ring. The diradical is formally derived by removing a H from two different ring carbons. Heteroarylene groups include those having from 6 to 30 carbon atoms and those containing 6-12 carbon atoms. Unless otherwise noted heteroarylene groups are optionally substituted as described herein.

The term tetrazolyl refers to groups derived formally from tetrazole or substituted tetrazoles by removal of a hydrogen, including:

tetrazol-1-yl:

tetrazol-2-yl:

tetrazol-5-yl:

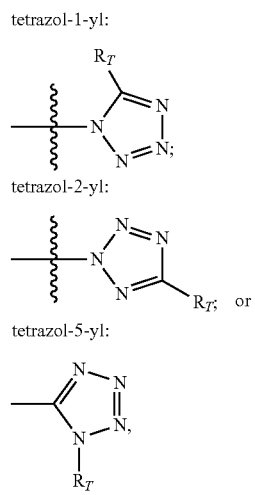

where R$_T$ is hydrogen or a non-hydrogen substituent, which can be an optionally substituted alkyl or an optionally substituted aryl group. In specific embodiments, R$_T$ are optionally substituted alkyl groups, particularly those having 1-6 carbon atoms, or optionally substituted aryl groups, particularly phenyl groups.

Additional chemical group or moiety names employed herein are intended to have their broadest meaning as understood in the art.

Unless otherwise specified optional substitution means substitution by one or more non-hydrogen substituents selected from halogen, hydroxyl, amine, cyano, azide, nitro, isocyanate, isothiocyanate, C1-C6 alkyl, C1-C3 alkyl, C1-C6 haloalkyl, C1-C3 haloalkyl, phenyl, benzyl, sulfate, phosphate, phosphonate, carboxyl, sulfonyl, sulfonamide, and amide. All alkyl, aryl, heteroaryl, heterocyclic, carbocyclic groups herein are optionally substituted with one or more non-hydrogen substituents unless otherwise specified. Substitution may be on one or more carbons or, if feasible, on one or more heteroatoms, e.g., a nitrogen. The number of substituents on such groups depends generally upon the nature of the group, but includes substitution with one, two, three, four, five or six substituents.

As to any of the groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

Treatment methods of this invention comprise the step of administering a effective amount of one or more compounds of this invention, or a salt thereof to an individual (human and/or non-human animal) to treat or prevent infection. The term "effective amount," as used herein, refers to the amount of the compound, that, when administered to the individual is effective to at least partially treat or prevent infection, or to at least partially ameliorate a symptom of infection. Infection herein refers to infection by a microorganism which contains the enzyme UGM. As is understood in the art, the effective amount of a given compound will depend at least in part upon, the mode of administration, any carrier or vehicle (e.g., solution, emulsion, etc.) employed, the extent of damage and the specific individual to whom the compound is to be administered (age, weight, condition, sex, etc.). The dosage requirements needed to achieve the "effective amount" vary with the particular compositions employed, the route of administration, the severity of the symptoms presented and the particular subject being treated. Based on the results obtained in standard pharmacological test procedures, projected daily dosages of active compound can be determined as is understood in the art.

Compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampoules, pre-filled syringes or sachets containing liquids. The unit dosage form can be, for example, a capsule or tablet itself, or it can be the appropriate number of any such compositions in package form.

Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

The therapeutically active compounds of the invention can be administered alone, but generally will be administered with a pharmaceutical carrier selected upon the basis of the chosen route of administration and standard pharmaceutical practice.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

The compounds of the present inventions may form salts which are also within the scope of this invention. Reference to a compound of the formulas herein is understood to include reference to salts thereof, unless otherwise indicated. The term "salt(s)", as employed herein, denotes acidic and/or basic salts formed with inorganic and/or organic acids and bases. In addition, when a compound of a formula herein contains both a basic moiety, such as, but not limited to an amine or a pyridine ring, and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formulas herein may have prodrug forms. As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. See for example a) Design of Prodrugs, edited by H. Bundgaard, (Elsevier, 1985), and Methods in Enzymology, Vol. 42, at pp. 309-396, edited by K. Widder, et. al. (Academic Press, 1985); b) A Textbook of Drug Design and Development, edited by Krosgaard-Larsen and H. Bundgaard, Chapter 5, "Design and Application of Prodrugs," by H. Bundgaard, at pp. 113-191 (1991); c) H. Bundgaard, Advanced Drug Delivery Reviews, Vol. 8, p. 1-38 (1992); and d) H. Bundgaard, et al., Journal of Pharmaceutical Sciences, Vol. 77, p. 285 (1988).

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, *Experimental and computational approaches to estimate solubility and permeability in drug discovery and development settings*, Adv. Drug Del. Rev., 2001, 46, 3-26 and Arup K. Ghose, Vellarkad N. Viswanadhan, and John J. Wendoloski, *A Knowledge-Based Approach in Designing Combinatorial or Medicinal Chemistry Libraries for Drug Discovery*, J. Combin. Chem., 1999, 1, 55-68.)

In general a preferred drug for oral administration exhibits no more than one violation of the following rules:

(1) Not more than 5 hydrogen bond donors (e.g., nitrogen or oxygen atoms with one or more hydrogens);

(2) Not more than 10 hydrogen bond acceptors (e.g., nitrogen or oxygen atoms);

(3) Molecular weight under 500 g/mol and more preferably between 160 and 480; or (4) log P less than 5 and more preferably between −0.4 to +5.6 and yet more preferably −1<log P<2. Methods for calculating or experimentally determining Log P are well-known in the art. Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art.

Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated. The invention illustratively described herein suitably may be practiced in the absence of any element or elements, limitation or limitations which is not specifically disclosed herein.

It is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims. It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. The broad term "comprising" is intended to encompass the narrower consisting essentially of and the even narrower consisting of: Thus, in any recitation herein of a phrase "comprising one or more claim element" (e.g., "comprising A and B), the phrase is intended to encompass the narrower, for example, "consisting essentially of A and B" and "consisting of A and B." Thus, the broader word "comprising" is intended to provide specific support in each use herein for either "consisting essentially of" or "consisting of."

One of ordinary skill in the art will appreciate that starting materials, reagents, synthetic methods, purification methods, analytical methods, and assay methods, other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by examples, preferred embodiments and optional features, modification and variation of the concepts herein disclosed may be resorted to by those skilled in the art, and that such modifications and variations are considered to be within the scope of this invention as defined by the appended claims.

All references cited herein are hereby incorporated by reference to the extent that there is no inconsistency with the disclosure of this specification. Some references provided herein are incorporated by reference to provide details concerning sources of starting materials; alternative starting materials, reagents, methods of synthesis, purification methods, and methods of analysis; as well as additional uses of the invention.

THE EXAMPLES

Example 1

Amino Thiozoles as UGM Inhibitors

Certain 5-arylidine-2-thioxo-4-thiazolidinone compounds were found to serve as ligands for UGM homologs. The thiazolidinone scaffold, however, reacts reversibly with biologically relevant thiols in solution and UGM inhibitors of this structural class fail to block mycobacterial growth (Carlson, E. E.; May, J. F.; Kiessling, L. L. *Chem. Biol.* 2006, 13, 825-837.) Given the reactivity of the thiazolidinones, an alternative scaffold that would display functionality important for UGM binding, yet be inert under physiological conditions was sought. Stable 2-aminothiazole derivatives were investigated because it was believed that such molecules would have a shape similar to that of thiazolidinones. In addition, compounds of this class can be assembled efficiently, as illustrated in the exemplary synthesis of Scheme 2 which includes four synthetic steps with minimal purification.

Specifically, the methyl ester of the racemic phenylalanine analog was converted to the thiourea using mild conditions. (Kearney, P. C.; Fernandez, M.; Flygare, J. A. *J. Org. Chem.* 1998, 63, 196-200.) The product was obtained using the Hantzsch thiazole synthesis, in which a thiourea generated from an aryl amino acid and an α-bromo ketone were condensed. The desired products were obtained after a single purification step (silica gel chromatography) in good overall yields (50-70%). Using this approach, 18 commercially available phenylalanine analogs and 23 α-bromo ketones (King, L. C.; Ostrun, G. K. *J. Org. Chem.* 1964, 29, 3459-3461) were employed to generate 62 aminothiazoles.

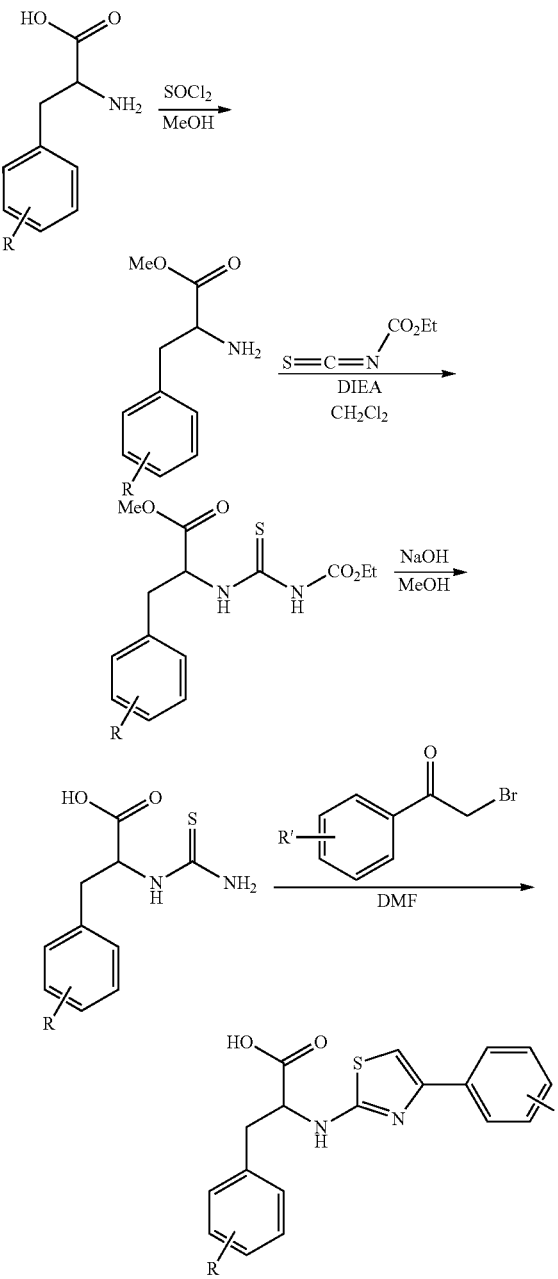

Scheme 2: Synthetic route to substituted 2-aminothiazoles.

Members of the resulting focused library were screened against $UGM_{kleb}$ and $UGM_{myco}$ using a previously described fluorescence polarization assay.[20,21] (Soltero-Higgin, M.; Carlson, E. E.; Phillips, J. H.; Kiessling, L. L. *J. Am. Chem. Soc.* 2004, 126, 10532-10533: Carlson, E. E.; May, J. F.; Kiessling, L. L. *Chem. Biol.* 2006, 13, 825-837.) Twenty-five 2-aminothiazoles were identified as good UGM ligands ($K_d$<60 μM). We assessed the ability of selected compounds to inhibit $UGM_{myco}$(Carlson, E. E.; May, J. F.; Kiessling, L. L. *Chem. Biol.* 2006, 13, 825-837) and found a correlation between binding affinity and inhibitory activity Kinetic assays revealed that the active 2-aminothiazoles function as competitive inhibitors with respect to UDP-Galf.

Figures 1, 6:
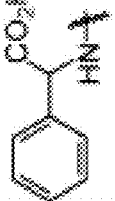
FIG. 6 (pages 1 to 4) is a Table of exemplary binding data as determined by the fluorescence polarization assay. Binding is shown for the UGM isoform from *K. pneumoniae* (K) and *M. tuberculosis* (M). Dissociation constants are given in units of µM. The data in FIG. 6 depicts the effects of varying the A ring substitution.
Figures 2, 6:
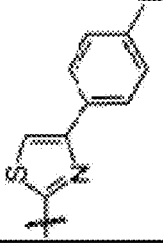

With access to a new class of $UGM_{myco}$ inhibitors, structural features which contribute to binding were explored. The 2-aminothiazoles and the thiazolidinone inhibitors possess aryl substituents in similar relative orientations. The consequences of perturbing this orientation were tested. Specifically, when a phenylglycine rather than phenylalanine building block was used, the resulting 2-aminothiazole was less potent (2-3 fold). Compounds with halogen substituents on either aryl ring or both had increased activity. In contrast, compounds bearing electron-rich rings were less effective inhibitors. It was found that a greater variety of substituents could be appended to the B than the A ring. Without wishing to be bound by any particular theories, the results indicate that the B ring occupies a region of the binding site with fewer steric constraints. This observation is consistent with the effects of aryl substituents on thiazolidinone derivative activity. (Carlson, E. E.; May, J. F.; Kiessling, L. L. *Chem. Biol.* 2006, 13, 825-837.) These results suggest that the ring A occupies the uracil binding pocket and aryl group B resides in the sugar binding pocket of UMG. A disc susceptibility test was used to evaluate several active as well as inactive 2-aminothiazoles for growth inhibition of *M. smegmatis*. Only compounds that were found to be UGM inhibitors, blocked mycobacterial growth (FIG. 6).

To test for off-target effects, *Escherichia coli* (BL21 (DE3)), which lacks the gene encoding UGM,[8,26] was exposed to several mycobacterial growth inhibitors. None inhibited *E. coli* growth. To further characterize the observed antimycobacterial activity, minimum inhibitory concentrations (MICs) were determined for five 2-aminothiazoles with different UGM inhibitory activities. The MIC for the most potent UGM inhibitor was 50 μM, a value in the same range as the clinically used antimycobacterial agents, ethambutol and rifampicin. (Mitchison, D. A. *Eur. Respir. J.* 2005, 25, 376-379.) A direct relationship was observed between UGM inhibitor potency and the MIC. This finding suggests that the ability of the compounds to block mycobacterial growth is related to their ability to inhibit UGM.

The results support the validity of UGM as a target for antimycobacterial agents. The data indicate that compounds that block UGM can serve as new therapeutic leads for antimycobacterial agents. Our findings also highlight the utility of the 2-aminothiazole scaffold for targeting the UDP-sugar binding site of UGM. The similarity between the 2-aminothiazole and compounds found to inhibit other enzymes that act on nucleotide-sugar substrates suggests this scaffold could yield inhibitors of other UDP-sugar utilizing enzymes. (Helm, J. S.; Hu, Y.; Chen, L.; Gross, B.; Walker, S. *J. Am. Chem. Soc.* 2003, 125, 11168-11169.)

Synthetic Procedures

Phenylalanine analogs were purchased from Chem-Impex International, Inc. All other compounds and reagents were purchased from Sigma-Aldrich Co. All compounds were used as received, with the exception of solvents. Methanol was distilled from magnesium; methylene chloride and diisopropylethylamine were distilled from calcium hydride; and dimethylformamide (DMF) was used as biotech grade (Aldrich). Flash chromatography was performed using silica gel 60, 230-450 mesh (Sorbent Technologies). Analytical thin-layer chromatography (TLC) was carried out on EM Science TLC plates precoated with silica gel 60 F254 (250-μm layer thickness). Visualization of TLC plates was accomplished using a UV lamp. $^1$H NMR spectra were obtained using a Bruker AC-300 (300 MHz) or Varian MercuryPlus 300 (300

MHz), and $^{13}$C NMR specta were obtained using a Varian MercuryPlus 300 (300 MHz). Chemical shifts are reported relative to residual solvent signals (CDCl$_3$): $^1$H: δ 7.27, $^{13}$C: δ 77.23; (CD$_3$OD): $^1$H: δ 3.31, $^{13}$C: δ 49.15. $^1$H NMR data are assumed to be first order with apparent doublets and triplets reported as d and t, respectively. Multiplets are reported as m and resonances that appear broad are designated as br s. High-resolution electrospray ionization mass spectra (HRESI-MS) were obtained on a Micromass LCT.

Preparation of representative compound: 3-(4-Chlorophenyl)-2-[4-(3,5-difluoro-phenyl)-thiazol-2-ylamino]-propionic acid

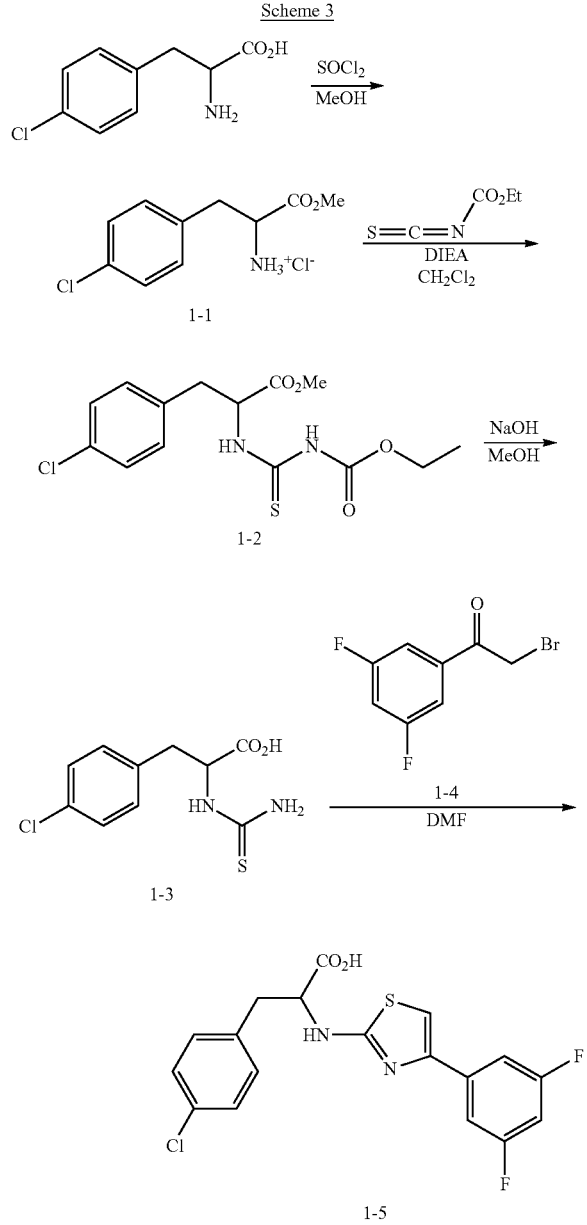

2-Amino-3-(4-chlorophenyl)-propionic acid methyl ester (1-1)

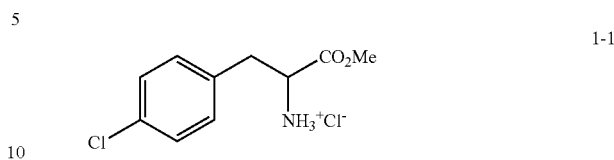

4-Chloro-DL-phenylalanine (1.00 g, 5.00 mmol) was dissolved in methanol (30 mL) and cooled to 0° C. Thionyl chloride (2.92 mL, 40.0 mmol) was added dropwise. The mixture was allowed to warm to room temperature and was heated at reflux for 4 h. The solvent and reagents were removed in vacuo to yield the hydrochloride salt 1-1 as a white powder in quantitative yield (1.25 g, 5.00 mmol). $^1$H NMR (300 MHz, CD$_3$OD): δ=7.37 (d, 2H, J=6.6 Hz), 7.27 (d, 2H, J=6.6 Hz), 4.34 (t, 1H, J=6.9 Hz), 3.81 (s, 3H), 3.26 (dd, 1H, J=14.4, 6.4 Hz), 3.18 (dd, 1H, J=14.4, 7.3 Hz); $^{13}$C NMR (75 mHz, CD$_3$OD): δ=170.28, 134.87, 134.18, 132.11, 130.19, 54.99, 53.85, 38.81; ESI-MS calcd for C$_{10}$H$_{13}$ClNO$_2$ [M+H]$^+$: 214.0635. found 214.0638.

2-[[[(ethoxycarbonyl)amino]thioxomethyl]amino]-3-(4-chlorophenyl)-propionic acid methyl ester (1-2)

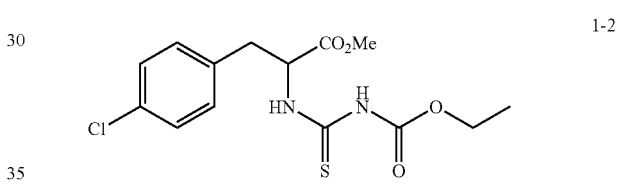

Methyl ester 1-1 (394 mg, 1.58 mmol) was dissolved in methylene chloride (4.0 mL) and diisopropylethylamine (0.82 mL, 4.73 mmol). The solution was cooled to 0° C. and ethoxycarbonyl isothiocyanate (0.21 mL, 1.73 mmol) was added dropwise. The mixture was allowed to warm to room temperature and was stirred 30 min. Methylene chloride (20 mL) was added, and the organic layer was washed with water (20 mL), 10% aqueous HCl (20 mL), and saturated brine (20 mL). The organic layer was dried with MgSO$_4$, filtered and the solvent was removed in vacuo to yield the product as a yellow oil in 92% yield (502 mg, 1.45 mmol). $^1$H NMR (300 MHz, CDCl$_3$): δ=10.10 (d, 1H, J=6.6 Hz), 8.11 (s, 1H), 7.27 (d, 2H, J=8.1 Hz), 7.10 (d, 2H, J=8.1 Hz), 5.25 (t, 1H, J=6.3 Hz), 4.23 (q, 2H, J=7.2 Hz), 3.73 (s, 3H), 3.32 (dd, 1H; J=14.1, 6.0 Hz), 3.20 (dd, 1H, J=13.8, 6.0 Hz), 1.30 (t, 3H, J=7.2 Hz); $^{13}$C NMR (75 mHz, CDCl$_3$): δ=179.4, 170.8, 152.6, 134.2, 133.4, 130.8, 129.0, 63.2, 59.2, 53.6, 52.8, 36.8, 14.4; ESI-MS calcd for C$_{14}$H$_{17}$ClN$_2$O$_4$S [M+Na]$^+$: 267.0495. found 267.0495.

3-(4-Chlorophenyl)-2-thioureido-propionic acid 1-3)

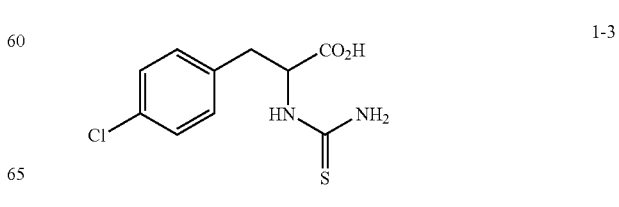

Compound 1-2 (500 mg, 1.45 mmol) was dissolved in a 1:1 solution of 1 M NaOH and MeOH (6 mL). The solution was heated to reflux for 30 min. The solution was acidified to a pH of 3 using 1 M HCl and then extracted using EtOAc (3×15 mL). The combined organic extracts were dried with $MgSO_4$ and filtered. The solvent was removed in vacuo to yield 1-3 as a white solid in quantitative yield (372 mg, 1.44 mmol). $^1$H NMR (300 MHz, $CD_3OD$): δ=7.27 (d, 2H, J=8.4 Hz), 7.19 (d, 2H, J=8.4 Hz), 5.20 (m, 1H), 3.31 (dd, 1H, J=13.5, 6.5 Hz), 3.08 (dd, 1H, J=13.5, 6.3 Hz); $^{13}$C NMR (75 mHz, $CD_3OD$): δ=185.0, 174.6, 136.9, 133.9, 132.2, 129.6, 59.4, 38.2; ESI-MS calcd for $C_{10}H_{11}ClN_2O_2S$ [M−H]$^−$: 257.0152. found 257.0155.

2-Bromo-3',5'-difluoro-acetophenone (14)

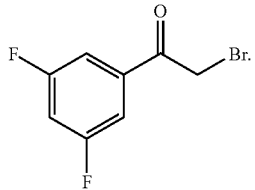

1-4

A solution of $CuBr_2$ (2.36 g, 10.6 mmol) in EtOAc (3 mL) was heated to reflux. A solution of 3',5'-difluoroacetophenone (1.00 g, 6.4 mmol) in $CHCl_3$ (3 mL) was added dropwise. The solution was stirred at reflux until all $CuBr_2$ appeared to be consumed (precipitate turns white), about 1 h. The solution was filtered and concentrated, and the product was purified by silica column chromatography (3→5% EtOAc in hexanes) to yield 1-4 in 61% yield (0.92 g, 3.91 mmol). $^1$H NMR (300 MHz, $CDCl_3$): δ=7.49 (m, 2H), 7.07 (m, 1H), 4.38 (s, 2H); $^{13}$C NMR (75 mHz, $CDCl_3$): δ=189.2, 165.0 (d, 1C, J=12.4 Hz), 161.6 (d, 1C, J=11.5 Hz), 136.9 (t, 1C, J=7.9 Hz), 112.2 (d, 2C, J=26 Hz) 109.5 (t, 1C, J=25 Hz), 30.2; EI-MS calcd for $C_8H_5BrF_2O$ [M+]$^+$: 233.9492. found 233.9484.

3-(4-Chlorophenyl)-2-[4-(3,5-difluoro-phenyl)-thiazol-2-ylamino]-propionic acid (1-5)

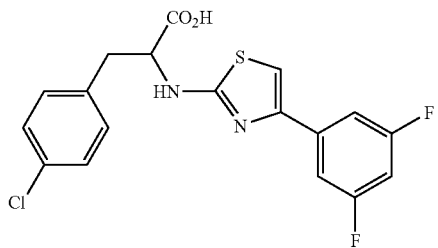

1-5

Thiourea 1-3 (20 mg, 77 μmol) and α-bromoketone 1-4 (20 mg, 85 μmol) were combined in DMF (150 μL). The reaction was stirred under $N_2$ for 2 h and concentrated; the product was purified by silica gel chromatography (2:1 hexanes/EtOAc→2:1 hexanes/EtOAc containing 2% AcOH) to yield 1-5 (19.8 mg, 50 μmol) as a white powder in 65% yield. $^1$H NMR (300 MHz, $CD_3OD$): δ=7.39 (dd, 2H, J=9, 2.4 Hz), 7.26 (s, 4H), 7.02 (s, 1H), 6.81 (tt, 1H, J=9.3, 2.1 Hz), 4.72 (dd, 1H, J=7.8, 5.1 Hz), 3.31 (dd, 1H, J=13.8, 5.4 Hz), 3.10 (dd, 1H, J=13.8, 8.1 Hz); $^{13}$C NMR (75 mHz, $CD_3OD$): δ=173.2, 167.2, 164.4 (d, 1C, J=13.3 Hz), 160.9 (d, 1C, J=13.8 Hz), 147.1, 138.1 (t, 1C, J=10.3 Hz), 136.6, 131.2, 131.0, 128.1, 108.3 (d, 2C, J=25.6 Hz), 104.8, 102.4 (t, 1C, J=25.0 Hz), 58.4, 36.2; ESI-MS calcd for $C_{18}H_{13}ClF_2N_2O_2S$ [M−H]$^−$: 393.0276. found 393.0266.

Binding Data

Figure 5A:
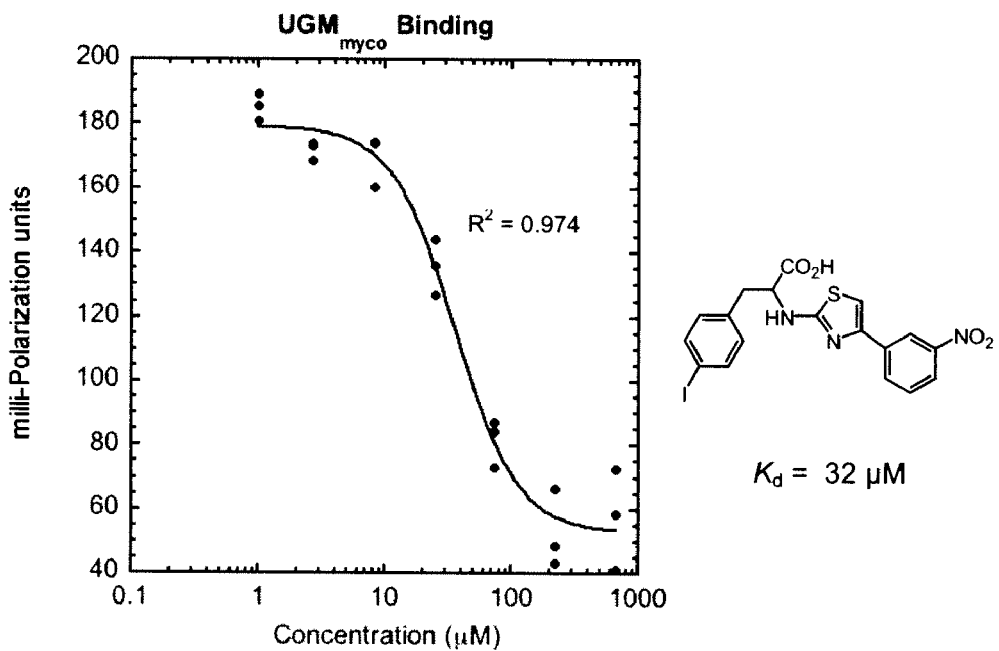
FIGS. 5A and 5B are graphs illustrating exemplary binding curves as determined by the fluorescence polarization assay.
Figure 5B:
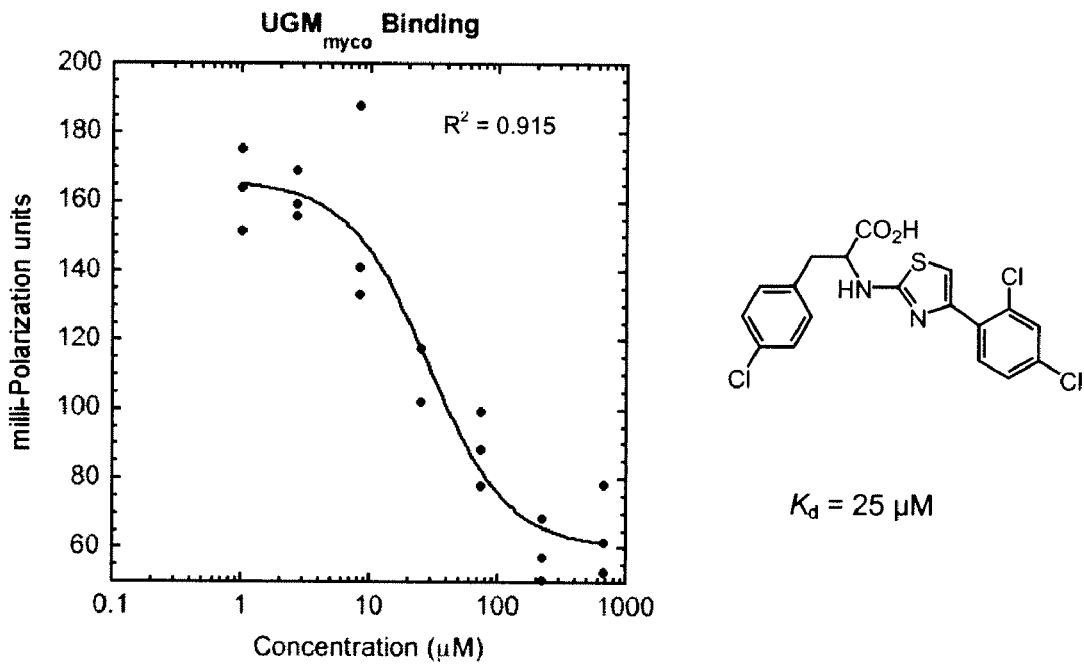
Figures 1, 7:
FIG. 7 (pages 1 to 5) is a Table of exemplary binding data as determined by the fluorescence polarization assay. Binding is shown for the UGM isoform from *K. pneumoniae* (K) and *M. tuberculosis* (M). Dissociation constants are given in units of µM. The data in FIG. 7 depicts the effects of varying the B ring substitution in compounds of structure.
Figures 3, 7:
FIG. 3 illustrates a comparison of the shape of a thiazolidinone scaffold to that of a 2-aminothiazole scaffold using an overlay of minimized thiazolidinone scaffold (top) and novel 2-aminothiazole scaffold (bottom). Exemplary chemical structures are also illustrated.
Figures 5, 7:
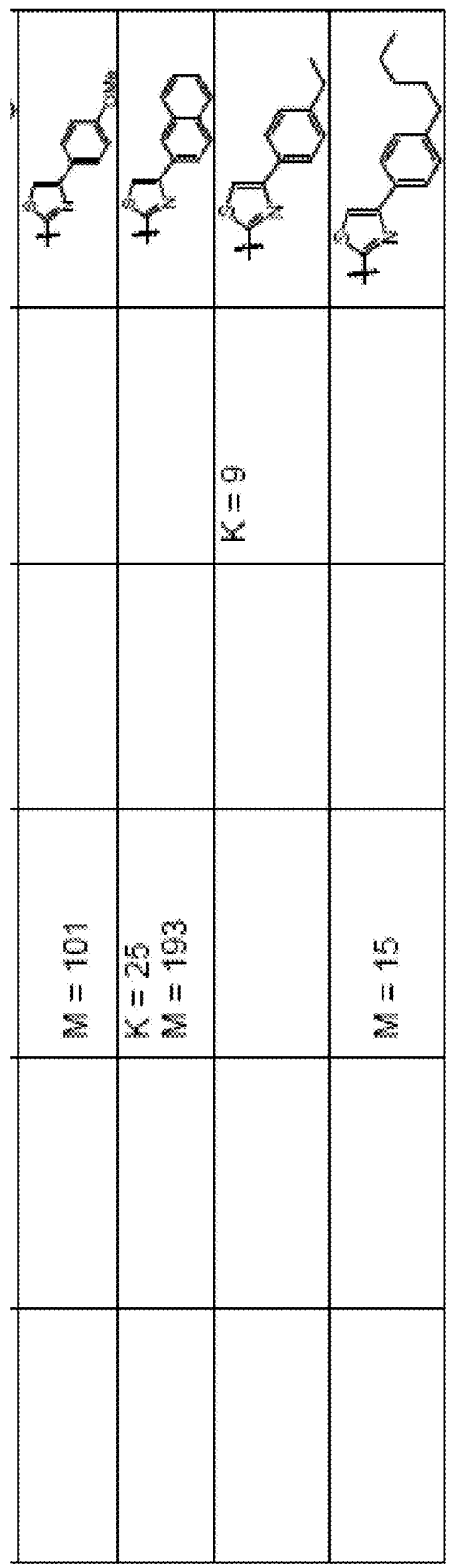

The fluorescence polarization assay to determine binding affinity was performed as described previously. (Carlson, E. E.; May, J. F.; Kiessling, L. L. Chem. Biol. 2006, 13, 825-837.) Representative binding curves are depicted in FIGS. 5A and 5B. Exemplary binding data as determined by the fluorescence polarization assay is provided in the Tables in FIG. 6, pages 1 to 4 and FIG. 7, pages 1 to 5. Binding is shown for the UGM isoform from K. pneumoniae (K) and M. tuberculosis (M). Dissociation constants are given in units of μM. FIG. 6 depicts the effects of varying the A ring substitution and FIG. 7 the effects of varying the B ring substitution in compounds of structure:

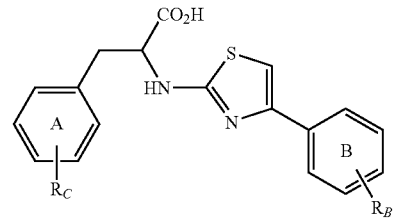

Activity Data $UGM_{myco}$ inhibition was assessed using a previously described HPLC assay to measure the extent of enzymatic conversion of UDP-galactofuranose to UDP-galactopyranose. (Carlson, E. E.; May, J. F.; Kiessling, L. L. Chem. Biol. 2006, 13, 825-837.)

Figure 8:
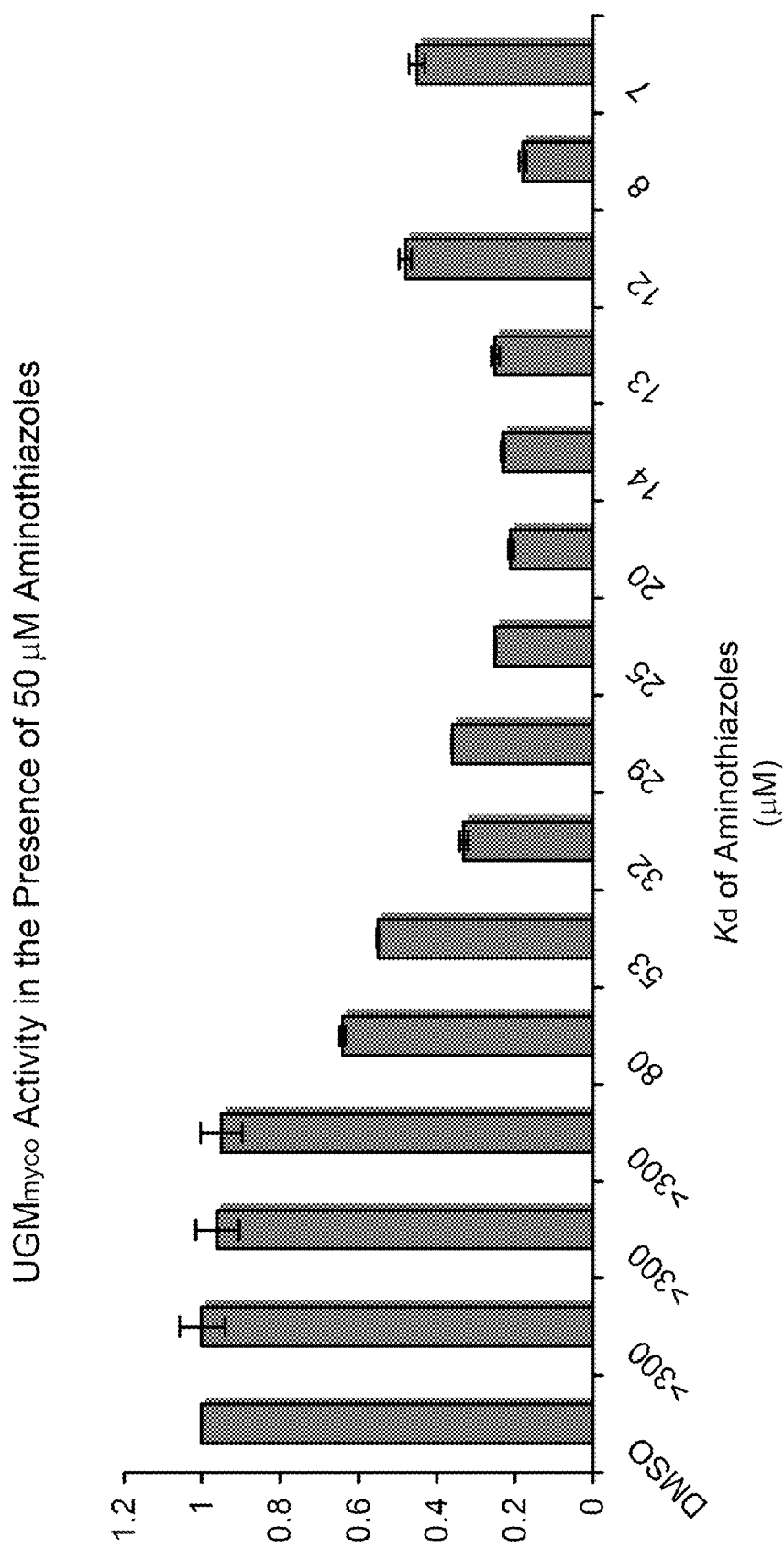
FIG. 8 is a graph illustrating the relationship between $UGM_{myco}$ Activity and $K_d$ for exemplary aminothiazoles.

The relative activity of $UGM_{myco}$ in the presence of DMSO alone was compared to that in the presence of 50 μM of selected aminothiazoles. Enzymatic reaction conditions were as follows: 50 μM UDP-Galf, 4 μM $UGM_{myco}$ and 20 mM DTT in 4% DMSO v/v. The mean activity of UGM±the standard deviation are shown in FIG. 8 for three replicates. The mean activities of $UGM_{myco}$ in the presence of the aminothiazoles are presented in order of decreasing binding affinities to highlight the relationship between enzyme inhibition and binding affinity.

Figure 9A:
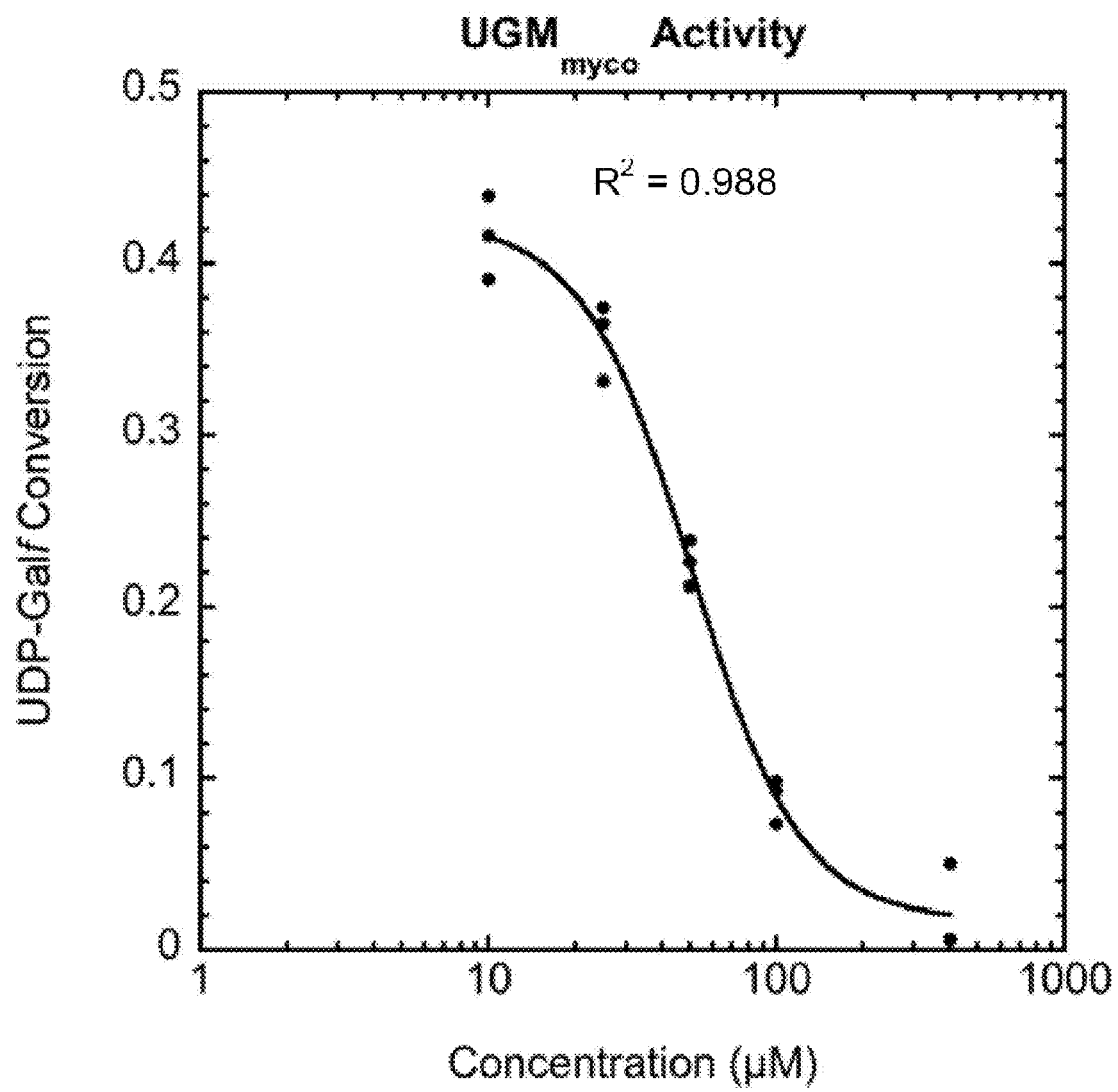
FIGS. 9A and 9B are representative dose-response inhibition curves for two mycobacterial growth inhibitors whose structures are illustrated. The inhibition curves look similar to the binding curves depicted in FIGS. 5A and 5B, above. The $IC_{50}$ values are comparable, albeit slightly higher than the $K_d$ values. In the graphs of these figures, conversion is the amount of UDP-Galp formed divided by the amount of total UDP-Gal (UDP-Galp+UDP-Galf).
Figure 9A:
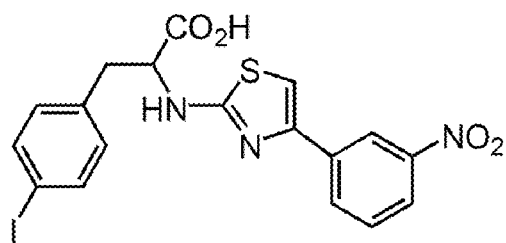
Figure 9B:
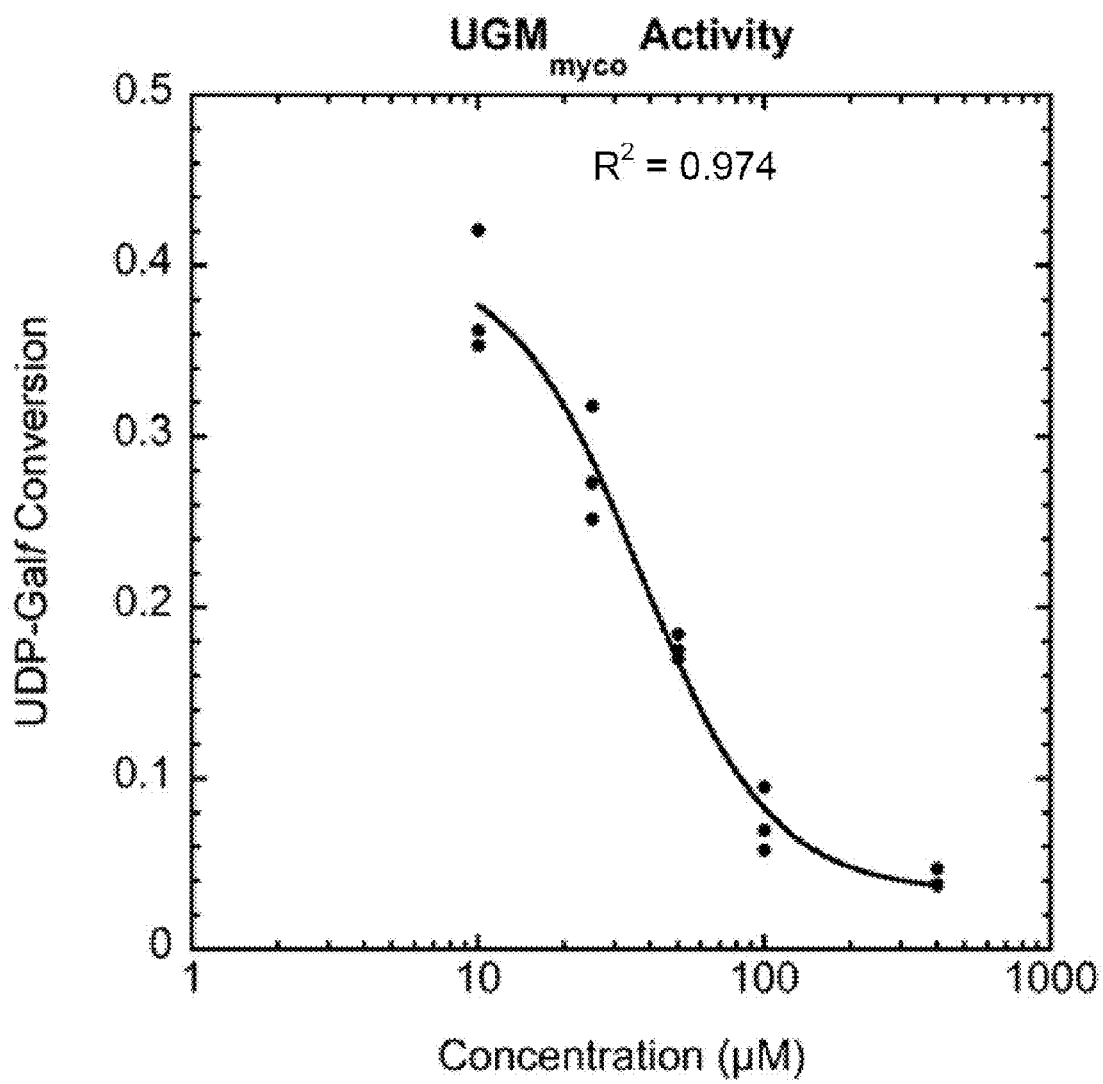
Figure 9B:
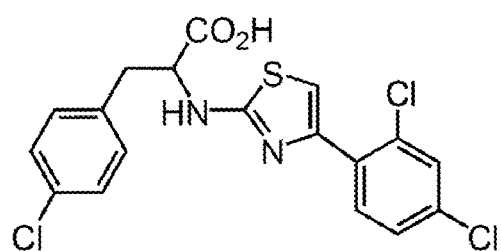

Representative dose-response inhibition curves for two mycobacterial growth inhibitors at provided in FIGS. 9A and 9B. The inhibition curves look similar to the binding curves depicted in FIGS. 5A and 5B. The $IC_{50}$ values are comparable, albeit slightly higher than the $K_d$ values. In the graphs of these figures, conversion is the amount of UDP-Galp formed divided by the amount of total UDP-Gal (UDP-Galp+UDP-Galf). The data were fit to the equation as previously described. (Soltero-Higgin, M.; Carlson, E. E.; Phillips, J. H.; Kiessling, L. L., Identification of inhibitors for UDP-galactopyranose mutase. J. Am. Chem. Soc. 2004, 126, 10532-10533.)

Figure 10A:
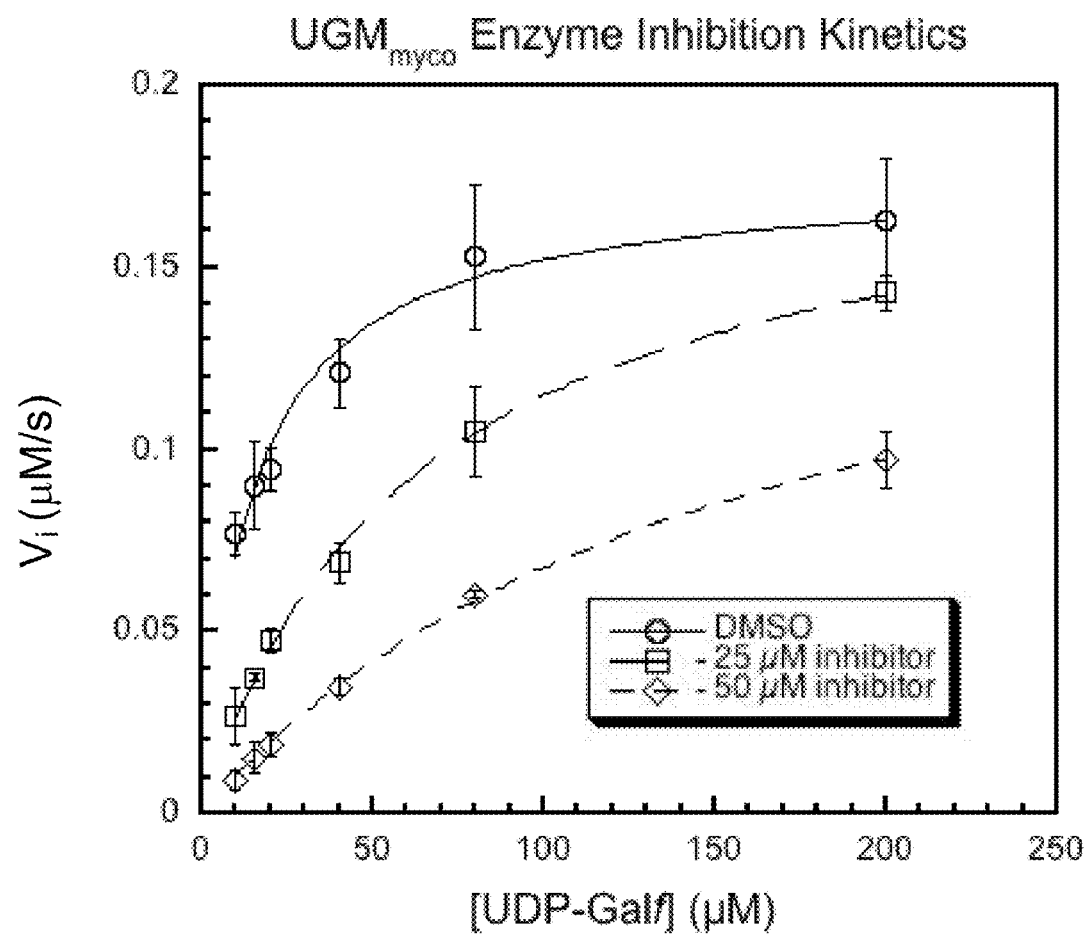
FIGS. 10A and 10B illustrate an exemplary graph of enzyme inhibition kinetics and a double reciprocal plot, respectively for a compound of the invention.
Figure 10B:
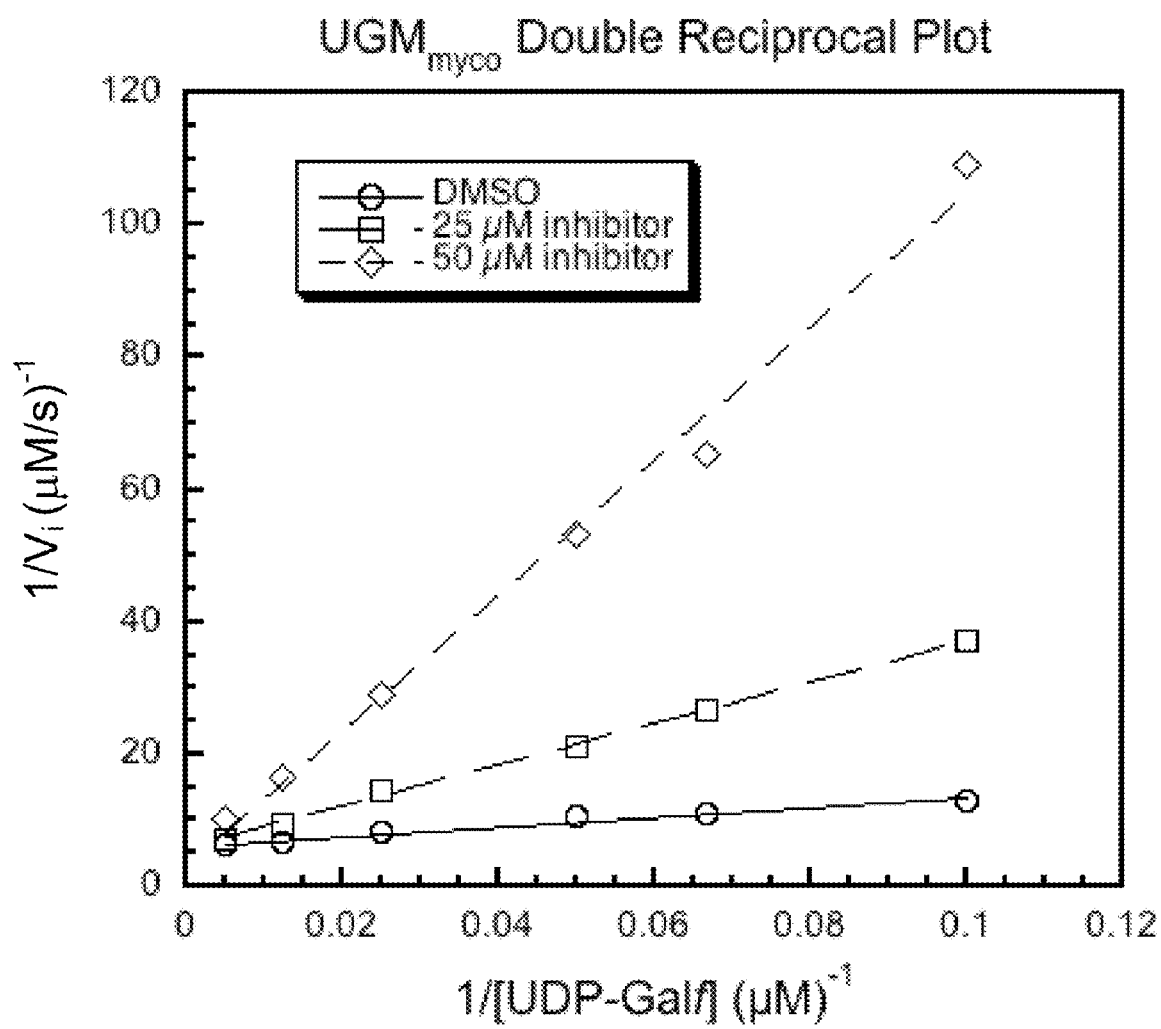

For inhibitor kinetic assays, the initial rate of $UGM_{myco}$ was determined at various UDP-Galf concentrations in the presence of either DMSO alone (4% v/v), 25 µM inhibitor, or 50 µM inhibitor. Enzymatic reaction conditions were as follows: 50 mM sodium phosphate buffer (pH 7), 20 mM sodium dithionite, 11 nM $UGM_{myco}$, UDP-Galf, and inhibitor or DMSO in a total volume of 60 µL. Reactions were initiated upon $UGM_{myco}$ addition and were quenched by the addition of an 60 µL of 1:1 MeOH:CHCl$_3$. Product formation was analyzed using a HPLC-based assay. (Carlson, E. E.; May, J. F.; Kiessling, L. L. *Chemistry & Biology* 2006, 13, 825-837.) FIGS. 10A and 10B illustrate an exemplary graph of enzyme inhibition kinetics and a double reciprocal plot, respectively, or compound:

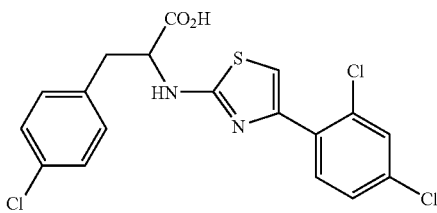

where $K_i$=5.3 µM.

Mycobacterial Growth Inhibition—Disc Assay
Sterile cloning discs (3 mm diameter) were obtained from ThermoFisher Scientific, Inc. DMSO was obtained from Sigma-Aldrich Chemical Co. To test for growth inhibition of *Mycobacterium smegmatis* or *Escherichia coli*, LB (Luria-Bertani) medium was inoculated with *M. smegmatis* (ATCC number 700084) or *E. coli* BL21 (DE3) and incubated at 37° C. (about 2 days for *M. smegmatis*, about 6 hours for *E. coli*). The culture was diluted to $OD_{600}$=0.2 in LB and was spread (100 µL) on LB agar plates. Cultures were allowed to soak into the plates for approximately one hour. Then, sterile discs (3 mm diameter), to which either DMSO (2 µL) or compound dissolved in DMSO (2 µL, 16 nmol) had been added, were placed onto the surface of the agar. Plates were incubated overnight at 37° C., then at room temperature for several additional days. In both assays, a disc with kanamycin (2.5 µg, 4.3 nmol) was included as a positive control.

The Table in FIG. 11, pages 1 to 3, provides exemplary data for the indicated compounds which compares $K_d$($UGM_{myco}$), relative $UGM_{myco}$ activity at 50 µM and the qualitative results of bacterial growth disc assays. All aminothiazoles tested that inhibited $UGM_{myco}$, as determined by the activity assay, also inhibited bacterial growth, whereas aminothiazoles that did not show inhibition of $UGM_{myco}$ did not inhibit bacterial growth.

Figure 12B:
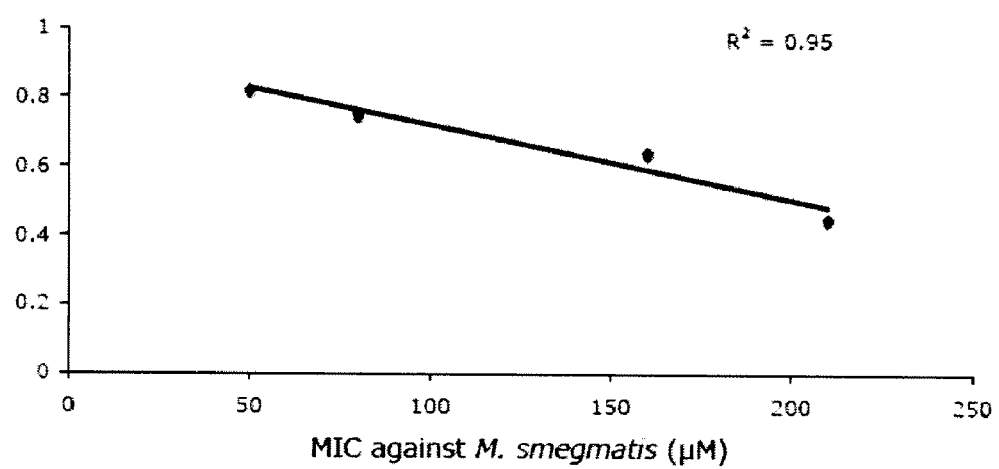
FIG. 12B provides a graph illustrating the correlation between MIC values and UGM inhibition.

Standard agar dilution technique to determine minimum inhibitory concentration (MIC) values. MIC values for representative aminothiazoles were determined using standard agar dilution methods in 48-well plates. Each well contained 0.5 mL LB agar medium with 3 µL of compound dissolved in DMSO or with 3 µL of DMSO alone as the control. Wells were inoculated with 10 µL of *M. Smegmatis* culture that was diluted to give an $OD_{600}$ of 0.03. Plates were incubated at 37° C. for 48 h. The MIC was defined as the lowest concentration of aminothiazole at which no visible growth was observed. The MIC was determined within 10 µM. Exemplary MIC data are presented in the table of FIG. 12A. A graph illustrating the correlation between MIC values and UGM inhibition is provided in FIG. 12B.

Example 2

Potent Ligands for UGM that Exploit an Enzyme Subsite

This example relates to highly potent ligands for UGM which are believed to access both the substrate binding pocket of UGM and an adjacent site on the enzyme. In previous work, we identified inhibitors of UGM using a high throughput screen based upon fluorescence polarization (Soltero-Higgin, M.; Carlson, E. E.; Phillips, J. H.; Kiessling, L. L. *J. Am. Chem. Soc.* 2004, 126, 10532-10533.). In designing the fluorescent probe employed in that work (compound 1A, above) a certain fluorophore was coupled to UDP through the diphosphate linkage. A hexanolamine linker was used to minimize any destabilizing effect from the fluorescein moiety. The probe was found to bind to UGM from *Klebsiella pneumoniae* ($UGM_{kleb}$) with an affinity of 0.10 µM and to UGM from *Mycobacterium tuberculosis* ($UGM_{myco}$) with an affinity of 0.16 µM; thus, its affinity is approximately 100-fold better than that of UDP. The present work relates to the synthesis and assessment of UGM ligands comprising multiple ring moieties, such as fluorescein and the further assessment of the ability of such compounds to inhibit microbial growth.

The effect of the length of the linker separating fluorescein and the UDP moiety on binding was assessed. A panel of UDP-fluorescein derivatives in which the linker length was varied was synthesized. A series of amine-containing linkers were appended through the pyrophosphate group to afford UDP derivatives with alkyl linker lengths of two, four, six, eight, and ten methylene units (Scheme 4). (Vincent, S. P.; Gastinel, L. N. *Carbohydr. Res.* 2002, 337, 1039-1042.) These linkers were assembled from commercially available amino alcohols, which were first converted to trifluoroacetamides 1a-1e. These compounds were treated with dibenzyl phosphate to yield the phosphotriesters 2a-2e. Hydrogenolysis of the benzyl groups afforded the phosphates 3a-3e as the triethylamine salts, and these were coupled to uridine 5'-monophosphate (UMP)—N-methylimidazolide. The trifluoroacetamide group was removed and UDP derivatives 4a-4e were treated with fluorescein isothiocyanate (FITC) to yield conjugates 5a-5e.

The affinities of the UDP-fluorescein conjugates for $UGM_{kleb}$ and $UGM_{myco}$ were determined using fluorescence polarization and are listed for compounds 5a-5e where n is 1, 3, 5, 7 or 9, respectively. UDP binds to $UGM_{myco}$ with a $K_d$ of 15 µM and to $UGM_{kleb}$ with a $K_d$ of 26 µM. The dissociation constants of derivatives 5a-5e for either $UGM_{kleb}$ or $UGM_{myco}$ depend on linker length. Specifically, compound 5a (two methylene linker) binds poorly ($K_d$>30 µM); conjugate 5b (four methylene linker) is slightly (5-fold) more potent than UDP. Conjugate 5c (six methylene linker) binds 100-fold better, while 5d (eight methylene linker) bound with the highest affinity: 500-fold tighter than UDP. The eight methylene linker seems to provide the necessary distance for optimal binding; the affinity of 5e (ten methylene linker) for UGM is similar than that of 5d.

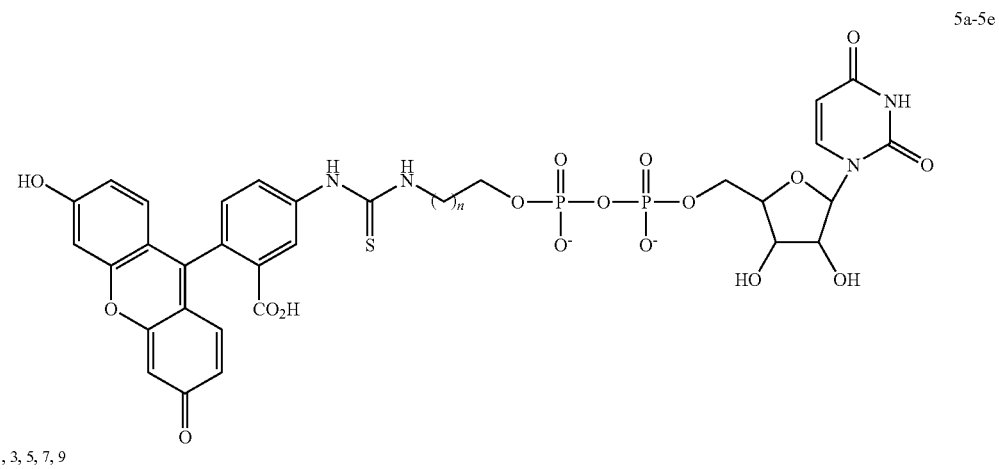

n = 1, 3, 5, 7, 9

TABLE 1

| n | UGM$_{myco}$ K$_d$ (μM) |
|---|---|
| 1 | >30 |
| 3 | 2.5 |
| 5 | 0.17 |
| 7 | 0.054 |
| 9 | 0.064 |
| UDP | 15 |

The dependence of binding affinity on linker length suggests there is a subsite that the fluorophore occupies and the eight methylene linker provides the means to access this site. Ligands that exploit this subsite are highly potent. In view of the dramatic effect of linker length on ligand binding the affect of the chemical nature of the linker was assessed. Compound 4d, which is lacking a fluorophore, has a similar affinity for UGM as UDP. These data suggest that the linker has little influence on binding in the absence of the fluorophore. To test whether the chemical composition of the linker contributes to the affinity of the fluorophore-containing UDP derivatives, we analogs possessing oligoethyleneglycol linker were synthesized. Triethylene glycol and tetraethylene glycol were monomesylated and converted to the corresponding azide (Vincent, S. P.; Gastinel, L. N. *Carbohydr. Res.* 2002, 337, 1039-1042.). The azides were reduced to the corresponding amine via catalytic hydrogen and converted to UDP-fluorescein conjugates 5f and 5g (Scheme 5).

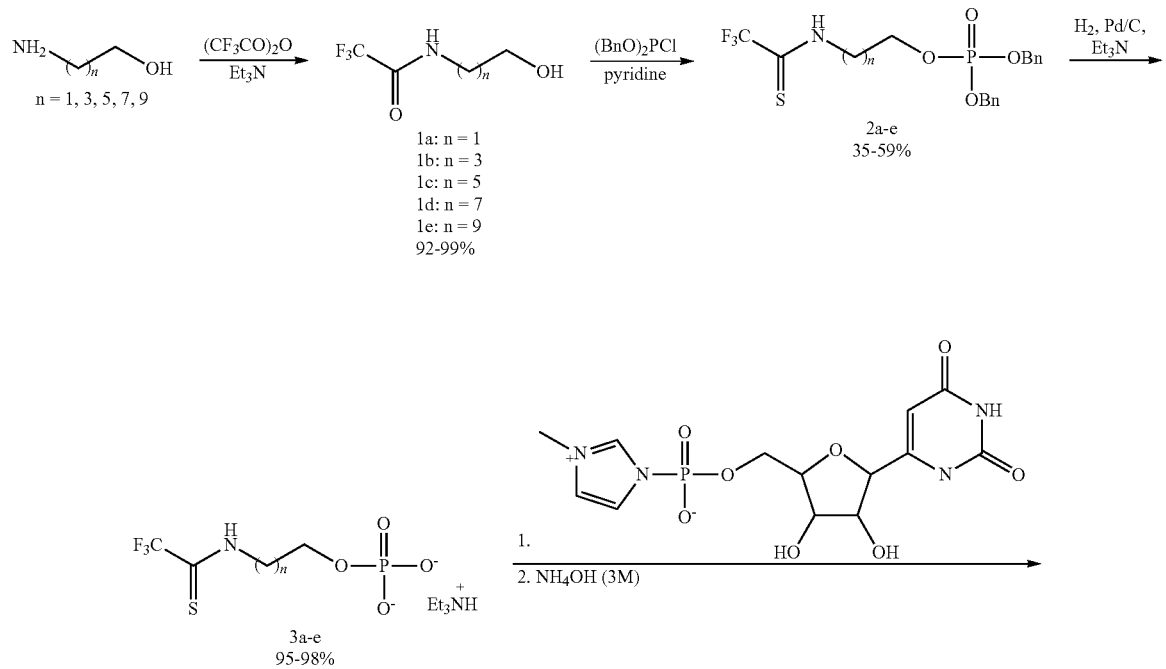

Scheme 4. Synthesis of UDP-fluorescein conjugates containing alkyl linkers

-continued

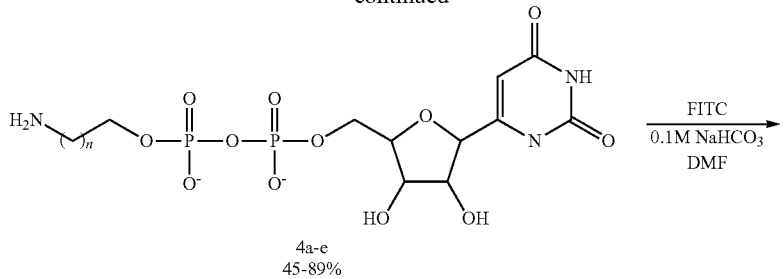

4a-e
45-89%

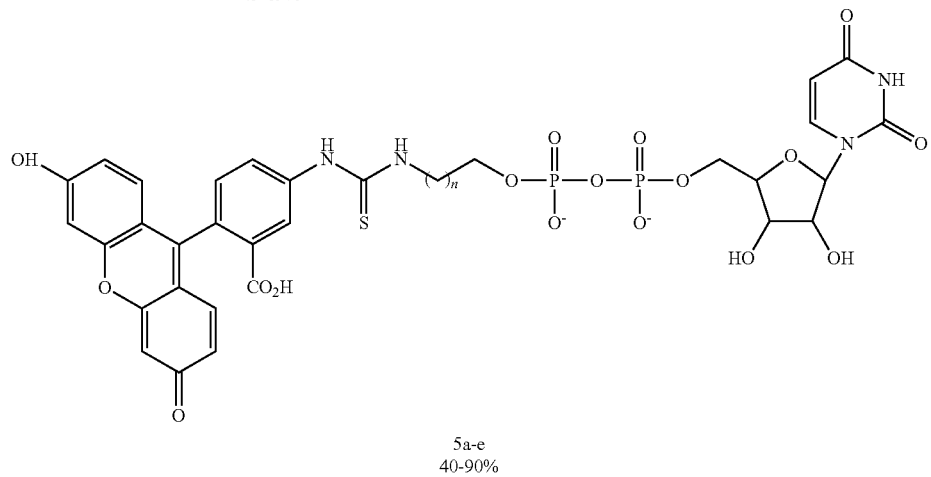

5a-e
40-90%

For UGM$_{myco}$, 5f bound with 20-fold greater affinity than UDP, but its affinity was more than 10-fold lower than the conjugate with the alkyl linker of similar length (compound 5d, eight methylene linker). A similar trend was observed with UGM$_{kleb}$. This discrepancy in the affinity of the oligoethylene glycol conjugate and the alkyl conjugate of similar length could be due to differences in conformation affecting their length in solution (Karlsson, L.; Asbrink, L.; Fridh, C.; Lindholm, E.; Svensson, A. Phys. Scr. 1980, 21, 170-172.) Specifically, the gauche effect will influence the conformation of oligoethylene glycol linkers. Still, conjugate 5g with a longer oligoethylene glycol linker did not exhibit improved binding to either UGM$_{kleb}$ or UGM$_{myco}$. These results indicate that the nature of the linker plays a role in the binding of UDP-fluorescein compounds to UGM.

To investigate whether binding of the fluorophore alone could be detected, fluorescein derivative 6, which possesses a linker from FITC and octanolamine, was synthesized (Scheme 6). Interestingly, no binding was observed at concentrations up to 34 µM of either UGM$_{myco}$ or UGM$_{kleb}$. Similarly, no binding was observed when UGM was first incubated with 200 µM of UDP. This result indicates that the UDP moiety and the fluorophore must be linked. Given that fluorescein contributes significantly to binding, other aryl substituents were investigated. Specifically, UDP-octanolamine 4d was appended to naphthyl isothiocyanate to form conjugate 7 (Scheme 7). While the affinity of naphthyl conjugate 7 for UGM was 10-fold less than the corresponding fluorescein conjugate 5d, it was 25-fold greater than UDP alone. These results suggest that the naphthyl group can occupy the subsite exploited by the fluorescein group.

As described above, certain 2-aminothiazoles were found to be competitive inhibitors of UGM. Experiments were performed to assess whether the affinity of 2-aminothiozoles for UGM could be increased by exploiting the identified subsite.

As a starting point, analogs of 2-aminothiazole 8, which has a pentyl substitutent, and has an UGM affinity of 15 µM, was synthesized. A fluorescein group was attached to this 2-aminothiozole via elaboration of the pentyl group. As illustrated in Scheme 8 an analog with an eight methylene linker terminating in an amine was prepared, for the conjugation of a fluorophore.

More specifically, the synthesis of aminothiazole 11 began with a Friedel-Crafts acylation of 8-phenyl-1-octanol to produce the acetophenone. (Hernandezgallegos, Z.; Lehmann, P. A. J. Med. Chem. 1990, 33, 2813-2817.) The alcohol was converted to the azide through the mesylate followed by α-bromination with CuBr$_2$ to provide 9. (King, L. C.; Ostrun, G. K. J. Org. Chem. 1964, 29, 3459-3461.) The α-bromoketone 9 was cyclized with the thiourea derived from 4-chloro phenylalanine to generate 2-aminothiazole 10. The azide was reduced with catalytic hydrogenation to afford the amine, which was conjugated to fluorescein isothiocyanate (FITC). The affinity of fluorescein conjugate 11 is 0.38 µM for UGM$_{kleb}$ and 0.30 µM for UGM$_{myco}$. Thus, this substituted aminothiazole binds between 40 and 50-fold more tightly than thiazole 8 alone.

In summary, we have identified highly potent UGM ligands, having binding affinities of ~50 nM., which possess aryl substituents linked to an aminothiazole, which are believed to access a subsite present on the UGM from K. pneumoniae and M. tuberculosis.

General Synthetic Procedures

All reagents were purchased from Sigma-Aldrich Co., except for octanolamine and decanolamine, which were purchased from TCI America. All compounds were used as received. Methanol (MeOH) was distilled from magnesium, methylene chloride (CH$_2$Cl$_2$) and diisopropylethylamine (DIEA) were distilled from calcium hydride, and dimethyl formamide (DMF) was used as biotech grade (Sigma-Aldrich Co.).

Flash chromatography was performed using silica gel 60, 230-450 mesh (Sorbent Technologies). Analytical thin-layer chromatography (TLC) was carried out on EM Science TLC plates precoated with silica gel 60 F254 (250-μm layer thickness). Visualization of TLC was accomplished using a UV lamp.

$^1$H NMR spectra were obtained using a Bruker AC-300 (300 mHz) or Varian MercuryPlus 300 (300 MHz), and $^{13}$C NMR specta were obtained using a Varian MercuryPlus 300 (300 MHz). Chemical shifts are reported relative to residual solvent signals (CDCl$_3$): $^1$H: δ 7.27, $^{13}$C: δ 77.23; (CD$_3$OD): $^1$H: δ 3.31, $^{13}$C: δ 49.15; (DMF-d$_7$): $^1$H: δ 2.92, $^{13}$C: δ 34.89; (D$_2$O): $^1$H: δ 4.79. $^1$H NMR data are assumed to be first order with apparent doublets and triplets reported as d and t, respectively. Multiplets are reported as m and resonances that appear broad are designated as br.

Scheme 6: Synthesis of linker-fluorescein conjugate 6.

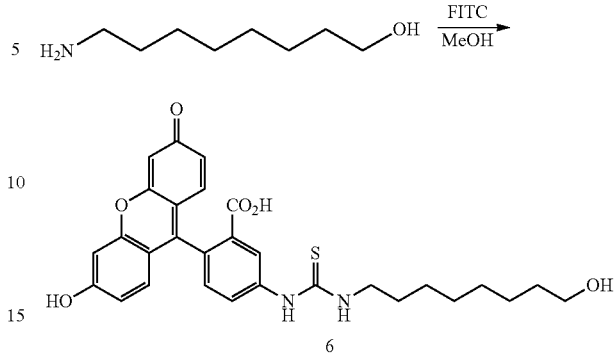

Scheme 5: Synthesis of UDP-fluorescein conjugates containing ethylene glycol based linkers

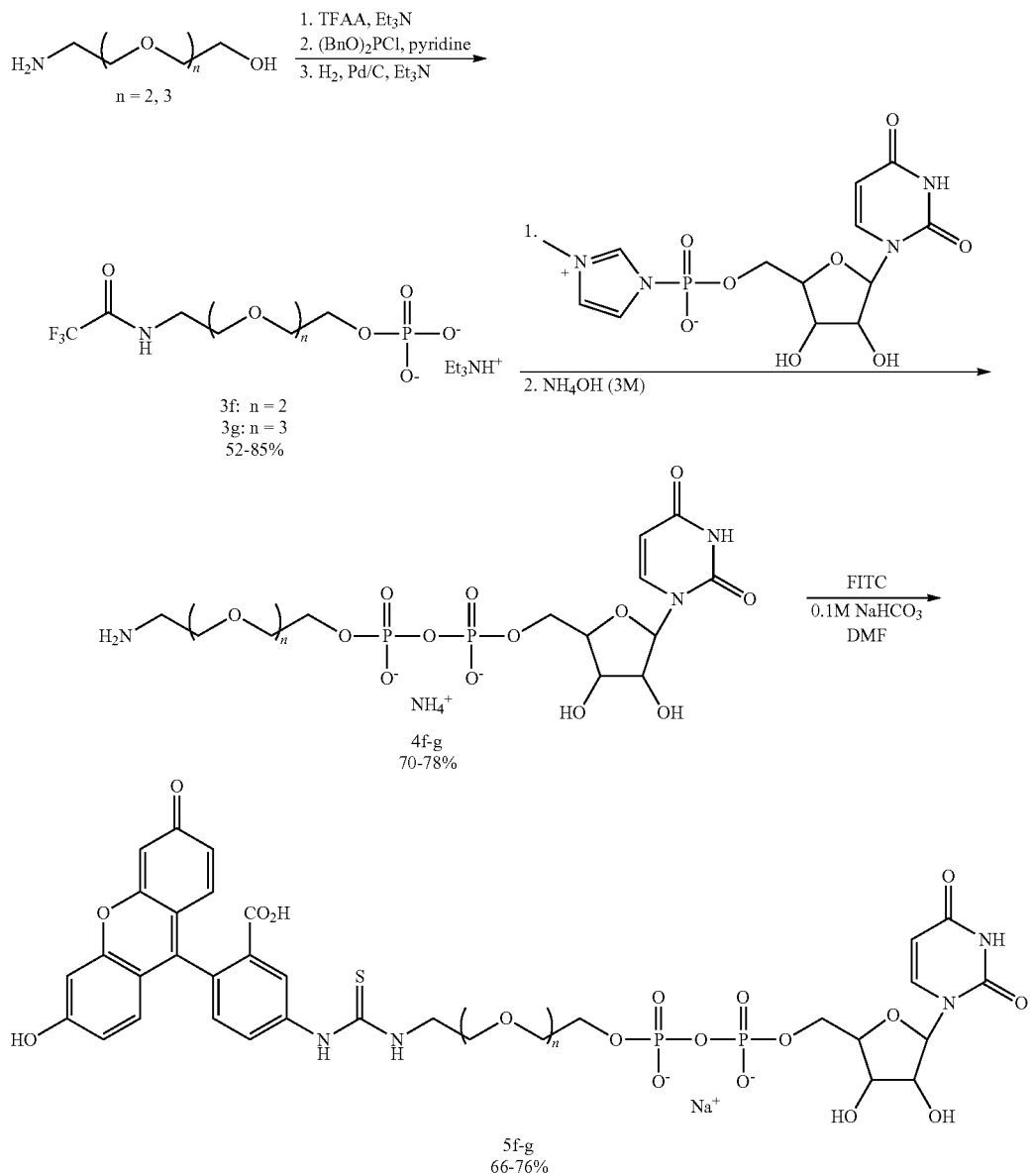

Scheme 7: Synthesis of UDP-naphthyl conjugate 7.
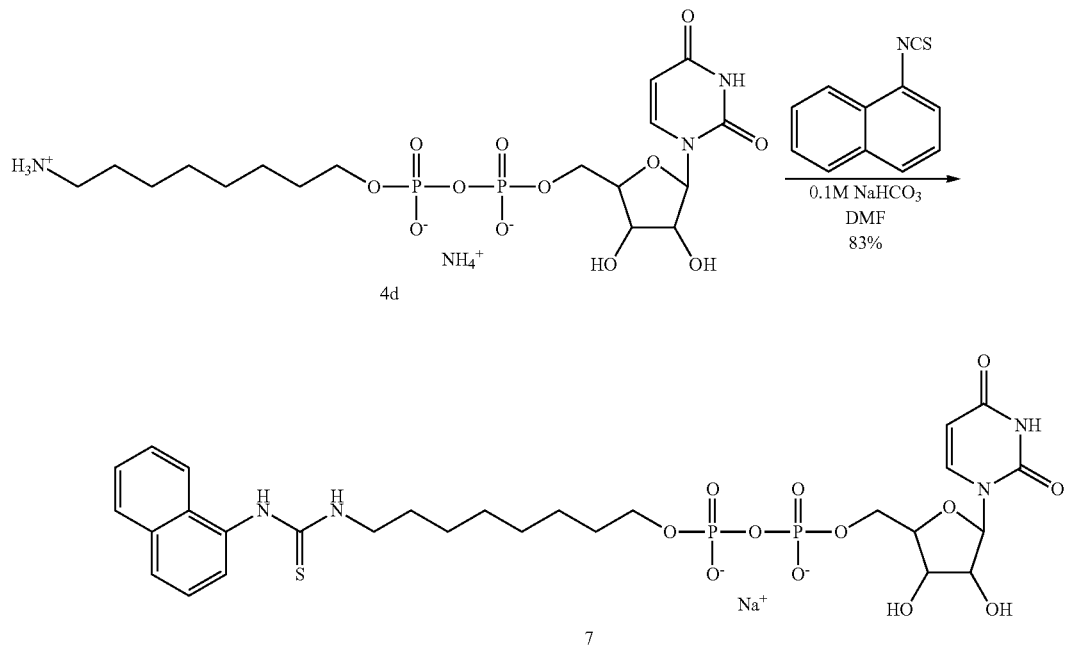
Scheme 8. Synthesis of UGM inhitibor conjugated to fluorescein
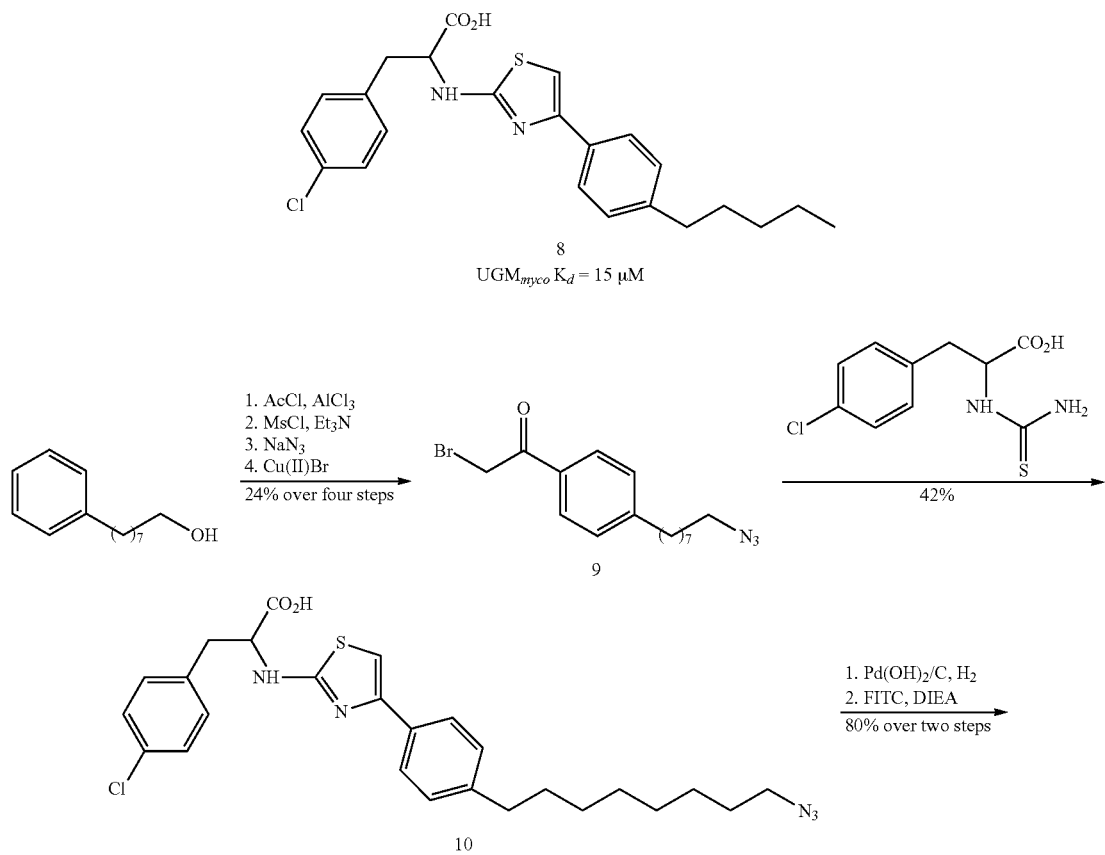

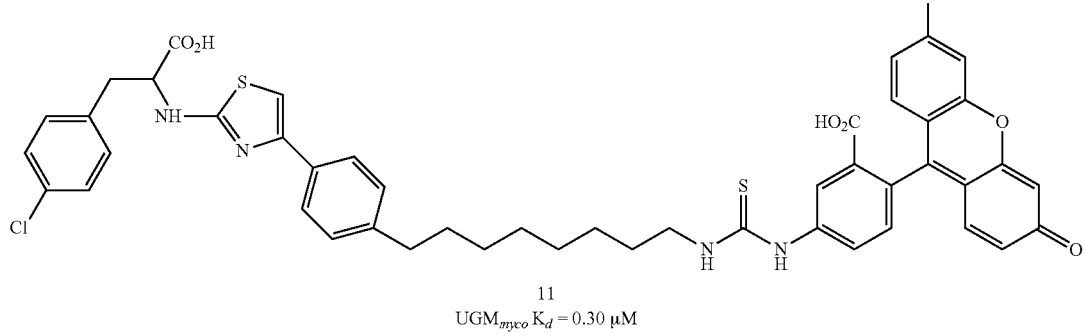

11
UGM$_{myco}$ K$_d$ = 0.30 μM

High-resolution electrospray ionization mass spectra (HRESI-MS) were obtained on a Micromass LCT. LC-MS (ESI) were obtained using a Shimadzu LCMS-2010 (Columbia, Md.) equipped with two pumps (LC-10Advp), controller (SCL-10Avp), autoinjector (SIL-10Advp), UV diode array detector (SPD-M10Avp), and single quadrupole analyzer (by electrospray ionization, ESI). The LC-MS is interfaced with a PC running the Shimadzu LCMS solution software package (Version 2.04 Su2-H2). A Supelco (Bellefonte, Pa.) 15 cm×2.1 mm C-18 wide pore reverse phase column was used for all LC-MS analyses. Standard reverse phase HPLC conditions were used as follows: flow rate=200 mL/min; mobile phase A=0.1% formic acid; mobile phase B=0.1% formic acid in acetonitrile, 50-95% B over 7 min. UV spectra were recorded using an HP-8452 UV-Vis spectrometer running UV Visible Chemstation software. High performance liquid chromatography (HPLC) was performed on a C18 reverse phase column using water (A) and acetonitrile (B) (both buffered with 0.02% trifluoroacetic acid) as the elution solvents at 10 mL/min. Compound elution was detected by UV absorbance at range 200-600 nm.

Cation-exchange resin Dowex 50WX8-200 (H+ form, strongly acidic) was purchased from Aldrich and converted to the appropriate salt form prior to use. Uridine 5'-monophosphate (5'-UMP) disodium salt was purchased from Sigma and converted to the triethylammonium salt (1.4 eq by $^1$H NMR) prior to coupling reactions by stirring with Dowex 50WX8-200 (NEt$_3$H$^+$ form) overnight. The resin was removed by filtration and washed with H$_2$O. Combined filtrates were lyophilized to produce the UMP-Et$_3$NH$^+$ salt as a fluffy white solid.

General Procedure I:
The installation of the trifluoracetamide protecting group.
A solution of amino alcohol (1.0 eq) and triethylamine (2.5 eq) in MeOH was cooled to 0° C. Trifluoroacetic anhydride (1.4 eq) was added dropwise under an argon atmosphere and the reaction was allowed to warm to room-temperature. The solution was stirred 4 h, concentrated, and the product was purified by silica gel chromatography to afford 1.

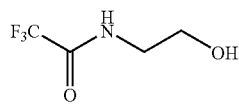

1a

2-Trifluoroacetamido-1-ethanol (1a): Following general procedure I, ethanolamine (2.0 g, 32.74 mmol) was combined with triethylamine (11.4 mL, 81.86 mmol) and trifluoroacetic anhydride (6.47 mL, 45.84 mmol) in MeOH (30 mL). Purification by silica gel chromatography (2:3 hexanes/EtOAc) yielded 4.86 g (94%) of 1a as a white solid (Lokhov, S. G.; Podyminogin, M. A.; Sergeev, D. S.; Silnikov, V. N.; Kutyavin, I. V.; Shishkin, G. V.; Zarytova, V. P. *Bioconjugate Chem.* 1992, 3, 414-419.)

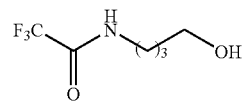

1b

4-Trifluoroacetamido-1-butanol (1b): Following general procedure I, butanolamine (2.0 g, 22.44 mmol) was combined with triethylamine (7.82 mL, 56.09 mmol) and trifluoroacetic anhydride (4.44 mL, 24.10 mmol) in MeOH (20 mL). Purification by silica gel chromatography (2:3 hexanes/EtOAc) yielded 4.03 g (97%) of 1b as a pale yellow oil (Lokhov, S. G.; Podyminogin, M. A.; Sergeev, D. S.; Silnikov, V. N.; Kutyavin, I. V.; Shishkin, G. V.; Zarytova, V. P. *Bioconjugate Chem.* 1992, 3, 414-419.)

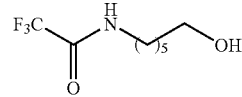

1c

6-Trifluoroacetamido-1-hexanol (1c): Following general procedure I, hexanolamine (2.0 g, 17.06 mmol) was combined with triethylamine (5.95 mL, 42.67 mmol) and trifluoroacetic anhydride (3.37 mL, 23.89 mmol) in MeOH (15 mL). Purification by silica gel chromatography (2:3 hexanes/EtOAc) yielded 3.35 g (92%) of 1c as a white solid (Vincent, S. P.; Gastinel, L. N. Carbohydr. Res. 2002, 337, 1039-1042.)

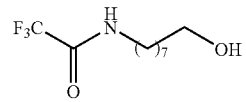

1d

8-Trifluoroacetamido-1-octanol (1d): Following general procedure I, octanolamine (2.5 g, 17.21 mmol) was combined with triethylamine (6.0 mL, 43.04 mmol) and trifluoroacetic anhydride (3.4 mL, 24.10 mmol) in MeOH (15 mL). Purification by silica gel chromatography (2:3 hexanes/EtOAc)

yielded 4.09 g (98%) of 1d as a white solid. $^1$H (300 MHz, CD$_3$OD): δ 3.61 (t, 2H, J=6.6 Hz), 3.34 (t, 2H, J=7.2), 1.63 (m, 4H), 1.42 (m, 8H); $^{13}$C (75 mHz, CD$_3$OD): δ 158.61 (q, J=81.5 Hz), 117.58 (q, J=284.6 Hz), 63.02, 40.79, 33.88, 30.51, 30.48, 30.30, 29.85, 27.79, 28.88; ESI-MS calcd for C$_{10}$H$_{18}$F$_3$NO$_2$ [M+Na]$^+$: 264.1197. found 264.1186.

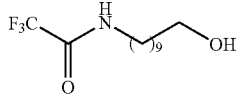

1e

10-Trifluoroacetamido-1-decanol (1e): Following general procedure I, decanolamine (0.50 g, 2.89 mmol) was combined with triethylamine (1.0 mL, 7.21 mmol) and trifluoroacetic anhydride (0.57 mL, 4.04 mmol) in MeOH (3 mL). Purification by silica gel chromatography (2:3 hexanes/EtOAc) yielded 0.722 g (99%) of 1e as a white solid. $^1$H (300 MHz, CD$_3$OD): δ 3.55 (t, 2H, J=5.4 Hz), 3.28 (t, 2H, J=7.2 Hz), 1.55 (m, 4H), 1.35 (m, 10H). $^{13}$C (75 mHz, CD$_3$OD): δ 82.99, 40.74, 33.83, 30.62, 30.54, 30.25, 29.78, 27.77, 26.92; ESI-MS calcd for C$_{12}$H$_{22}$F$_3$NO$_2$ [M+Na]$^+$: 292.1500. found 292.1507.

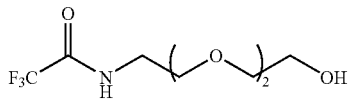

1f

8-Trifluoroacetamido-3,6-dioxa-1-octanol (1f: 8-azido-3,6-dioxa-1-octanol (Amvamzollo, P. H.; Sinay, P. *Carbohydr. Res.* 1986, 150, 199-212) (0.7 g, 4.0 mmol) was synthesized from triethylene glycol following the reported procedure (Bertozzi, C. R.; Bednarski, M. D. *J. Org. Chem.* 1991, 56, 4326-4329). The azide was combined with Pd/C (150 mg) in MeOH (8.0 mL) and stirred 12 h under H$_2$ (1 atm). The suspension was filtered over celite, and the filtrate was concentrated to afford the amine (0.590 g, 4.0 mmol) in quantitative yields (Sato, H.; Hayashi, E.; Yamada, N.; Yatagai, M.; Takahara, Y. *Bioconjugate Chem.* 2001, 12, 701-710.). Following general procedure 1, 2-[2-(2-aminoethoxy)ethoxy]ethanol (0.590 g, 3.95 mmol) was combined with triethylamine (1.378 mL, 9.89 mmol) and trifluoroacetic anhydride (0.782 mL, 5.54 mmol) in MeOH (5 mL). Purification by silica gel chromatography (EtOAc) yielded 0.576 g (60%) of if as a white solid. $^1$H (300 MHz, CD$_3$OD): δ 7.87 (br s, 1H), 3.73 (m, 2H), 3.68-3.60 (m, 10H), 3.55 (t, 2H, J=4.5 Hz), 3.32 (br s, 1H); $^{13}$C (75 mHz, CD$_3$OD): δ 157.6 (q, J=36.6 Hz), 116.1 (q, J=286.1 Hz), 72.68, 70.35, 70.24, 68.90, 61.52, 39.84; ESI-MS calcd for C$_8$H$_{14}$F$_3$NO$_4$ [M–H]$^-$: 244.0797. found 244.0795.

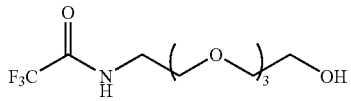

1g

11-Trifluoroacetamido-3,6,9-trioxa-1-undecanol (1g): 11-azido-3,6,9-trioxa-1-undecane (0.6 g, 2.7 mmol) was synthesized from tetraethylene glycol following the reported procedure (Bertozzi, C. R.; Bednarski, M. D. *J. Org. Chem.* 1991, 56, 4326-4329.). The azide was combined with Pd/C (150 mg) in MeOH (7.0 mL) and stirred 12 h under H$_2$ (1 atm). The suspension was filtered over celite and the filtrate was concentrated to afford the amine (0.520 g, 2.7 mmol) in quantitative yields (Xie, H. Z.; Braha, O.; Gu, L. Q.; Cheley, S.; Bayley, H. *Chem. Biol.* 2005, 12, 109-120.) Following general procedure 1, 2-[2-(2-[2-aminoethoxy]ethoxy) ethoxy]ethanol (0.50 g, 2.59 mmol) was combined with triethylamine (0.902 mL, 6.48 mmol) and trifluoroacetic anhydride (0.51 mL, 3.62 mmol) in MeOH (3 mL). Purification by silica gel chromatography (EtOAc) yielded 0.343 g (46%) of 1g as a white solid. $^1$H (300 MHz, CD$_3$OD): δ 3.69 (t, 2H, J=3.9 Hz), 3.64 (m, 12H), 3.57 (t, 2H, J=3.5 Hz). $^{13}$C (75 mHz, CD$_3$OD): δ 157.7 (q, J=37.1 Hz), 118.1 (q, J=285.8 Hz), 72.56. 70.78, 70.46, 70.15, 69.82, 69.56, 61.34, 39.95; ESI-MS calcd for C$_{10}$H$_{18}$F$_3$NO$_5$ [M–H]$^-$: 288.1059. found 288.1060.

General Procedure II:

Coupling of Dibenzyl Phosphate and Alcohol 1.

Dibenzyl phosphate (1.5 eq) was dissolved in DMF and CH$_2$Cl$_2$, and the resulting solution was cooled to 0° C. Oxalyl chloride (3.0 eq) was added dropwise under an argon atmosphere. The solution was allowed to warm to room-temperature, and was stirred for 1 h. The solvent was removed in vacuo and the remaining material was azeotroped with toluene. The resulting viscous liquid was dissolved in CH$_2$Cl$_2$ and added dropwise to a flask containing 1 and 4 Å molecular sieves (ca. 5-10) in pyridine at 0° C. The solution was stirred under an argon atmosphere for 1 h at 0° C. and then for 3 h at room-temperature. The solvent was removed in vacuo and the product was purified by silica gel chromatography (1:1→1:2 Hexane/EtOAc) to afford 2.

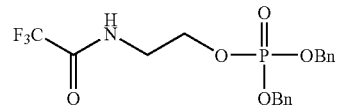

2a

1-O-(Dibenzyl phosphoryloxy)-2-trifluoroacetamido-1-ethanol (2a): Following general procedure II, dibenzyl phosphate (1.79 g, 6.45 mmol) was dissolved in DMF (10 μL) and CH$_2$Cl$_2$ (25 mL) and combined with oxalyl chloride (1.13 mL, 12.9 mmol). After concentration, the compound was redissolved in CH$_2$Cl$_2$ (5 mL) and added to 1a (675 mg, 4.3 mmol) in pyridine (10 mL) and 4 Å molecular sieves to yield 621 mg (35%) of 2a as an off-white solid. $^1$H (300 MHz, CDCl$_3$): δ 7.35 (m, 10H), 5.03 (ABX system, 4H, J$_{AB}$=15 Hz, J$_{AP}$=J$_{BP}$=11.7 Hz), 4.04 (pentet, 2H, J=4.8 Hz), 3.50 (q, 2H, J=5.1). $^{13}$C (75 mHz, CDCl$_3$): δ 135.45, 129.00, 128.12, 70.02, 65.7, 40.49. ESI-MS calcd for C$_{18}$H$_{19}$F$_3$NO$_5$P [M+H]$^+$: 418.1031. found 418.1019.

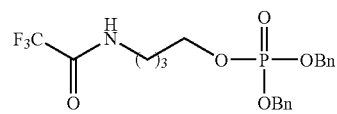

2b

1-O-(Dibenzyl phosphoryloxy)-4-trifluoroacetamido-1-butanol (2b): Following general procedure II, dibenzyl phosphate (1.79 g, 6.45 mmol) was dissolved in DMF (10 μL) and CH$_2$Cl$_2$ (30 mL) and combined with oxalyl chloride (1.13 mL, 12.9 mmol). After concentration, the compound was redissolved in CH₂Cl₂ (5 mL) and added to 1b (796 mg, 4.3 mmol) in pyridine (10 mL) and 4 Å molecular sieves to yield 777 mg (41%) of 2b as a clear oil. $^1$H (300 MHz, CDCl₃): δ 7.35 (m, 10H), 5.01 (ABX system, 4H, $J_{AB}$=15 Hz, $J_{AP}$=$J_{BP}$=11.7 Hz), 3.97 (q, 2H, J=6 Hz), 3.28 (q, 2H, J=6), 1.70 (m, 4H). $^{13}$C (75 mHz, CDCl₃): δ 135.90, 128.84, 128.16, 116.54 (q, J=284.6 Hz), 69.60, 67.42, 39.97, 27.49, 25.08; ESI-MS calcd for C₂₀H₂₃F₃NO₅P [M+Na]⁺: 468.1164. found 468.1160.

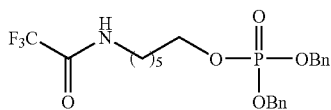

2c

1-O-(Dibenzyl phosphoryloxy)-6-trifluoroacetamido-1-hexanol (2c): Following general procedure II, dibenzyl phosphate (1.79 g, 6.45 mmol) was dissolved in DMF (10 μL) and CH₂Cl₂ (25 mL) and combined with oxalyl chloride (1.13 mL, 12.9 mmol). After concentration, the compound was redissolved in CH₂Cl₂ (5 mL) and added to 1c (917 mg, 4.3 mmol) in pyridine (10 mL) and 4 Å molecular sieves to yield 884 mg (43%) of 2c as a clear oil (16).

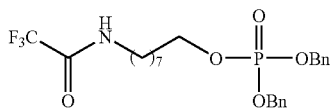

2d

1-O-(Dibenzyl phosphoryloxy)-8-trifluoroacetamido-1-octanol (2d): Following general procedure II, dibenzyl phosphate (1.73 g, 6.22 mmol) was dissolved in DMF (10 μL) and CH₂Cl₂ (25 mL) and combined with oxalyl chloride (1.08 mL, 12.4 mmol). After concentration, the compound was redissolved in CH₂Cl₂ (5 mL) and added to 1d (1.00 g, 4.15 mmol) in pyridine (10 mL) and 4 Å molecular sieves to yield 966 mg (46%) of 2d as a clear oil. $^1$H (300 MHz, CDCl₃): δ 7.31 (m, 10H), 5.00 (ABX system, 4H, $J_{AB}$=15 Hz, $J_{AP}$=$J_{BP}$=11.7 Hz), 3.96 (q, 2H, J=6.6 Hz), 3.31 (q, 2H, J=6.6 Hz), 1.55 (m, 4H), 1.27 (m, 8H). $^{13}$C (75 mHz, CDCl₃): δ 135.92, 128.63, 127.96, 69.33, 67.98, 39.99, 30.09, 28.91, 26.58, 25.29; ESI-MS calcd for C₂₄H₃₁F₃NO₅P [M+Na]⁺: 524.1790. found 524.1802.

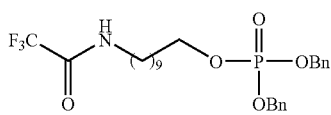

2e

1-O-(Dibenzyl phosphoryloxy)-10-trifluoroacetamido-1-decanol (2e): Following general procedure II, dibenzyl phosphate (775 mg, 2.78 mmol) was dissolved in DMF (10 μL) and CH₂Cl₂ (15 mL) and combined with oxalyl chloride (0.50 mL, 5.57 mmol). After concentration, the compound was redissolved in CH₂Cl₂ (5 mL) and added to 1e (500 mg, 1.86 mmol) in pyridine (5 mL) and 4 Å molecular sieves to yield 578 mg (59%) of 2e as a clear oil. $^1$H (300 MHz, CDCl₃): δ 7.34 (m, 10H), 5.01 (ABX system, 4H, $J_{AB}$=15 Hz, $J_{AP}$=$J_{BP}$=11.7 Hz), 3.97 (q, 2H, J=6 Hz), 3.33 (q, 2H, J=6.6), 1.70 (m, 4H), 1.25 (m, 12H). $^{13}$C (75 mHz, CDCl₃): δ 135.99, 128.62, 127.98, 69.33, 66.18, 40.09, 30.25, 29.44, 29.30, 29.19, 29.02, 28.97, 26.10, 25.37; ESI-MS calcd for C₂₆H₃₅F₃NO₅P [M+Na]⁺: 552.2103. found 552.2094.

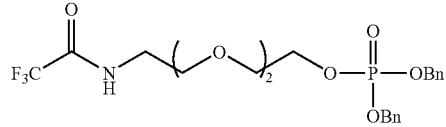

2f

1-O-(Dibenzyl phosphoryloxy)-8-trifluoroacetamido-3,6-dioxa-1-octanol (2f): Following general procedure II, dibenzyl phosphate (981 mg, 3.53 mmol) was dissolved in DMF (20 μL) and CH₂Cl₂ (15 mL) and combined with oxalyl chloride (0.62 mL, 7.05 mmol). After concentration, the compound was redissolved in CH₂Cl₂ (5 mL) and added to 1f (500 mg, 2.35 mmol) in pyridine (5 mL) and 4 Å molecular sieves to yield 623 mg (53%) of 2f as a clear oil. $^1$H (300 MHz, CDCl₃): δ 7.34 (m, 10H), 5.04 (ABX system, 4H, $J_{AB}$=15 Hz, $J_{AP}$=$J_{BP}$=11.7 Hz), 4.12-4.09 (m, 2H), 3.64 (t, 2H, J=5.1 Hz), 3.61-3.54 (m, 6H), 3.47 (q, 2H, J=4.8 Hz); $^{13}$C (75 mHz, CDCl₃): δ 157.5 (q, J=36.5 Hz), 135.9 (d, J=7.1 Hz), 135.8, 128.7, 128.0, 116.0 (q, J=286.4 Hz), 70.7, 70.4, 70.0 (d, J=6.5 Hz), 69.4 (d, J=5.1 Hz), 68.8, 66.9 (d, J=5.9 Hz), 39.94; ESI-MS calcd for C₂₂H₂₇F₃NO₇P [M−H]⁻: 504.1399. found 504.1420.

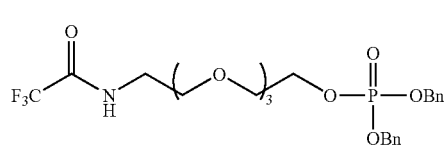

2g

1-O-(Dibenzyl phosphoryloxy)-11-trifluoroacetamido-3,6,9-trioxa-1-undecanol (2g): Following general procedure II, dibenzyl phosphate (433 mg, 1.56 mmol) was dissolved in DMF (10 μL) and CH₂Cl₂ (10 mL) and combined with oxalyl chloride (0.27 mL, 3.11 mmol). After concentration, the compound was redissolved in CH₂Cl₂ (5 mL) and added to 1g (300 mg, 1.04 mmol) in pyridine (5 mL) and 4 Å molecular sieves to yield 499 mg (87%) of 2g as a clear oil. $^1$H (300 MHz, CDCl₃): δ7.34 (m, 10H), 5.04 (ABX system, 4H, $J_{AB}$=15 Hz, $J_{AP}$=$J_{BP}$=11.7 Hz), 4.14 (m, 2H), 3.64 (t, 2H, J=5.0 Hz), 3.62-3.55 (m, 10H), 3.50 (q, 2H, J=5.1 Hz). $^{13}$C (75 mHz, CDCl₃): δ 157.5 (q, J=37.2 Hz), 136.0 (d, J=6.1 Hz), 128.7, 128.1, 116.1 (q, J=286.3 Hz), 70.8, 70.7, 70.6, 70.4, 70.1 (d, J=6.8 Hz), 68.8, 66.9 (d, J=5.9 Hz), 39.9; ESI-MS calcd for C₂₄H₃₁F₃NO₈P [M+Na]⁺: 572.1637. found 572.1654.

General Procedure III: Hydrogenolysis of Phosphotriester 2.

Phosphotriester 2 (1 eq) was dissolved in 3:2 MeOH/EtOAc with triethylamine (1 eq). Pd/C was added and the suspension was stirred under H₂ (1 atm) for 12 h. The suspension was filtered through celite and the filtrate was concentrated to yield phosphate 3 as the triethylammonium salt.

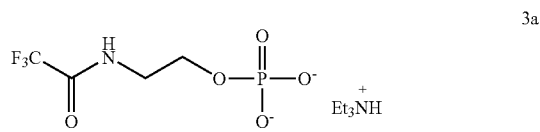

3a

2-Trifluoroacetamido-ethanol-1-phosphate triethylammonium salt (3a): Following general procedure III, phosphotriester 2a (367 mg, 0.88 mmol) was dissolved in 3:2 MeOH/EtOAc (15 mL) and triethylamine (0.12 mL), and combined with Pd/C (184 mg) and $H_2$ to yield the triethylammonium salt of 3a (290 mg, 97%) as a white solid. $^1H$ (300 MHz, $CD_3OD$): δ 3.98 (q, 2H, J=6.9), 3.52 (t, 2H, J=5.4 Hz), 3.18 (q, 6H, J=7.2 Hz), 1.31 (t, 9H, J=7.5 Hz); $^{13}C$ (75 mHz, $CD_3OD$): δ 63.78, 47.52, 41.93, 9.10; ESI-MS calcd for $C_4H_7F_3NO_5P$ [M−H]⁻: 235.9936. found 235.9947.

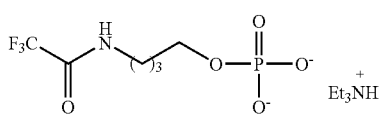

4-Trifluoroacetamido-butanol-1-phosphate triethylammonium salt (3b): Following general procedure III, phosphotriester 2b (392 mg, 0.88 mmol) was dissolved in 3:2 MeOH/EtOAc (15 mL) and triethylamine (0.12 mL), and combined with Pd/C (196 mg) and $H_2$ to yield the triethylammonium salt of 3b (339 mg, 97%) as a white solid. $^1H$ (300 MHz, $CD_3OD$): δ 3.85 (q, 2H, J=6.3), 3.25-3.20 (m, 2H), 3.14 (q, 6H, J=7.5 Hz), 1.74-1.54 (m, 4H), 1.27 (t, 9H, J=7.2 Hz); $^{13}C$ (75 mHz, $CD_3OD$): δ 64.35, 46.31, 39.26, 27.76, 25.24, 7.89; ESI-MS calcd for $C_6H_{11}F_3NO_5P$ [M−H]⁻: 264.0249. found 264.0240.

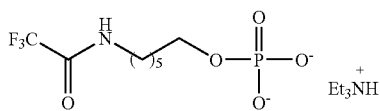

6-Trifluoroacetamido-hexanol-1-phosphate triethylammonium salt (3c): Following general procedure III, phosphotriester 2c (441 mg, 0.93 mmol) was dissolved in 3:2 MeOH/EtOAc (15 mL) and triethylamine (0.13 mL), and combined with Pd/C (220 mg) and $H_2$ to yield the triethylammonium salt of 3c (351 mg, 96%) as a clear oil (Vincent, S. P.; Gastinel, L. N. Carbohydr. Res. 2002, 337, 1039-1042.)

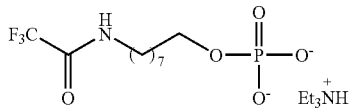

8-Trifluoroacetamido-octanol-1-phosphate triethylammonium salt (3d): Following general procedure III phosphotriester 2d (400 mg, 0.80 mmol) was dissolved in 3:2 MeOH/EtOAc (12 mL) and triethylamine (0.11 mL), and combined with Pd/C (200 mg) and $H_2$ to yield the triethylammonium salt of 3d (320 mg, 95%) as a white solid. $^1H$ (300 MHz, $CD_3OD$): δ 3.92 (q, 2H, J=6.6), 3.26 (t, 2H, J=7.5), 3.20 (q, 6H, J=7.2 Hz), 1.70-1.50 (m, 4H), 1.40-1.29 (m, 17H); $^{13}C$ (75 mHz, $CD_3OD$): δ 67.23, 47.74, 40.70, 30.17, 29.79, 27.71, 26.64, 18.78, 17.30, 9.18; ESI-MS calcd for $C_{10}H_{19}F_3NO_5P$ [M−H]⁻: 320.0875. found 320.0883.

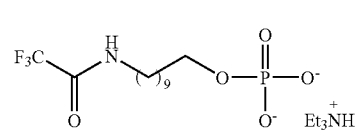

10-Trifluoroacetamido-decanol-1-phosphate triethylammonium salt (3e): Following general procedure III, phosphotriester 2e (554 mg, 1.02 mmol) was dissolved in 3:2 MeOH/EtOAc (15 mL) and triethylamine (0.15 mL), and combined with Pd/C (270 mg) and $H_2$ to yield the triethylammonium salt of 3e (460 mg, 98%) as a white solid. $^1H$ (300 MHz, $CD_3OD$): δ 3.77 (q, 2H, J=6.6), 3.19 (t, 2H, J=7.2 Hz), 3.09 (q, 6H, J=7.2 Hz), 1.59-1.43 (m, 4H), 1.33-1.20 (m, 21H); $^{13}C$ (75 mHz, $CD_3OD$): δ 66.22, 47.48, 40.74, 30.63, 30.53, 30.50, 30.45, 30.29, 29.80, 27.79, 26.94, 9.09; ESI-MS calcd for $C_{12}H_{22}F_3NO_5P$ [M−H]⁻: 348.1188. found 348.1198.

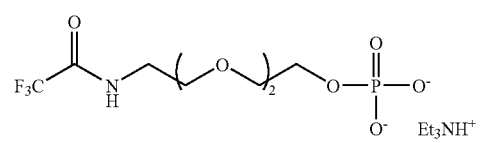

8-trifluoroacetamido-3,6-dioxa-octanol-1-phosphate triethylammonium salt (3f: Following general procedure III, phosphotriester 2f (550 mg, 1.09 mmol) was dissolved in MeOH (10 mL) and triethylamine (0.15 mL), and combined with Pd/C (275 mg) and $H_2$ to yield the triethylammonium salt of 3f (462 mg, 99%) as a white solid. $^1H$ (300 MHz, $CD_3OD$): δ 3.81 (td, 2H, J=6.1, 4.4 Hz), 3.50-3.40 (m, 8H), 3.29 (t, 2H, J=5.3 Hz), 3.00 (q, 6H, J=7.0 Hz), 1.35 (t, 9H, J=7.1 Hz); $^{13}C$ (75 mHz, $CD_3OD$): δ159.2 (q, J=36.2 Hz), 117.7 (q, J=285.1 Hz), 72.2 (d, J=7.2 Hz), 71.7, 71.5, 69.9, 65.6 (d, J=5.6 Hz), 47.5, 40.9, 9.3; ESI-MS calcd for $C_8H_{15}F_3NO_7P$ [M−H]⁻: 324.0460. found 324.0471.

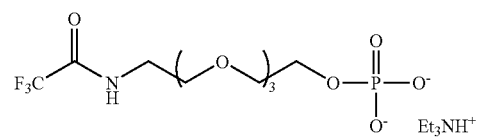

11-trifluoroacetamido-3,6,9-trioxa-undecanol-1-phosphate triethylammonium salt (3g): Following general procedure III, phosphotriester 2g (450 mg, 0.82 mmol) was dissolved in MeOH (9 mL) and triethylamine (0.12 mL), and combined with Pd/C (225 mg) and $H_2$ to yield the triethylammonium salt of 3g (397 mg, 99%) as a pasty, white solid. $^1H$ (300 MHz, $CD_3OD$): δ 3.92-2.90 (m, 2H), 3.60-3.47 (m, 12H), 3.37 (t, 2H, J=5.1 Hz), 3.08 (q, 6H, J=7.1 Hz), 1.21 (t, 9H, J=6.8 Hz); $^{13}C$ (75 mHz, $CD_3OD$): δ 117.7 (q, J=284.9 Hz), 72.0, 71.7, 71.6, 71.5, 69.9, 66.0, 47.8, 40.9, 9.3; ESI-MS calcd for $C_{10}H_{19}F_3NO_8P$ [M−H]⁻: 368.0722. found 368.0721.

General Procedure IV: Coupling of phosphate 3 to uridine 5'-monophosphate (UMP) and trifluoracetamide removal.

5'-UMP (triethylammonium salt, 1.0 eq) was suspended in acetonitrile (3 mL) and cooled to 0° C. Dimethylaniline (4 eq) and triethylamine (2 eq) were added under an argon atmosphere. A pre-cooled solution of trifluoroacetic anhydride (6 eq) in acetonitrile (1 mL) was added dropwise over several minutes to yield a transparent, pink solution. The reaction was stirred at 0° C. for 15 min and the solvent was removed in vacuo. The residue was resuspended in acetonitrile (3 mL) and stirred at 0° C. with 4 Å molecular sieves (ca. 5-10) under an argon atmosphere. Triethylamine (5 eq) and 1-methyl imidazole (5.3 eq) were added dropwise and the solution turned bright yellow. Phosphate 3 (0.63 eq) was dissolved in acetonitrile (1 mL) and added dropwise to the solution. The reaction was stirred at 0° C. for 1 h, and room-temperature for 3 h. The reaction was quenched with 15 mL H$_2$O and extracted with CH$_2$Cl$_2$ (15 mL). The organic layer was extracted with H$_2$O (15 mL) and the combined aqueous layers were combined and concentrated, and the product was purified by silica gel chromatography. The resulting product was treated with 3 M ammonium hydroxide to deprotect the trifluoroacetamide moiety. The solvent was evaporated in vacuo and the product was lyophilized to yield diphosphate 4 as the ammonium salt.

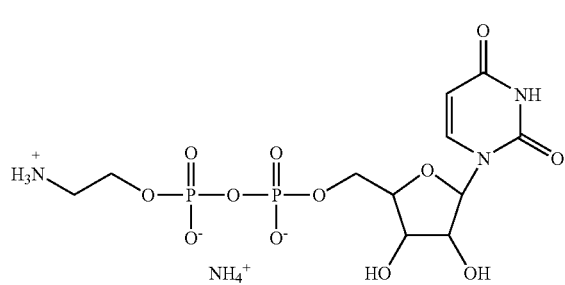

4a

Uridine 5'-diphosphoethanolamine, ammonium salt (4a): Following general procedure IV, UMP.Et$_3$NH$^+$ (102 mg, 0.238 mmol) was activated with dimethyl aniline (120 µL, 0.952 mmol), triethylamine (50 µL, 0.476 mmol) and trifluoroacetic anhydride (200 µL, 1.428 mmol). The activated UMP was then reacted with 1-methylimidazole (100 mL, 1.26 mmol), triethylamine (130 µL, 1.19 mmol) and phosphate 3a (50 mg, 0.15 mmol). The product was purified by silica gel chromatography (5:4:1 CHCl$_3$/MeOH/1 M ammonium acetate) to yield the ammonium salt of the diphosphate as an off white solid. The diphosphate was stirred with 3 M ammonium hydroxide (10 mL) for 2 h under N$_2$, the solvent was removed in vacuo and the product was lyophilized to yield the ammonium salt of uridine 5'-diphosphoethanolamine 4a (33 mg, 45%) as an off-white solid. $^1$H (300 MHz, D$_2$O): δ 7.98 (d, 1H, J=8.1 Hz), 6.03 (d, 1H, J=4.6 Hz), 6.01 (d, 1H, J=8.5 Hz), 4.42 (m, 2H), 4.33 (br s, 1H), 4.30-4.22 (m, 5H), 3.35 (t, 2H, J=6.9 Hz), 1.92 (s, 4H); $^{13}$C (75 mHz, D$_2$O): δ152.1, 141.7, 102.8, 88.8, 83.3 (d, J=8.0 Hz), 73.9, 69.8, 65.1 (d, J=7.7 Hz), 62.5, 36.8, 23.5; ESI-MS calcd for C$_{11}$H$_{19}$N$_3$O$_{12}$P$_2$ [M−H]$^-$: 446.0366. found 446.0348.

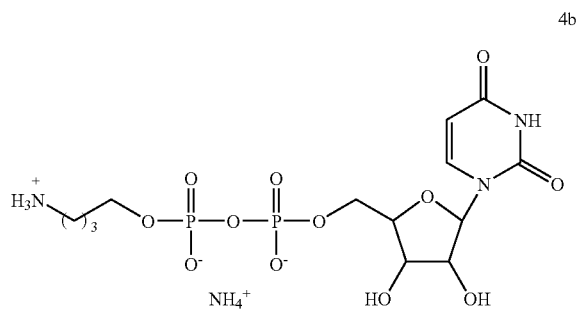

4b

Uridine 5'-diphosphobutanolamine, ammonium salt (4b): Following general procedure IV, UMP.Et$_3$NH$^+$ (102 mg, 0.238 mmol) was activated with dimethyl aniline (120 µL, 0.952 mmol), triethylamine (50 µL, 0.476 mmol) and trifluoroacetic anhydride (200 µL, 1.428 mmol). The activated UMP was then reacted with 1-methylimidazole (100 mL, 1.26 mmol), triethylamine (130 µL, 1.19 mmol) and phosphate 3b (55 mg, 0.15 mmol). The product was purified by silica gel chromatography (5:4:1 CHCl$_3$/MeOH/1 M ammonium acetate) to yield the ammonium salt of the diphosphate as an off white solid. The diphosphate was stirred with 3 M ammonium hydroxide (10 mL) for 2 h under N$_2$, the solvent was removed in vacuo and the product was lyophilized to yield the ammonium salt of uridine 5'-diphosphobutanolamine 4b (46 mg, 58%) as an off-white solid. $^1$H (300 MHz, D$_2$O): δ 7.96 (d, 1H, J=8.1 Hz), 6.01 (d, 1H, J=4.7 Hz), 6.00 (d, 1H, J=8.4 Hz), 4.39 (br s, 2H), 4.31 (br s, 1H), 4.31-4.22 (m, 2H), 4.04-4.00 (m, 2H), 3.68 (br s, 2H), 1.96 (s, 4H), 1.78 (m, 4H); $^{13}$C (75 mHz, D$_2$O): δ 165.1, 150.6, 140.1, 101.2, 87.1, 81.7, 72.2, 68.2, 63.5, 62.1, 37.8, 25.2 (d, J=6.6 Hz), 22.2; ESI-MS calcd for C$_{13}$H$_{23}$N$_3$O$_{12}$P$_2$ [M+Na]$^+$: 498.0655. found 498.0648.

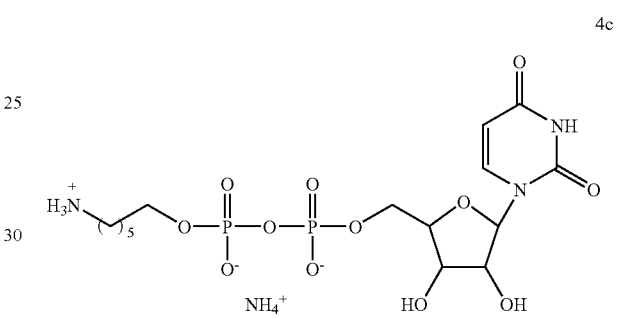

4c

Uridine 5'-diphosphohexanolamine, ammonium salt (4c): Following general procedure IV, UMP.Et$_3$NH$^+$ (102 mg, 0.238 mmol) was activated with dimethyl aniline (120 µL, 0.952 mmol), triethylamine (50 µL, 0.476 mmol) and trifluoroacetic anhydride (200 µL, 1.428 mmol). The activated UMP was then reacted with 1-methylimidazole (100 mL, 1.26 mmol), triethylamine (130 µL, 1.19 mmol) and phosphate 3c (6 mg, 0.15 mmol). The product was purified by silica gel chromatography (5:4:1 CHCl$_3$/MeOH/H$_2$O) to yield the triethylammonium salt of the diphosphate as an off-white solid. The diphosphate was stirred with 3 M ammonium hydroxide (10 mL) for 2 h under N$_2$, the solvent was removed in vacuo and the product was lyophilized to yield the ammonium salt of uridine 5'-diphosphohexanolamine 4c (56 mg, 71%) as an off-white solid (Barker, R.; Shaper, J. H.; Hill, R. L.; Olsen, K. W. *J. Biol. Chem.* 1972, 247, 7135.)

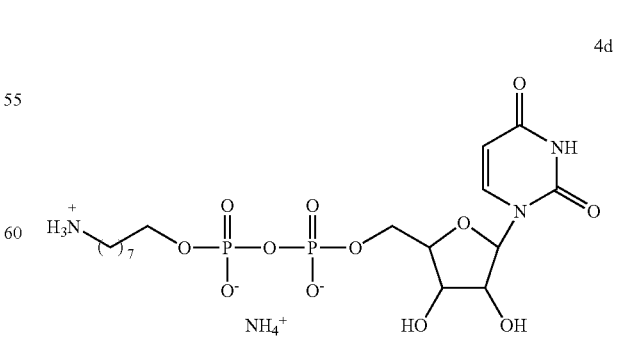

4d

Uridine 5'-diphosphooctanolamine, ammonium salt (4d): Following general procedure IV, UMP.Et$_3$NH$^+$ (102 mg, 0.238 mmol) was activated with dimethyl aniline (120 μL, 0.952 mmol), triethylamine (50 μL, 0.476 mmol) and trifluoroacetic anhydride (200 μL, 1.428 mmol). The activated UMP was then reacted with 1-methylimidazole (100 mL, 1.26 mmol), triethylamine (130 μL, 1.19 mmol) and phosphate 3d (65 mg, 0.15 mmol). The product was purified by silica gel chromatography (5:4:1 CHCl$_3$/MeOH/H$_2$O) to yield the triethylammonium salt of the diphosphate as an off-white solid. The diphosphate was stirred with 3 M ammonium hydroxide (10 mL) for 2 h under N$_2$, the solvent was removed in vacuo and the product was lyophilized to yield the ammonium salt of uridine 5'-diphosphooctanolamine 4d (78 mg, 89%) as an off-white solid. $^1$H (300 MHz, D$_2$O): δ 8.67 (s, 1H), 7.98 (d, 1H, J=7.9 Hz), 7.44 (s, 1H), 6.0-5.97 (m, 2H), 4.37-4.29 (m, 2H), 4.37 (d, 1H, J=3.9 Hz), 4.29-4.18 (m, 3H), 3.98-3.92 (m, 2H), 2.99 (t, 2H, J=8.4 Hz), 2.75 (s, 4H), 1.68-1.61 (m, 4H), 1.38-1.30 (m, 8H); $^{13}$C (75 mHz, D$_2$O): δ 168.8, 154.4, 144.3, 137.5, 125.5, 122.0, 105.3, 91.0, 85.8 (d, J=5.4 Hz), 76.4, 72.1, 69.6 (d, J=3 Hz), 67.5, 42.1, 41.3, 38.0, 32.2 (d, J=4.0 Hz), 30.5, 29.2, 27.9, 27.2; ESI-MS calcd for C$_{17}$H$_{31}$N$_3$O$_{12}$P$_2$ [M+Na]$^+$: 554.1281. found 554.1257.

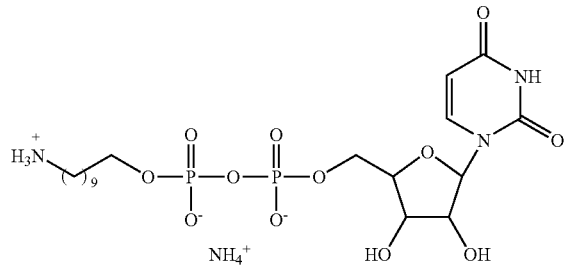

4e

Uridine 5'-diphosphodecanolamine, ammonium salt (4e): Following general procedure IV, UMP.Et$_3$NH$^+$ (102 mg, 0.238 mmol) was activated with dimethyl aniline (120 μL, 0.952 mmol), triethylamine (50 μL, 0.476 mmol) and trifluoroacetic anhydride (200 μL, 1.428 mmol). The activated UMP was then reacted with 1-methylimidazole (100 mL, 1.26 mmol), triethylamine (130 μL, 1.19 mmol) and phosphate 3e (70 mg, 0.15 mmol). The product was purified by silica gel chromatography (CHCl$_3$/MeOH/H$_2$O 12/6/1) to yield the triethylammonium salt of the diphosphate as an off-white solid. The diphosphate was stirred with 3 M ammonium hydroxide (10 mL) for 2 h under N$_2$, the solvent was removed in vacuo and the product was lyophilized to yield the ammonium salt of uridine 5'-diphosphodecanolamine 4e (66 mg, 76%) as an off-white solid. $^1$H (300 MHz, D$_2$O): δ 8.77 (br s, 1H, 8.11, (d, 1H, J=8.0 Hz), 7.57 (br s, 2H), 6.09-6.04 (m, 2H), 4.47-4.42 (m, 2H), 4.34 (br s, 3H), 4.04 (s, 4H), 4.02 (m, 2H), 3.11 (t, 2H, J=7.6 Hz), 1.78 (t, 2H, J=6.2 Hz), 1.69 (t, 2H, J=6.7 Hz); $^{13}$C (75 mHz, 10:1 D$_2$O/d$_6$-acetone): δ 165.9, 151.8, 142.1, 102.9, 88.8, 83.6 (d, J=8.5 Hz), 74.3, 70.1, 66.9 (d, J=5.3 Hz), 65.3, 39.9, 35.7, 29.2, 29.1, 28.8, 27.2, 26.2, 25.6; ESI-MS calcd for C$_{19}$H$_{35}$N$_3$O$_{12}$P$_2$ [M+H]$^+$: 560.1774. found 560.1777.

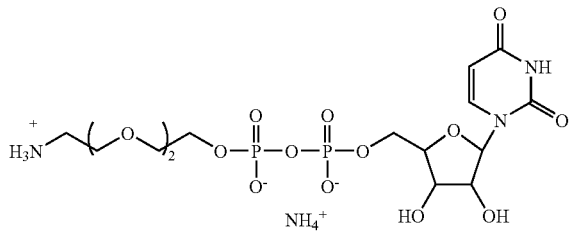

4f

Uridine 5'-diphospho-3,6-dioxa-octanolamine, ammonium salt (40: Following general procedure IV, UMP.Et$_3$NH$^+$ (150 mg, 0.35 mmol) was activated with dimethyl aniline (177 μL, 1.40 mmol), triethylamine (98 μL, 0.70 mmol) and trifluoroacetic anhydride (297 μL, 2.10 mmol). The activated UMP was then reacted with 1-methylimidazole (171 mL, 1.86 mmol), triethylamine (244 μL, 1.75 mmol) and phosphate 3f (94 mg, 0.22 mmol). The product was purified by silica gel chromatography (CHCl$_3$/MeOH/H$_2$O 12/6/1) to yield the triethylammonium salt of the diphosphate as an off-white solid. The diphosphate was stirred with 3 M ammonium hydroxide (10 mL) for 2 h under N$_2$, the solvent was removed in vacuo and the product was lyophilized to yield the ammonium salt of uridine 5'-diphospho-3,6-dioxa-octanolamine 4f (98 mg, 78%) as an off-white solid. $^1$H (300 MHz, D$_2$O): δ 7.96 (d, 1H, J=8.2 Hz), 6.01 (d, 1H, J=4.2 Hz), 5.99 (d, 1H, J=7.8 Hz), 4.39 (m, 2H), 4.30 (m, 1H), 4.15-4.09 (m, 2H), 3.80 (t, 2H, J=6.0 Hz), 3.56 (br s, 8H), 3.25 (t, 2H, J=5.1 Hz); $^{13}$C (75 mHz, D$_2$O): δ 166.3, 151.9, 141.8, 102.8, 88.7, 83.3 (d, J=8.2 Hz), 73.9, 70.2, 70.2, 69.8, 69.6, 66.6, 65.3, 65.1 (d, J=7.7 Hz), 39.3; ESI-MS calcd for C$_{15}$H$_{28}$N$_3$O$_{14}$P$_2$ [M+H]$^+$: 536.1047. found 536.1060.

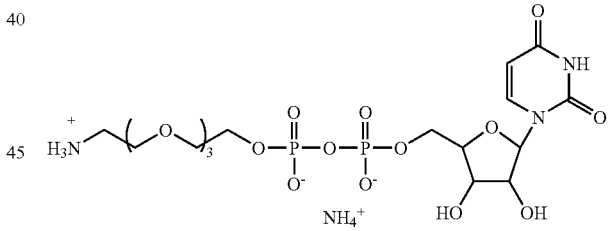

4g

Uridine 5'-diphospho-3,6,9-trioxa-undecanolamine, ammonium salt (4g): Following general procedure IV, UMP.Et$_3$NH$^+$ (147 mg, 0.344 mmol) was activated with dimethyl aniline (174 μL, 1.376 mmol), triethylamine (96 μL, 0.688 mmol) and trifluoroacetic anhydride (292 μL, 2.064 mmol). The activated UMP was then reacted with 1-methylimidazole (168 mL, 1.823 mmol), triethylamine (240 μL, 1.770 mmol) and phosphate 3g (102 mg, 0.220 mmol). The product was purified by silica gel chromatography (CHCl$_3$/MeOH/H$_2$O 12/6/1) to yield the triethylammonium salt of the diphosphate as an off-white solid. The diphosphate was stirred with 3 M ammonium hydroxide (10 mL) for 2 h under N$_2$, the solvent was removed in vacuo and the product was lyophilized to yield the ammonium salt of uridine 5'-diphospho-3,6,9-trioxa-undecanolamine 4g (95 mg, 70%) as an off-white solid. $^1$H (300 MHz, D$_2$O): δ 7.93 (d, 1H, J=8.1 Hz), 5.97 (d, 1H, J=4.2 Hz), 5.95 (d, 1H, J=8.1 Hz), 4.39-4.33 (m, 2H), 4.28 (br s, 1H), 4.10 (br s, 2H), 3.78 (t, 2H, J=5.4 Hz), 3.72 (br s, 12H), 3.23 (t, 2H, J=5.3 Hz); $^{13}$C (75 mHz, D$_2$O): δ 166.2, 151.8, 141.8, 102.7, 88.8, 73.8, 70.2, 69.7, 69.6, 69.5, 66.5, 65.3 (d, J=7.5 Hz), 39.3; ESI-MS calcd for C$_{17}$H$_{31}$N$_3$O$_{15}$P$_2$ [M–H]$^-$: 578.1152. found 578.1130.

General Procedure V: Conjugation of uridine 5′-diphospho (UDP)-alcoholamine 4 to fluorescein-5-isothiocyanate (FITC).
UDP-alcoholamine 4 (1.0 eq) was combined with FITC (1.5 eq) in 2:1 DMF/0.1 M NaHCO$_3$. The reaction mixture was stirred for 2 h and concentrated. The product was purified by silica gel chromatography (12:10:1 CHCl$_3$/MeOH/H$_2$O) to yield the sodium salt of UDP-fluorescein conjugate 5 as a yellow solid.

UDP-butanolamine-fluorescein conjugate (5b): Following general procedure V, UDP-butanolamine 4b (10 mg, 20 μmol) was combined with FITC (12 mg, 30 μmol) in 2:1 DMF/0.1 M NaHCO$_3$ (200 μL) to yield the sodium salt of UDP-ethanolamine-fluorescein conjugate 5b (11 mg, 62%) as a yellow solid. $^1$H (300 MHz, 5:1 D$_2$O:d$_7$-DMF): δ 7.96 (br s, 1H), 7.88 (d, 1H, J=8.6 Hz), 7.65 (m, 1H), 7.10 (m, 1H), 6.97 (d, 2H, J=9.2 Hz), 6.63 (d, 2H, J=1.8 Hz), 6.60 (d, 2H, J=9.8 Hz), 5.87-5.82 (m, 2H), 4.25 (br s, 2H), 4.13 (br s, 3H), 3.93 (br s, 2H), 3.52 (br s, 2H), 1.63 (br s, 4H); $^{13}$C (75 MHz, 5:1 D$_2$O:d$_7$-DMF): δ 182.8, 174.0, 168.0, 158.5, 154.0, 144.3,

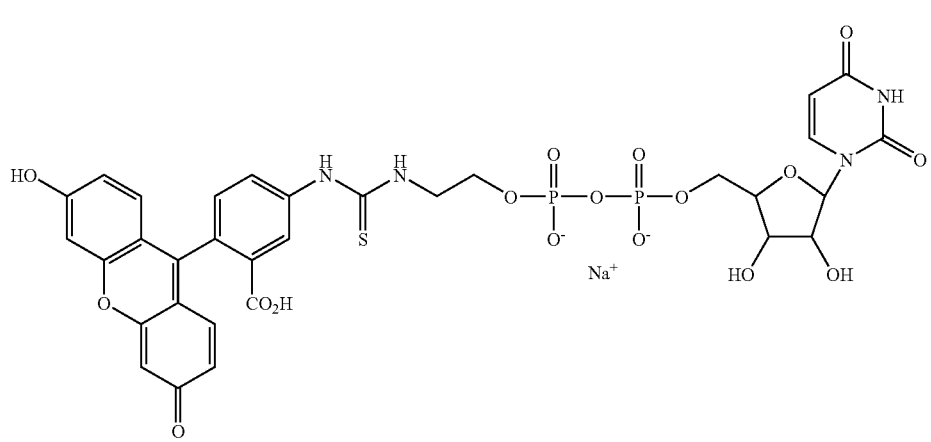

5a

UDP-ethanolamine-fluorescein conjugate (5a): Following general procedure V, UDP-ethanolamine 4a (5 mg, 9.6 μmol) was combined with FITC (5.6 mg, 14.4 μg) in 2:1 DMF/0.1M NaHCO$_3$ (150 μL) to yield the sodium salt of UDP-ethanolamine-fluorescein conjugate 5a (5.3 mg, 64%) as a yellow solid. $^1$H (300 MHz, 5:1 D$_2$O:d$_7$-DMF): δ 7.94 (m, 1H), 7.73 (d, 1H, J=6.4 Hz), 7.24-7.20 (m, 3H), 6.75-6.71 (m, 5H), 5.92-5.90 (m, 2H), 4.36-4.31 (m, 2H), 4.27-4.22 (m, 5H), 3.20 (br s, 2H); $^{13}$C (75 MHz, 5:1 D$_2$O:d$_7$-DMF): δ 171.1, 164.4, 155.7, 150.1, 140.5, 140.2, 130.1, 118.7, 112.9, 101.8, 101.2, 87.3, 81.8, 72.5, 68.3, 63.7, 63.2, 53.1, 41.2; ESI-MS calcd for C$_{32}$H$_{30}$N$_4$O$_{17}$P$_2$S [M–2H]$^{-2}$: 417.0323. found 417.0313.

133.5, 121.0, 115.7, 105.6, 105.1, 91.0, 86.0, 76.4, 72.8, 68.7, 67.5, 56.9, 45.1, 30.2, 27.5; ESI-MS calcd for C$_{34}$H$_{34}$N$_4$O$_{17}$P$_2$S [M–2H]$^{-2}$: 431.0479. found 459.0502.

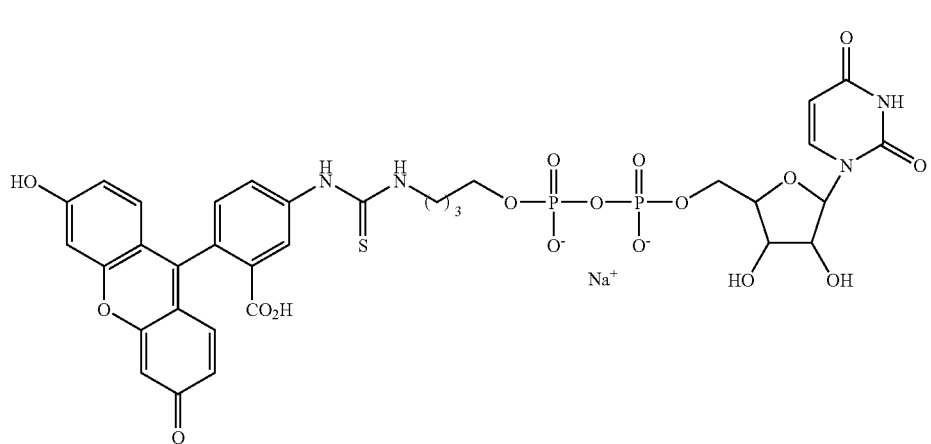

5b

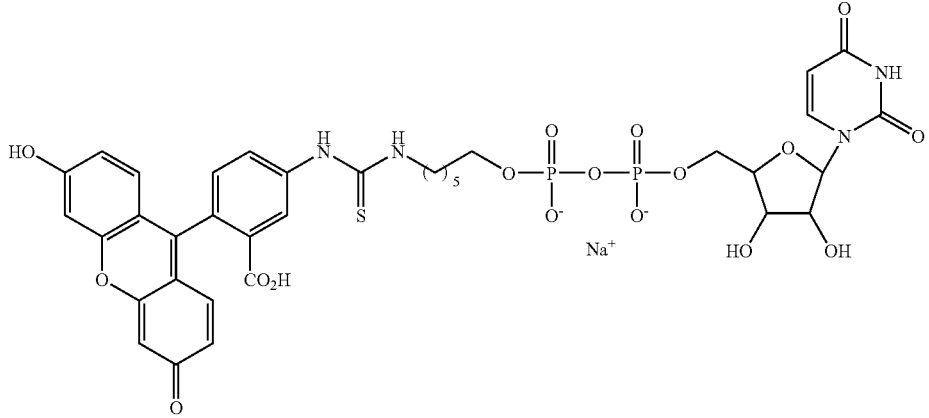

UDP-hexanolamine-fluorescein conjugate (5c): Following general procedure V, UDP-hexanolamine 4c (20 mg, 38 µmol) was combined with FITC (22 mg, 57 µmol) in 2:1 DMF/0.1 M NaHCO$_3$ (200 µL) to yield the sodium salt of UDP-hexanolamine-fluorescein conjugate 5c (13.7 mg, 40%) as a yellow solid (Soltero-Higgin, M.; Carlson, E. E.; Phillips, J. H.; Kiessling, L. L. *J. Am. Chem. Soc.* 2004, 126, 10532-10533.)

UDP-octanolamine-fluorescein conjugate 5d (4.7 mg, 90%) as a yellow solid. $^1$H (300 MHz, 5:1 D$_2$O:d$_7$-DMF): δ 8.14-8.10 (m, 1H), 7.88 (d, 1H, J=7.9 Hz), 7.34 (d, 1H, J=7.9 Hz), 7.23 (d, 2H, J=9.8 Hz), 6.79 (m, 4H), 6.10-6.06 (m, 2H), 4.46-4.43 (m, 2H), 4.33 (br s, 3H), 4.04 (m, 2H), 3.70 (br s, 2H), 1.73-1.68 (m, 4H), 1.47 (br s, 8H); $^{13}$C (75 MHz, 5:1 D$_2$O:d$_7$-DMF): δ 156.1, 150.6, 140.9, 130.3, 119.5, 112.1, 102.2, 101.7, 87.4, 82.7, 73.0, 69.1, 65.5, 64.1, 53.4, 41.6, 28.0, 27.6, 25.6, 24.4; ESI-MS calcd for C$_{38}$H$_{42}$N$_4$O$_{17}$P$_2$S [M−2H]$^{−2}$: 459.0792. found 459.0776.

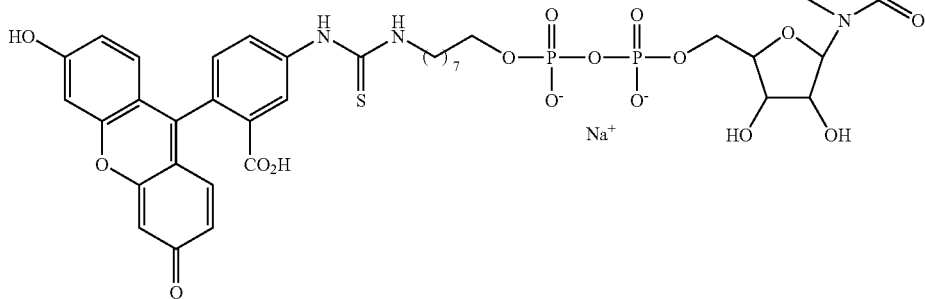

UDP-octanolamine-fluorescein conjugate (5d): Following general procedure V, UDP-octanolamine 4d (3.0 mg, 5.4 µmol) was combined with FITC (3.2 mg, 8.1 µmol) in 2:1 DMF/0.1 M NaHCO$_3$ (200 µL) to yield the sodium salt of

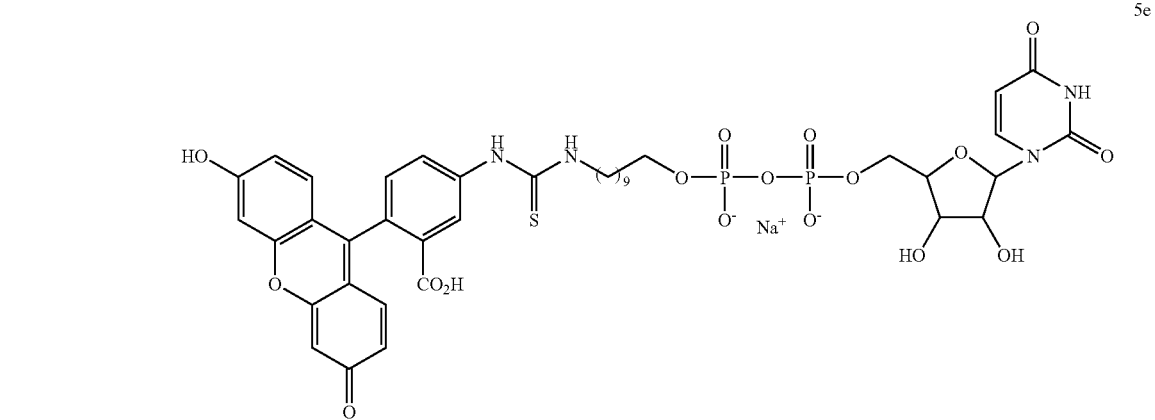

UDP-decanolamine-fluorescein conjugate (5e): Following general procedure V, UDP-decanolamine 4e (5 mg, 8.4 μmol) was combined with FITC (5 mg, 12.6 μmol) in 2/1 DMF/0.1 M NaHCO$_3$ (200 μL) to yield the sodium salt of UDP-decanolamine-fluorescein conjugate 5e (6.6 mg, 81%) as a yellow solid. $^1$H (300 MHz, 5:1 D$_2$O:d$_7$-DMF): δ 8.13 (br s, 1H), 7.90 (d, 1H, J=7.7 Hz), 7.63 (br s, 1H), 7.00 (br s, 1H), 6.73 (m, 2H), 6.66 (s, 2H), 6.54 (m, 2H), 5.88-5.84 (m, 2H), 4.25 (br s, 2H), 4.15 (br s, 2H), 3.83 (br s, 2H), 3.39 (br s, 2H), 1.44 (br s, 2H), 1.13 (br s, 4H), 1.03 (s, 8H); $^{13}$C (75 MHz, 5:1 D$_2$O:d$_7$-DMF): δ 179.2, 169.6, 164.3, 153.0, 150.4, 140.6, 128.9, 121.8, 116.9, 114.5, 110.6, 101.8, 101.5, 87.4, 82.4, 72.9, 68.8, 65.5, 64.0, 53.3, 43.3, 41.5, 28.2, 28.1, 27.9, 27.4, 25.5, 24.4; ESI-MS calcd for C$_{40}$H$_{46}$N$_4$O$_{17}$P$_2$S [M−2H]$^{−2}$: 473.0949. found 473.0965.

decanolamine 4g (2 mg, 3.3 μmol) was combined with FITC (2.0 mg, 5.0 μmol) in 2:1 DMF/0.1 M NaHCO$_3$ (200 μL) to yield the sodium salt of UDP-3,6,9-trioxa-undecanolamine-fluorescein conjugate 5g (2.5 mg, 76%) as a yellow solid. $^1$H (300 MHz, 5:1 D$_2$O:d$_7$-DMF): δ 7.91 (d, 1H, J=8.3 Hz), 7.86 (d, 1H, J=2.0 Hz), 7.65 (dd, 1H, 8.3, 2.1 Hz), 7.32 (dd, 2H, J=9.3, 4.0 Hz), 7.27 (d, 1H, J=8.2 Hz), 6.78 (dt, 2H, J=9.1, 2.2 Hz), 6.72 (s, 2H), 5.95-5.91 (m, 2H), 4.38-4.31 (m, 2H), 4.24 (br s, 3H), 4.15 (br s, 2H), 3.86-3.79 (m, 14H); $^{13}$C (75 MHz, 5:1 D$_2$O:d$_7$-DMF): δ 167.4, 160.4, 160.0, 154.1, 144.1, 143.0, 141.6, 134.3, 133.4, 123.6, 120.4, 117.4, 113.2, 105.8, 105.1, 91.1, 85.6 (d, J=4.8 Hz), 76.4, 72.6, 72.5, 72.3, 72.1, 71.4, 68.8, 67.8, 67.5; ESI-MS calcd for C$_{38}$H$_{42}$N$_4$O$_{20}$P$_2$S [M−2H]$^{−2}$: 483.0705. found 483.0720.

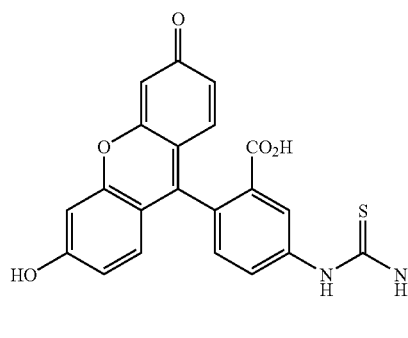

5f

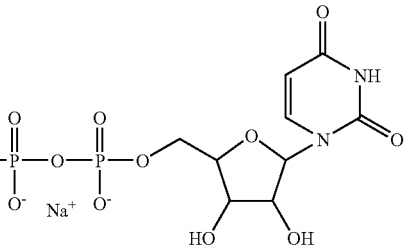

UDP-3,6-dioxa-octanolamine-fluorescein conjugate (5f): Following general procedure V, UDP-3,6-dioxa-octanolamine 4f (5 mg, 8.8 μmol) was combined with FITC (5.1 mg, 13.2 μmol) in 2:1 DMF/0.1 M NaHCO$_3$ (200 μL) to yield the sodium salt of UDP-3,6-dioxa-octanolamine-fluorescein conjugate 5f (5.6 mg, 66%) as a yellow solid. $^1$H (300 MHz, d$_7$-DMF): δ 8.25 (br s, 1H), 7.81 (br s, 1H), 7.26 (d, 1H, J=8.7 Hz), 6.91-6.66 (m, 9H), 5.90 (m, 2H), 4.34-4.26 (m, 2H), 4.18 (br s, 3H), 4.10 (br s, 2H), 3.80-3.66 (m, 10H); $^{13}$C (75 MHz, d$_7$-DMF): 181.8, 168.7, 153.2, 151.4, 143.0, 141.0, 130.4, 127.8, 119.2, 116.9, 114.6, 102.6, 102.5, 88.7, 84.8, 83.6, 74.0, 70.6, 70.3, 69.1, 66.7, 53.9, 44.0, 42.1, 17.9, 16.6, 12.16 ESI-MS calcd for C$_{36}$H$_{38}$N$_4$O$_{19}$P$_2$S [M−2H]$^{−2}$: 461.0574. found.

6

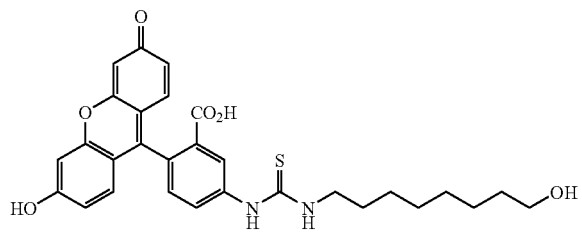

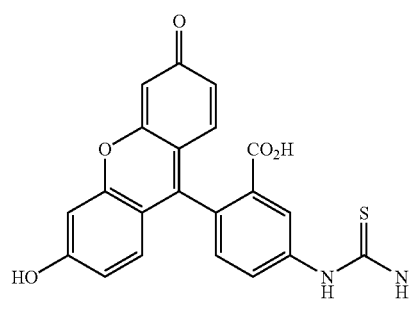

5g

UDP-3,6,9-trioxa-undecanolamine-fluorescein conjugate (5g): Following general procedure V, UDP-3,6,9-trioxa-un- Octanolamine-fluorescein conjugate (6): 8-amino-1-octanol (11.2 mg, 0.077 mmol) was combined with FITC (10 mg, 0.026 mmol) in MeOH (0.3 mL) and stirred at room-temperature for 1 h. The product was purified by silica gel chromatography (4:1 CH$_2$Cl$_2$/MeOH containing 1% H$_2$O) to yield control compound 6 (13.6 mg, 98%) as an orange solid. $^1$H (300 MHz, CD$_3$OD): δ 8.12 (d, 1H, J=1.7 Hz), 7.74 (dd, 1H, J=8.3, 1.6 Hz), 7.15 (d, 1H, J=8.2 Hz), 6.77 (d, 2H, J=8.8 Hz), 6.67 (d, 2H, J=2.3 Hz), 6.56 (dd, 2H, J=8.8, 2.2 Hz), 3.60-3.52 (m, 4H), 1.68-1.63 (m, 4H), 1.56-1.51 (m, 2H), 1.38 (m, 8H); $^{13}$C (75 mHz, CD$_3$OD): δ171.8, 155.2, 142.6, 131.0, 115.3, 112.6, 103.8, 63.2, 63.1, 33.8, 30.7, 30.6, 30.1, 28.2, 27.1); ESI-MS calcd for C$_{29}$H$_{30}$N$_2$O$_6$S [M−H]$^-$: 533.1825. found 533.1846.

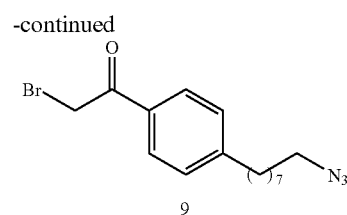

2-Bromo,4'-(8-azido-octyl)acetophenone (9), see Scheme 9: Aluminum chloride (3.25 g, 24 mmol) in CH$_2$Cl$_2$ (25 mL)

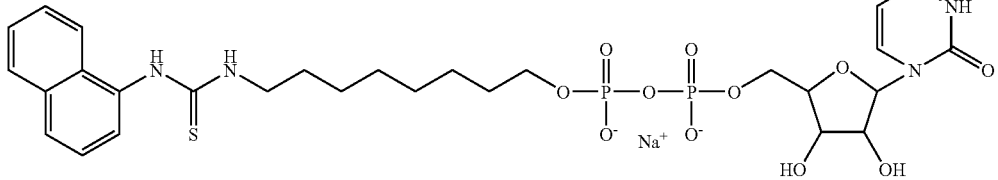

UDP-octanolamine-naphthyl conjugate (7): UDP-octanolamine 4d (25 mg, 50 μmol) was combined with 2-naphthyl isothiocyanate (20 mg, 100 μmol) in 3:1 DMF/0.1 M NaHCO$_3$ (200 μL). The reaction was stirred 1 h and concentrated. The product was purified by silica gel chromatography (12:10:1 CHCl$_3$/MeOH/H$_2$O) to yield the sodium salt of UDP-octanolamine-naphthyl conjugate 7 (30.9 mg, 83%) as an off-white solid: $^1$H (300 MHz, d$_7$-DMF): δ 8.05 (d, 1H, J=8.4 Hz), 8.00-7.91 (m, 2H), 7.59-7.46 (m, 5H), 5.98-5.93 (m, 2H), 4.36-4.33 (m, 2H), 4.19 (br s, 3H), 3.91 (br s, 2H), 3.51 (t, 2H, J=6.6 Hz), 1.54 (br s, 2H), 1.48 (br s, 2H), 1.24-1.15 (m, 8H); $^{13}$C (75 mHz, d$_7$-DMF): δ 164.4, 160.4, 150.8, 141.3, 133.9, 128.0, 127.5, 126.5, 126.3, 125.5, 125.1, 112.8, 117.6, 115.1, 101.9, 87.4, 83.1, 73.3, 69.4, 65.4, 64.3, 44.1, 28.4, 28.3, 28.1, 25.8, 24.7; ESI-MS calcd for C$_{28}$H$_{38}$N$_4$O$_{12}$P$_2$S [M−2H]$^{-2}$: 357.0763. found 357.0776.

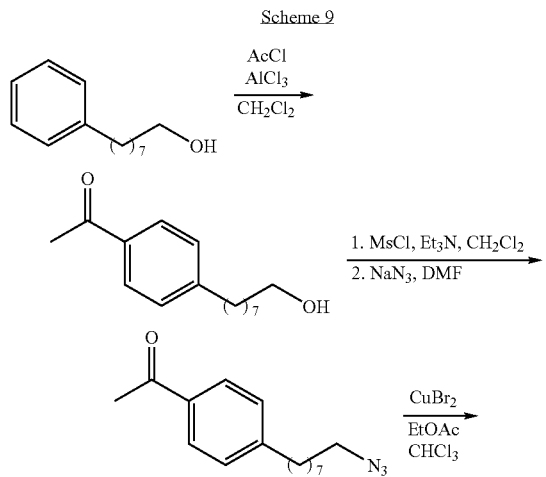

Scheme 9 was cooled to 0° C. To the pre-cooled solution, 8-phenyl-1-octanol (0.50 g, 2.4 mmol) in CH$_2$Cl$_2$ (2 mL) was added dropwise. Upon dropwise addition of acetyl chloride (0.343 mL, 4.8 mmol), the solution turned yellow. The solution was stirred for 12 h at room-temperature, after which it was poured into a mixture of ice and concentrated HCl. The mixture was stirred for 2 h until all salts were dissolved. The organic layer was separated, washed with saturated NaHCO$_3$ and brine, dried and concentrated. The product was purified by silica gel chromatography (10%→30% ethyl acetate in hexanes) to yield the acetophenone (0.352 g, 1.42 mmol) as an off-white solid in 59% yield. $^1$H (300 MHz, CDCl$_3$): δ 7.74 (d, 2H, J=8.1 Hz), 7.12 (d, 2H, J=8.1 Hz), 3.49 (t, 2H, J=6.7 Hz), 2.51 (t, 2H, J=7.5 Hz), 2.43 (s, 3H), 1.49-1.41 (m, 4H), 1.20 (m, 8H); $^{13}$C (75 mHz, CDCl$_3$): δ 197.9, 148.6, 134.7, 128.4, 128.3, 62.4, 35.8, 32.5, 30.9, 29.3, 29.2, 29.0, 26.3, 25.7; EI-MS calcd for C$_{16}$H$_{24}$O$_2$ [M+.]: 248.1776. found 248.1777.

Triethylamine (0.296 mL, 2.12 mmol) was added to a solution of acetophenone (0.262 g, 1.06 mmol) in CH$_2$Cl$_2$ (10 mL). Mesyl chloride (0.165 mL, 2.12 mmol) was added dropwise, and the solution was stirred 1 h under N$_2$. The pink solution was washed with brine, dried, filtered and concentrated. The crude product was combined with sodium azide in DMF (8 mL) and stirred for 12 h at 80° C. A solution of 10% EtOAc in hexanes (100 mL) was added to the reaction, which was washed twice with brine (50 mL), filtered and evaporated. The product was purified by silica gel chromatography (5%→10% ethyl acetate in hexanes) to yield the azide (0.243 g, 0.889 mmol) as an oil in 84% yield. $^1$H (300 MHz, CDCl$_3$): δ 7.77 (d, 2H, J=8.1 Hz), 7.15 (d, 2H, J=8.2 Hz), 3.13 (t, 2H, J=6.8 Hz), 2.55 (t, 2H, J=7.6 Hz), 2.46 (s, 3H), 1.55-1.43 (m, 4h), 1.22 (m, 8H); $^{13}$C (75 mHz, CDCl$_3$): δ197.6, 148.6, 135.0, 128.6, 128.5, 51.4, 39.9, 31.0, 29.3, 29.1, 29.0, 28.8, 26.7, 26.5; ESI-MS calcd for C$_{16}$H$_{23}$N$_3$O [M+Na]$^+$: 296.1739. found 296.1753.

A solution of CuBr$_2$ (76.3 mg, 0.342 mmol) in EtOAc (1 mL) was heated to reflux. A solution of acetophenone in CHCl$_3$ (1 mL) was added dropwise. The solution was stirred at reflux until all CuBr$_2$ appeared to be consumed (precipitate turns white). The solution was filtered, concentrated, and the product purified by silica gel chromatography (2%→4% EtOAc in hexanes) to yield 2-bromo,4'-(8-azido-octyl)acetophenone 9 in 43% yield (32.7 mg, 0.093 mmol). $^1$H (300 MHz, CDCl$_3$): δ 7.89 (d, 2H, J=8.4 Hz), 7.28 (d, 2H, J=7.3 Hz), 4.43 (s, 2H), 3.25 (t, 2H, 4.8 Hz), 2.65 (m, 2H), 1.59 (m, 4H), 1.33 (m, 8H); $^{13}$C (75 mHz, CDCl$_3$): δ 191.2, 150.0, 148.9, 129.1, 128.7, 77.1, 36.2, 31.2, 31.1, 29.5, 29.3, 23.2, 29.0, 26.9; ESI-MS calcd for C$_{16}$H$_{23}$N$_3$O [M+Na]$^+$: 374.0844. found 374.0854.

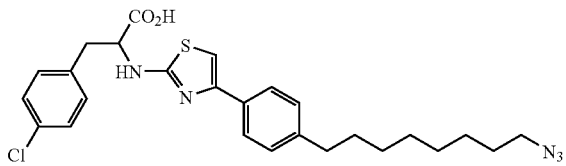

10

3-(4-Chlorophenyl)-2-[4-(8-azido-octyl-phenyl)-thiazol-2-ylamino]-propionic acid (10): Thiourea (see Example 1) (26.4 mg, 0.102 mmol) and α-bromoketone 9 (32.7 mg, 0.093 mmol) were combined in DMF (300 μL). The reaction was stirred under nitrogen for 2 h and concentrated. The product was purified by silica gel chromatography (3:1 hexanes/EtOAc→2:1 hexanes/EtOAc containing 2% AcOH) to yield 10 (17 mg, 0.033 mmol) as a white solid in 36% yield. $^1$H (300 MHz, CDCl$_3$): δ 7.54 (d, 2H, J=7.7 Hz), 7.17 (m, 6H), 6.45 (s, 1H), 4.24 (m, 1H) 3.35 (dd, 1H, J=14.2, 5.3 Hz), 3.25 (t, 2H, J=6.7 Hz), 3.15 (dd, 1H, J=13.3, 6.2 Hz), 2.62 (t, 2H, J=7.5 Hz), 1.59 (m, 4H), 1.32 (m, 8H); $^{13}$C (75 mHz, CDCl$_3$): δ 174.3, 169.9, 143.8, 135.7, 132.9, 131.2, 129.0, 128.8, 126.3, 99.4, 61.9, 51.7, 37.7, 35.9, 31.4, 29.5, 29.4, 29.3, 29.0, 26.9: ESI-MS calcd for C$_{26}$H$_{30}$ClN$_5$O$_2$S [M–H]$^-$: 510.1730. found 510.1741.

39.6, 36.8, 35.4, 31.2, 29.1, 29.0, 27.4, 26.3; ESI-MS calcd for C$_{26}$H$_{32}$ClN$_3$O$_2$S [M+H]$^+$: 486.1982. found 486.1969.

The amine (11.3 mg, 23 μmol) was combined with fluorescein isothiocyanate (10.4 mg, 35 μmol) and DIEA (12 μL, 69 μmol) in DMF (400 μL). The solution was stirred 1.5 h and concentrated. The product was purified using HPLC (gradient 50-70% ACN/H$_2$O) to yield 11 as an orange solid (16.2 mg, 18.5 μmol) in 80% yield. $^1$H (300 MHz, CD$_3$OD): δ 8.11 (s, 1H), 7.70 (d, 1H, J=8.1 Hz), 7.51 (d, 2H, J=7.8 Hz), 7.20 (s, 4H), 7.15 (d, 2H, J=8.5 Hz), 7.08 (d, 1H, J=8.2 Hz), 6.71 (d, 2H, J=8.5 Hz), 6.68 (d, 2H, J=2.1 Hz), 6.54 (dd, 2H, J=8.8, 2.4 Hz), 4.66 (dd, 1H, J=8.4, 5.0 Hz), 3.53 (m, 2H), 3.30 (dd, 1H, J=14.4, 5.0 Hz), 3.05 (dd, 1H, J=14.0, 8.2 Hz), 2.56 (t, 2H, J=7.8 Hz), 1.60-1.57 (m, 4H), 1.31 (br s, 8H); $^{13}$C (75 mHz, CD$_3$OD): δ 182.5, 173.4, 170.4, 170.1, 154.6, 136.5, 133.6, 131.8, 130.5, 129.6, 129.3, 126.9, 126.0, 114.1, 144.0, 103.2, 60.4, 60.3, 37.7, 36.3, 32.1, 30.1, 30.0, 29.8, 29.6, 27.6; LC/MS (ESI) (m/z) [M+H]$^+$ calcd 875.3. found 875.3.

UGM Binding

Fluorescence Polarization Binding Assay:

Serial dilutions of dialyzed UGM (maximum concentration was typically 30 μM) was incubated with 15 nM of fluorescent compounds 5a-5f, 6 or 11 in 50 mM sodium phosphate buffer, pH 7.0 at 25° C. Final volumes were 30 μL in 384 well black microtiter plates (Costar). Fluorescence polarization was analyzed using a Wallac EnVision plate reader. Data were fit to y=m1+((m2−m1)*x^m3)/(m4^m3+x^m3); m2=maximum FP signal, m1=minimum FP signal, m3=slope, m4=binding constant (KaleidaGraph, Synergy Software).

Fluorescence Polarization Inhibition Assay:

The fluorescence polarization inhibition assay was performed as previously described (22). Reactions contained 580 nM UGM$_{myco}$ or 500 nM UGM$_{kleb}$ and 15 nM of the fluorescent probe 5c in 50 mM sodium phosphate buffer, pH 7.0 at 25° C. Final volumes were 30 μL in 384 well black microtiter plates (Costar). Serial dilutions of UDP, 4d or 7 were added to the wells. Fluorescence polarization was analyzed using a Wallac

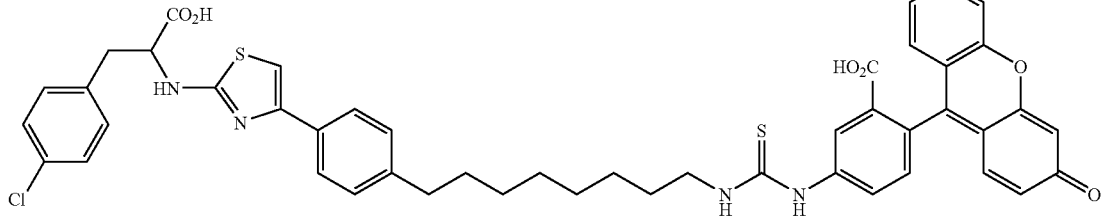

11

Figure 13A:
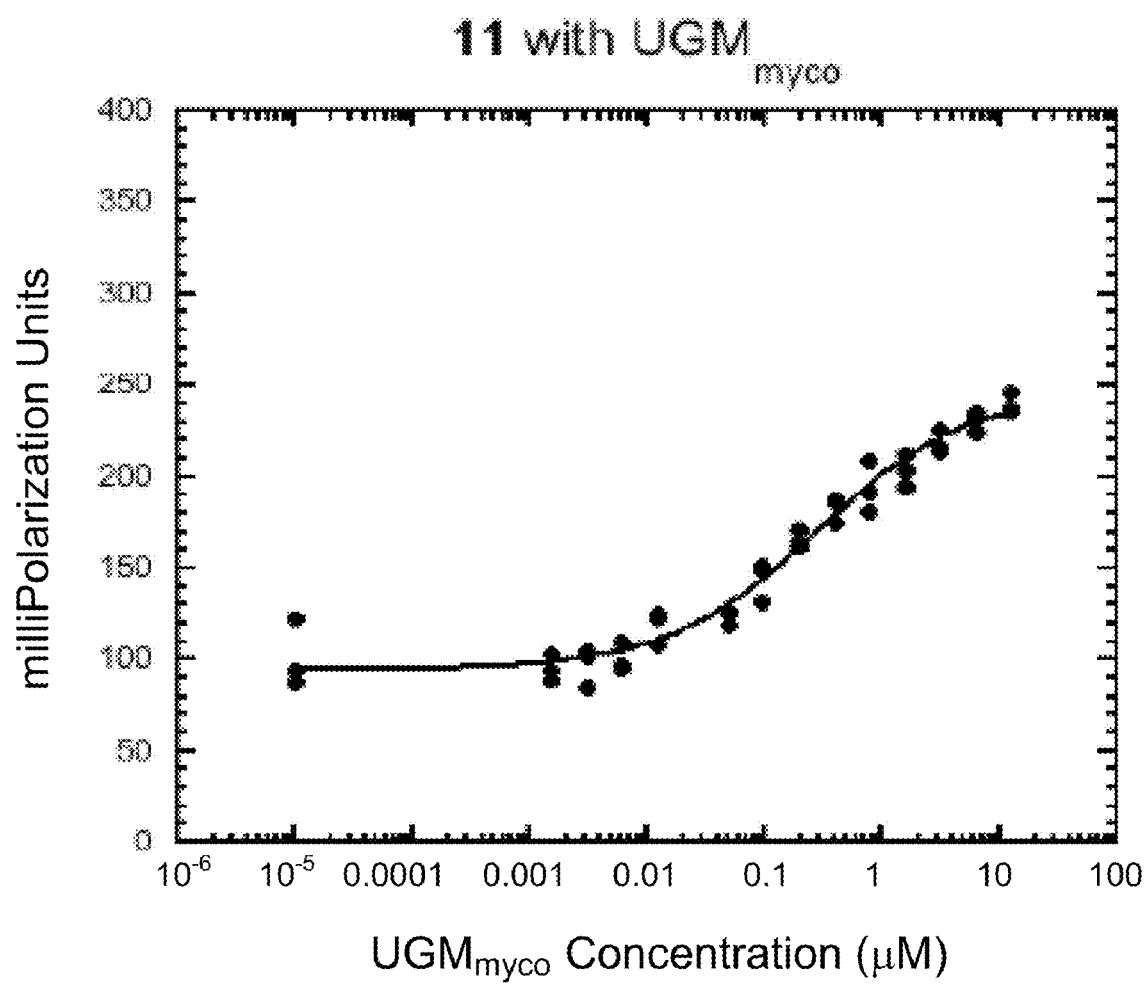
FIGS. 13A and 13B are graphs illustrating determination of $K_d$ for compound 11 for $UGM_{myco}$ and $UGM_{kleb}$, respectively.
Figure 13B:
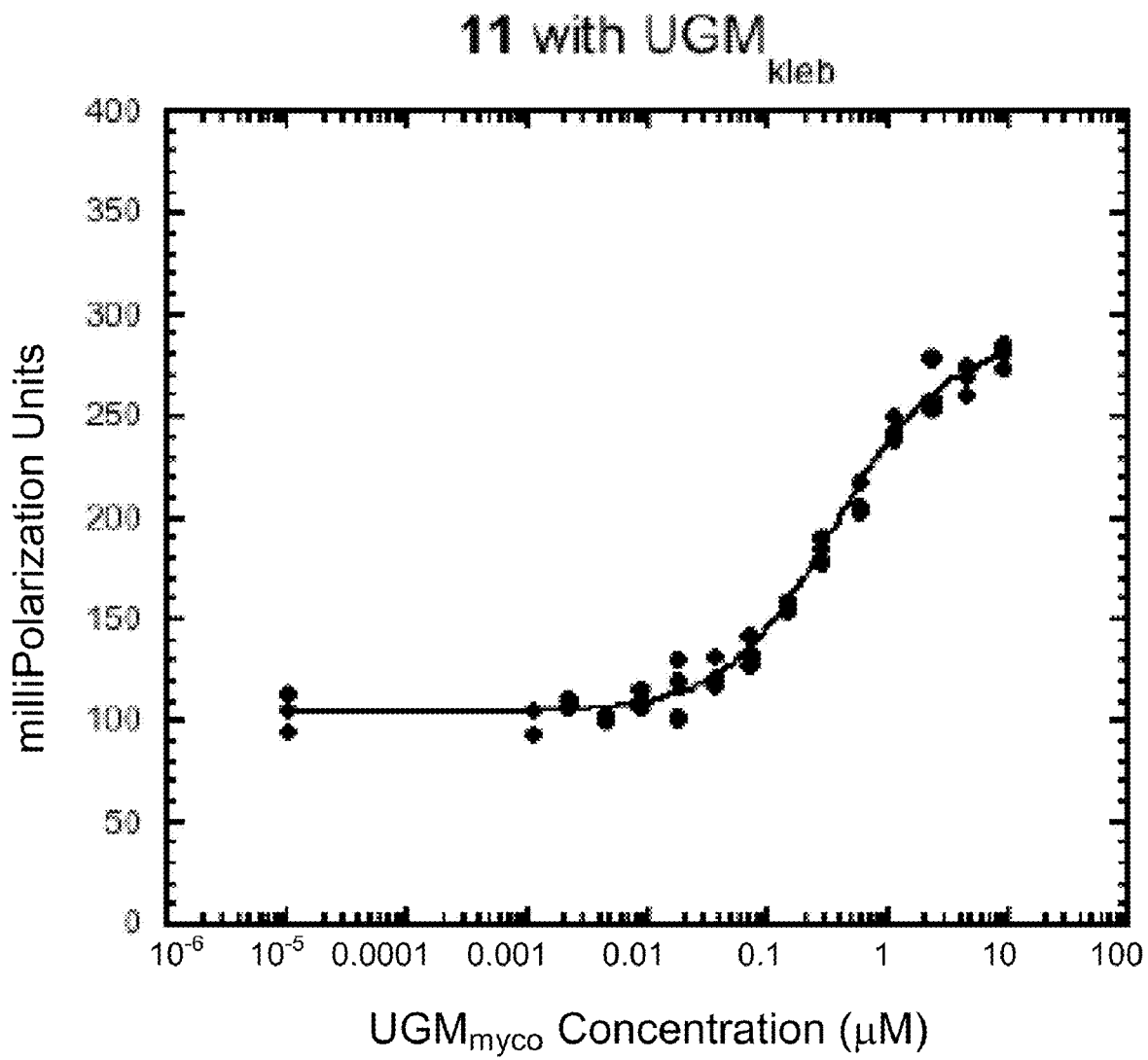

Aminothiazole-fluorescein conjugate (11): Azide 10 (12 mg, 23 μmol) was combined with Pd(OH)$_2$/C (6 mg) in 4:1 MeOH/CHCl$_3$ (0.5 mL) and stirred 12 h under H$_2$ (1 atm). The suspension was filtered over celite and the filtrate was concentrated to yield the amine as a white solid (11.3 mg, 23 μmol) in quantitative yields. $^1$H (300 MHz, CD$_3$OD): δ 7.47 (d, 2H, J=7.9 Hz), 7.47 (d, 2H, J=7.9 Hz), 7.27 (m, 7H), 3.42 (dd, 1H, J=14.3, 3.9 Hz), 3.11 (dd, 1H, J=14.3, 8.7 Hz), 2.86 (t, 2H, J=7.1 Hz), 2.62 (t, 2H, J=7.7 Hz), 1.60 (m, 4H), 1.32 (m, 8H); $^{13}$C (75 mHz, CD$_3$OD): δ 170.5, 170.3, 145.5, 140.2, 134.9, 133.2, 131.0, 129.1, 128.7, 126.4, 125.8, 60.4, 39.7, EnVision plate reader. Data were fit to y=m1+((m2−m1)*x^m3)/(m4^m3+x^m3); m2=maximum FP signal, m1=minimum FP signal, m3=slope, m4=apparent binding constant (KaleidaGraph, Synergy Software). To determine K$_d$ values, the apparent binding constant was then subjected to K$_{app}$=K$_d$(1+(I)/K$_f$), where I=concentration of the fluorescent probe and K$_f$=binding affinity of the fluorescent probe to UGM. For UGM$_{myco}$ I=15 nM and K$_f$=160 nM. For UGM$_{kleb}$ I=15 nM and K$_f$=100 nM. Data for exemplary compounds is provided in Table 2. FIGS. 13A and 13B are graphs illustrating determination of K$_d$ for compound II for UGM$_{myco}$ (FIG. 13A) and UGM$_{kleb}$ (FIG. 13B).

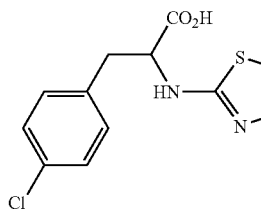
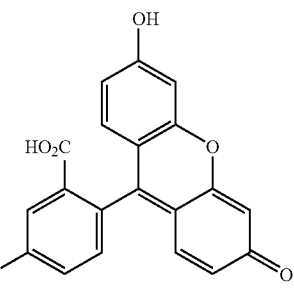

11

TABLE 2

Exemplary Results of Fluorescence Polarization UMG Inhibition Assay

| Compound | $K_d$ (UMG$_{myco}$) [μM] | $K_d$ (UMG$_{kleb}$) [μM] |
|---|---|---|
| 11 | 0.295 ± 0.066 | 0.385 ± 0.035 |
| 7 | 0.610 ± 0.109 | 0.583 ± 0.036 |
| 6 | >30 | >30 |
| 5a | >30 | >30 |
| 5b | 2.51 ± 0.28 | 1.94 ± 0.15 |
| 5c | 0.166 ± 0.014 | 0.193 ± 0.011 |
| 5d | 0.054 ± 0.006 | 0.045 ± 0.002 |
| 5e | 0.064 ± 0.004 | 0.070 ± 0.002 |
| 5f | 0.575 ± 0.016 | 0.767 ± 0.017 |
| 5g | 1.07 ± 0.10 | 1.20 ± 0.14 |
| 4d | 32.0 ± 3.4 | 37.7 ± 1.5 |
| UDP | 15.1 ± 1.7 | 26.0 ± 1.7 |

We claim:

1. A compound having the formula:

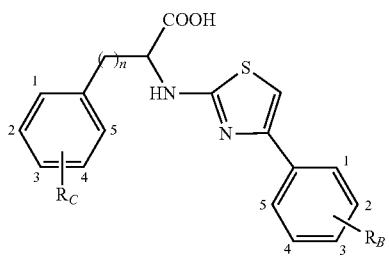

or salts thereof, wherein n=0 or 1, $R_C$ represents substitution by a halogen at ring position 3 and $R_B$ represents substitution by a halogen at ring position 3, substitution by two halogens at ring positions 2 and 4, substitution by two halogens at ring positions 1 and 3, substitution by a nitro group at ring position 2 or substitution by a hydroxyl group at ring position 3.

2. A compound of claim 1 wherein:

$R_C$ represents substitution by a chlorine, iodine or bromine at ring position 3; and $R_B$ represents substitution by chlorine, iodine or bromine at ring position 3, substitution by two chlorines or fluorines at ring positions 2 and 4, substitution by two chlorines or fluorines at ring positions 1 and 3, substitution by a nitro group at ring position 2, or substitution by a hydroxyl group at ring position 3.

3. A compound of claim 2 wherein $R_C$ represents substitution at ring position 3.

4. The compound of claim 1 having a formula selected from:

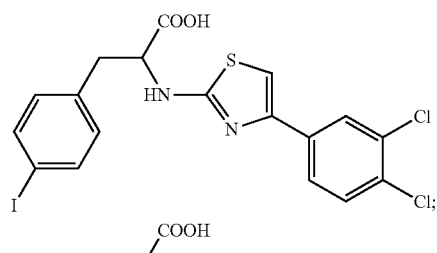

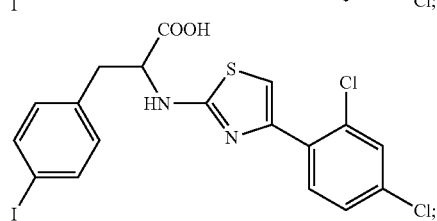

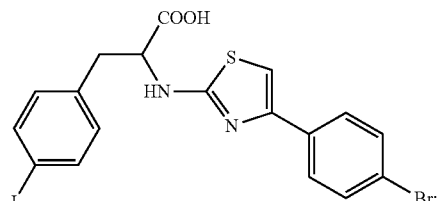

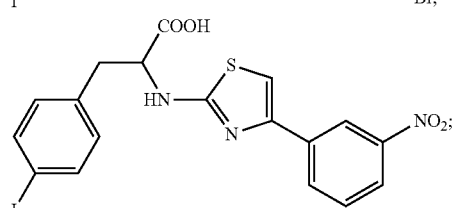

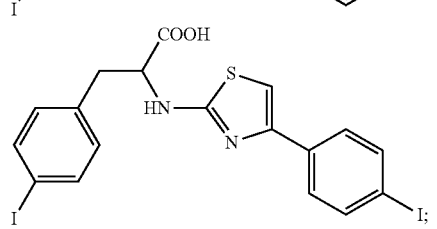

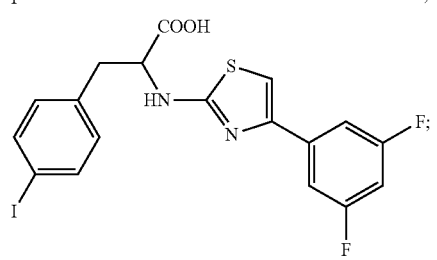

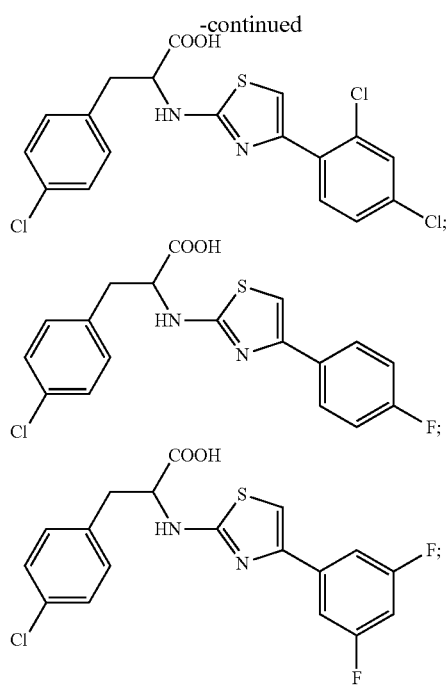
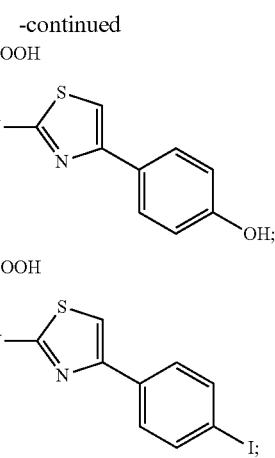
or salts thereof.
5. A method for inhibiting UGM which comprises the step of contacting UGM with an amount of one or more compounds of claim 1 effective for inhibiting the enzyme.
* * * * *